US010400010B2

(12) United States Patent
Eisenberg et al.

(10) Patent No.: US 10,400,010 B2
(45) Date of Patent: Sep. 3, 2019

(54) STRUCTURE-BASED PEPTIDE INHIBITORS OF P53 AGGREGATION AS A NEW APPROACH TO CANCER THERAPEUTICS

(71) Applicant: THE REGENTS OF THE UNIVERSITY OF CALIFORNIA, Oakland, CA (US)

(72) Inventors: David S. Eisenberg, Los Angeles, CA (US); Alice Soragni, Los Angeles, CA (US); Lin Jiang, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/877,134

(22) Filed: Jan. 22, 2018

(65) Prior Publication Data
US 2018/0155396 A1    Jun. 7, 2018

Related U.S. Application Data

(62) Division of application No. 14/889,604, filed as application No. PCT/US2014/037387 on May 8, 2014, now Pat. No. 9,873,718.

(60) Provisional application No. 61/821,157, filed on May 8, 2013.

(51) Int. Cl.
C07K 7/06      (2006.01)
G16B 15/00     (2019.01)
G16B 20/00     (2019.01)
C07K 14/47     (2006.01)
A61K 38/00     (2006.01)

(52) U.S. Cl.
CPC ............ C07K 7/06 (2013.01); C07K 14/4711 (2013.01); C07K 14/4746 (2013.01); G16B 15/00 (2019.02); G16B 20/00 (2019.02); *A61K 38/00* (2013.01); *C07K 2319/10* (2013.01); *C07K 2319/33* (2013.01); *C07K 2319/70* (2013.01)

(58) Field of Classification Search
CPC ............... A61K 38/00; C07K 14/4711; C07K 14/4746; C07K 2319/10; C07K 2319/33; C07K 2319/70; C07K 7/06; G16B 15/00; G16B 20/00
See application file for complete search history.

(56) References Cited

U.S. PATENT DOCUMENTS 8,304,211 B2 * 11/2012 El-Gewely ............... C07K 7/06 435/375
9,389,219 B2 *  7/2016 Schymkowitz .... G01N 33/5011
9,517,252 B2 * 12/2016 Goh ......................... C07K 5/081
9,873,718 B2 *  1/2018 Eisenberg ............... C07K 7/06

2009/0111154 A1   4/2009  Liao et al.
2010/0204085 A1   8/2010  Eisenberg et al.
2014/0170239 A1   6/2014  Schymkowitz et al.

FOREIGN PATENT DOCUMENTS

| CN | 1692126       | 11/2005  |
| EP | 1947113       | 7/2008   |
| EP | 1515985       | 1/2013   |
| WO | 2004031229    | 4/2004   |
| WO | WO2005/074521 | * 8/2005 |
| WO | 2012130785    | 10/2012  |

OTHER PUBLICATIONS

Pel et al. Genome sequencing and analysis of the versatile cell factory Aspergillus niger CBS 513.88. Nature Biotechnology, 2007. vol. 25, No. 2, pp. 221-231.
Moran et al. Genome sequence of Silicibacter pomeroyi reveals adaptatins to the marine environment. Nature, 2004. vol. 432, pp. 910-913.
Miletti. Cell-penetrating peptides: classes, origin, and current landscape. Durg Discovery Today, 2012. vol. 17, Nos. 15-16, pp. 850-860.
Pierce. Technical Resource. Protein stability and storage. 2005. accessed online at http://www.indiana.edu/~Ichenlab/protocol_files/protein_storage.pdf on Apr. 14, 2017. 3 pages.
Uhlig et al. The emergence of peptides in the pharmaceutical business: From exploration to exploitation. EuPA Open Proteomics, Sep. 2014. pp. 58-69.
Nicoloff et al. Repression of the pyr Operon in Lactobacillus plantarum Prevents Its Ability to Grow at Low Carbon Dioxide Levels. Journal of Bacteriology, Mar. 2005. vol. 187, No. 6, pp. 2093-2104.
Lang et al. Complete genome sequence of Dyadobacter fermentans type strain (NS114T). Standards in Genomic Sciences 2009, vol. 1. pp. 133-140.
EP Search Report dated Nov. 22, 2016, EP Application No. 14795260.0.
Arsene-Ploetze F., et al., Database GenBank [online] NCBI; Dec. 5, 2006, "PyrR1 protein", XP002763886, retrieved from https://www.ncbi.nlm,nih,gov/protein/caj75868.
NCBI, NCBI Reference Sequence No. YP_003089273.1, Dec. 23, 2012.
Born et al. "Mutant p53 aggregates into prion-like amyloid oligomers and fibrils: Implications for cancer", The Journal of Biological Chemistry, vol. 287, No. 33, pp. 28152-28162, 2012.
Olson et al. "Activatable cell penetrating peptides linked to nanoparticles as dual probes for in vivo fluorescence and MR imaging of proteases", PNAS, vol. 107, No. 9, pp. 4311-4316, 2010.

(Continued)

*Primary Examiner* — Marcela M Cordero Garcia
(74) *Attorney, Agent, or Firm* — Gates & Cooper LLP

(57) ABSTRACT

This invention relates, e.g., to an inhibitory peptide or CPP inhibitor which specifically binds to p53 having an aberrant conformation (e.g., is aggregated or misfolded) and inhibits p53 amyloidogenic aggregation or restores proper folding of the misfolded protein. Methods of using the inhibitory peptide or CPP inhibitor (e.g. to treat subjects having tumors that comprise aggregated p53) are described.

30 Claims, 13 Drawing Sheets

Specification includes a Sequence Listing.

(56) References Cited

OTHER PUBLICATIONS

International Search Report and Written Opinion for PCT/US2014/037387 dated Sep. 5, 2014.
CN Office Action dated Sep. 14, 2018, Application No. 201480036100.8, English translation only.
Lang, E., et al., "helix-turn-helix domain protein [Dyadobacter fermentans DSM 18053]", GenBank Accession: ACT96108.1, Jun. 4, 2010.

* cited by examiner

A.

B.

STRUCTURE-BASED PEPTIDE INHIBITORS OF P53 AGGREGATION AS A NEW APPROACH TO CANCER THERAPEUTICS

CROSS REFERENCE TO RELATED APPLICATIONS

This application is a divisional application that claims the benefit under 35 U.S.C. § 121 of U.S. patent application Ser. No. 14/889,604 (issued as U.S. Pat. No. 9,873,718), filed Nov. 6, 2015, which is the National Stage of International Application No. PCT/US2014/037387 (International Publication No. WO2014/182961), filed May 8, 2014, which claims priority under Section 119(e) from U.S. provisional application Ser. No. 61/821,157, filed May 8, 2013, which is incorporated by reference herein in its entirety.

STATEMENT AS TO RIGHTS TO INVENTIONS MADE UNDER FEDERALLY SPONSORED RESEARCH AND DEVELOPMENT

This invention was made with Government support under Grant No. NSF MCB-0958111 awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, created on May 8, 2014, is named 58086-364665_SL.txt and is 24,636 bytes in size.

BACKGROUND INFORMATION

Mutations in the tumor suppressor p53 are associated with 50% of all reported human cancers (Soussi et al., 2006). Structural instability of p53 mutants leads to partial unfolding (Bullock and Fersht, 2001) which in turn may cause p53 to form aggregates similar to those seen in amyloid diseases, such as Alzheimer's Disease (Xu et al, 2011; Levy et al, Eisenberg and Jucker, 2012). The process of p53 misfolding and aggregation results in protein inactivation, thereby removing the 'guardian of the genome' from its protective function (Xu et al, 2011).

In the past decades, it has been shown that several different p53 mutations, in particular those deemed to be "structural mutations," affect p53 folding, lowering protein stability and inducing partial unfolding (Bullock and Fersht, 2001). These aberrant p53 conformations have been demonstrated in cancer biopsies by using the mutant-specific antibody PAb240 which recognizes an epitope buried in the protein core that gets solvent exposure only upon misfolding (Gannon et al, 1990). In addition, several lines of evidence have shown that fragments of p53 (Ishimaru et al, Biochemistry 2003; Silva et al, 2010; Ishimaru et al, 2009; Galea et al, 2005; Rigacci et al, 2008) as well as full-length mutant p53 (Wang et al, PNAS, 2012) undergo amyloidogenic aggregation in vitro. In addition, p53 was reported to be in the misfolded aggregated amyloid state in biopsies derived from breast cancer cases (Levy et al, 2011) as well as colon carcinomas (Xu et al, 2011) and basal cell carcinomas (Lasagna-Reeves et al, 2013).

There is a need for agents that can specifically destabilize p53 aggregates or prevent them from forming, in particular agents which are designed in a rational structure-based approach, for use in treating forms of cancer in which p53 is inactivated due to the fact that it is aberrantly folded and/or aggregated (is found inactive in fibrous form). Since about half of all diagnosed tumors present with p53 mutations, the potential for applicability of such a targeted therapeutic agent is great.

DESCRIPTION OF THE DRAWINGS

The patent or application file contains at least one drawing executed in color.

5, treatment with the inhibitor but not with a scrambled peptide causes p53 to re-localize to the nucleus. In the bottom, the transition is accompanied by a refolding step: upon treatment with the inhibitor the antibody PAb240 does not bind to p53 in these cells, even though p53 is present in abundance (see DO-1 stain above). The PAb240 commercial antibody recognizes misfolded p53, therefore loss of PAb240 antigeneicity reflects a change in the p53 population from misfolded to properly folded, functionally capable protein.

Figure 6:
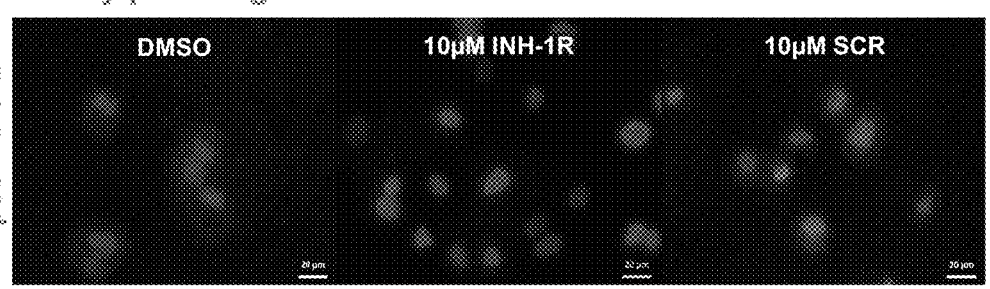
FIG. 6 shows that INH-1R CPP causes misfolded p53 to acquire a wild type-like, functional fold. A stable cell line derived from an ovarian cancer tumor is stained with the commercially available DO-1 antibody which recognizes any p53, irrespective of its structural state. As shown in FIG.
Figure 6:
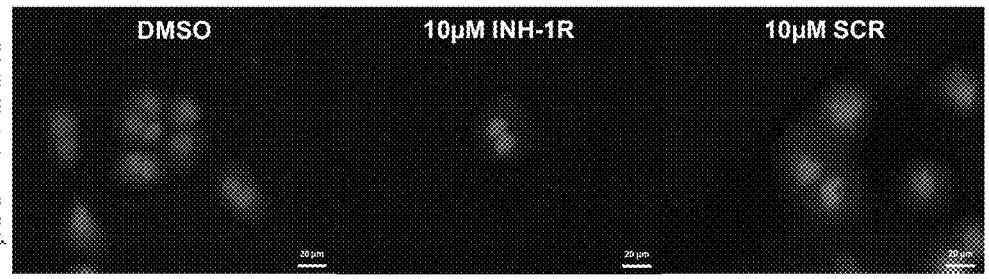
Figure 7:
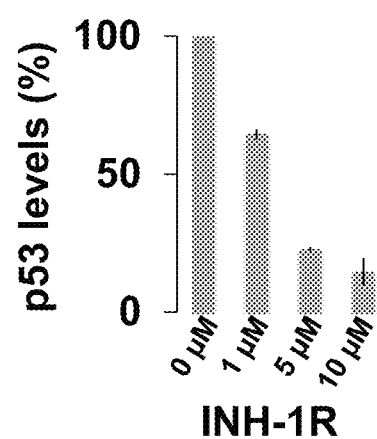

FIG. 7 shows that INH-1R CPP treated cells have a functional p53 that can respond to physiological regulation systems. p53 levels in OVCAR-3 cell lysates treated for 24 hours with 0, 1, 5 or 10 µM INH-1R were assessed by Western Blot and quantified using ImageJ. The total amount of p53 decreases upon 1NH-1R CPP treatment in a concentration dependent manner. The properly folded p53 (see FIG. 6) can now be degraded as is WT p53. The hyperstability due to misfolding/aggregation is lost, and the protein turnover is fast.

Figure 8:
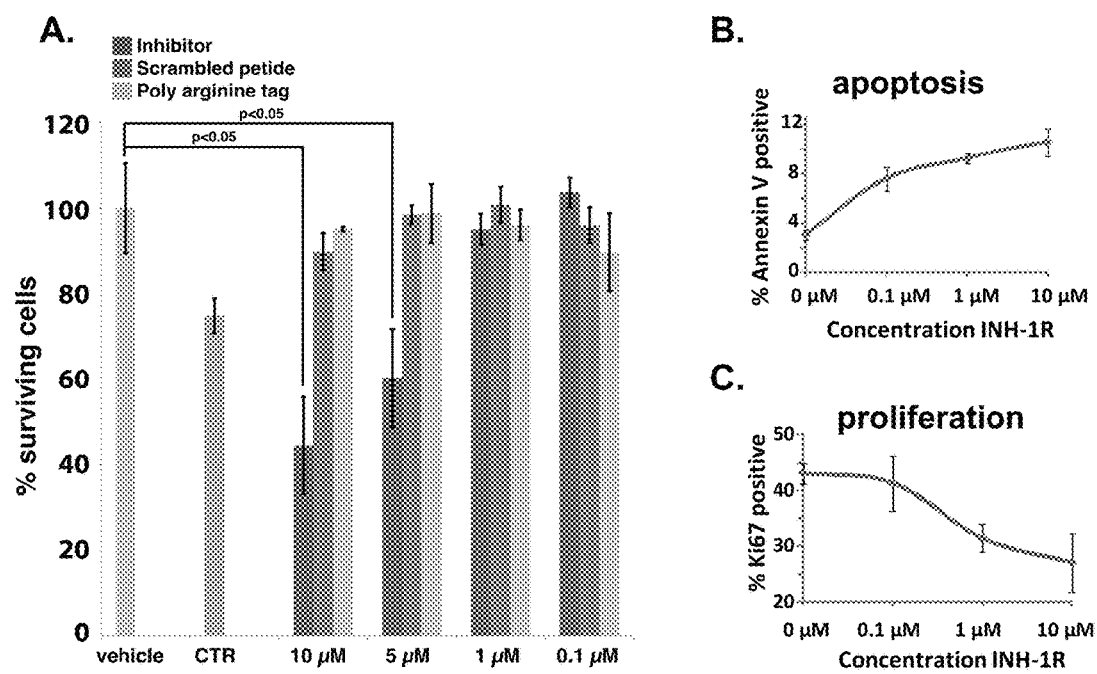

FIG. 8 shows that INH-1R CPP CPP effectively induces cell death in tumors cells bearing misfolded/aggregation-prone mutant p53. A. Dose dependent reduction of cell viability was detected in cells treated with 10 µM INH-1R CPP for 24 hours. Increased apoptosis (B.) and decreased proliferation (C.) was observed with increasing INH-1R CPP dosage. B. and C. show one representative case of primary cells from ovarian cancer. Similar results were observed with all sensitive primary cells as well as cell lines.

Figure 9:
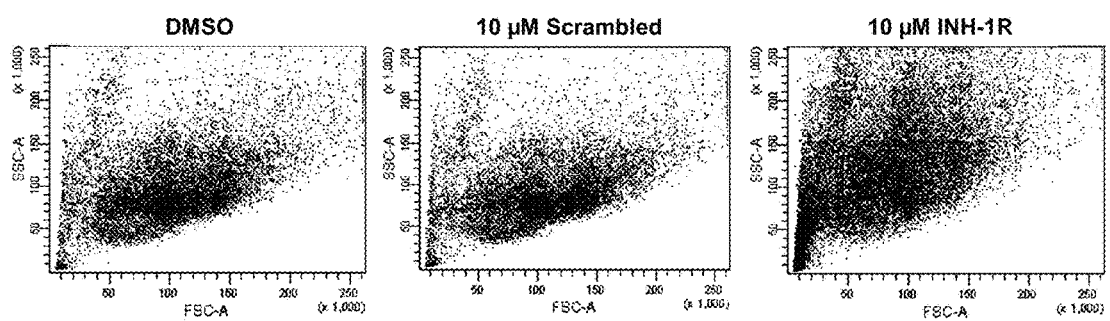

FIG. 9 shows that INH-1R CPP effectively induces cell death in cancer cells. Cells treated for 24 hours with either INH-1R or a control peptide were trypsinized and analyzed by FACS. Cell death is accompanied by a typical reduction of cell size and an increase in granularity in cells treated with INH-1R CPP as compared to vehicle treated cells (DMSO). Cancer cells treated with a control scrambled peptide sequence did not show any change in cell size or granularity.

Figure 10:
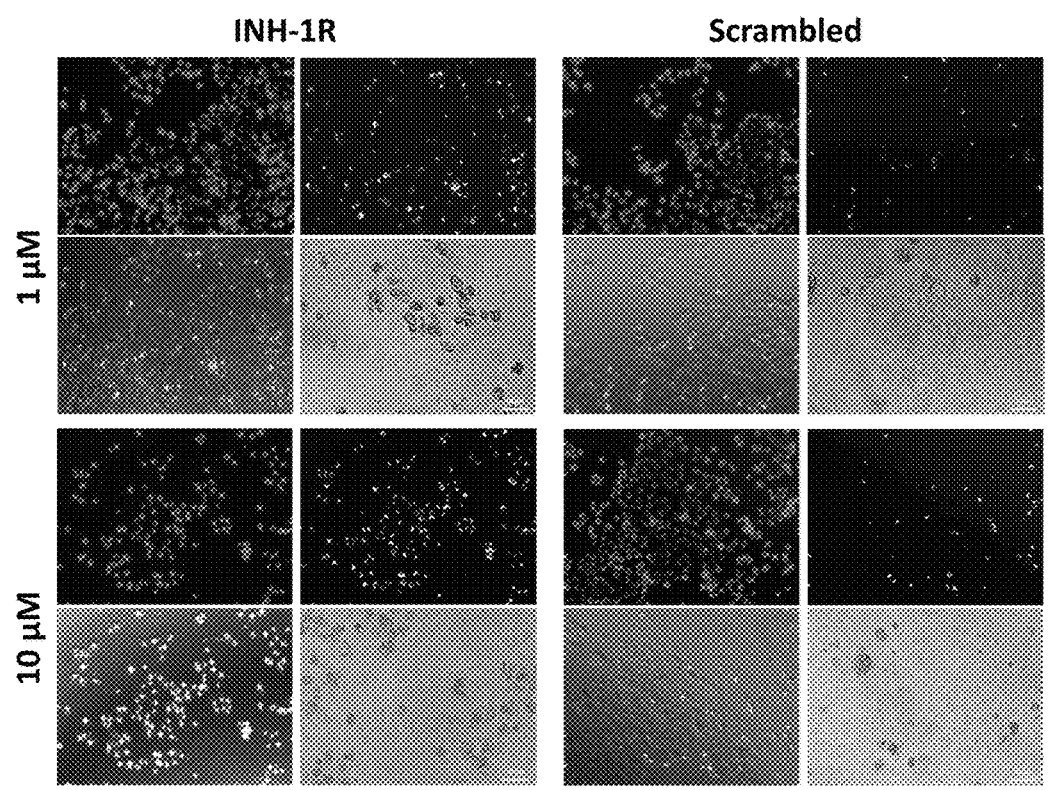

FIG. 10 shows apoptosis and necrosis in cancer cells treated with INH-1R CPP. OVCAR-3 cells were treated for 24 hours with the indicated concentrations of either INH-1R CPP or a scrambled inhibitor sequence. Hoechst (blue) stains all nuclei while YO-PRO-1 (green) only stains apoptotic cells and propidium iodide (red) stains late apoptotic/necrotic cells. The samples treated with the inhibitor contain mostly dead cells, while the scrambled peptide has no effect, indicative of sequence specific effect.

Figure 11:
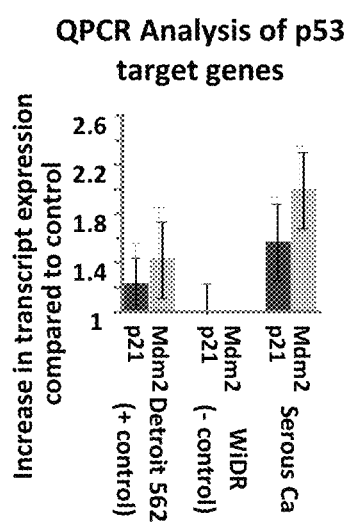

FIG. 11 shows that INH-1R CPP induces up-regulation of p53 target genes p21 and Mdm2. Specificity and efficacy of INH-1R CPP was confirmed by up-regulation of p53 target genes only in tumor cells containing p53 misfolding/aggregating mutations.

Figure 12:
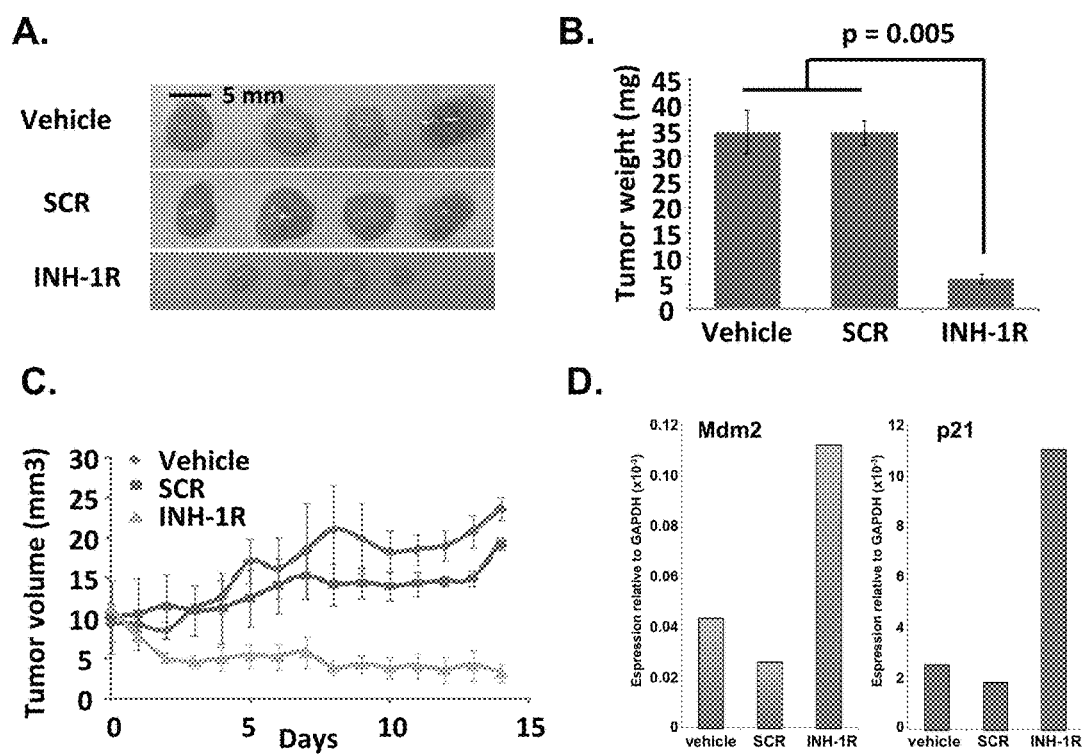

FIG. 12 shows that INH-1R CPP limits tumor proliferation in vivo. A. Images of the xenografts from mice (n=3 for each group, one mouse had 2 xenografts) treated with INH-1R CPP, a scrambled peptide control, or vehicle for 14 days. B. Tumors of mice treated with INH-1R CPP were six times smaller compared to controls as evaluated by weight. C. Tumor volume was estimated daily. D. Residual tumors from INH-1R CPP treated animals showed up-regulation of the p53 target genes MDM2 and p21.

Figure 13:
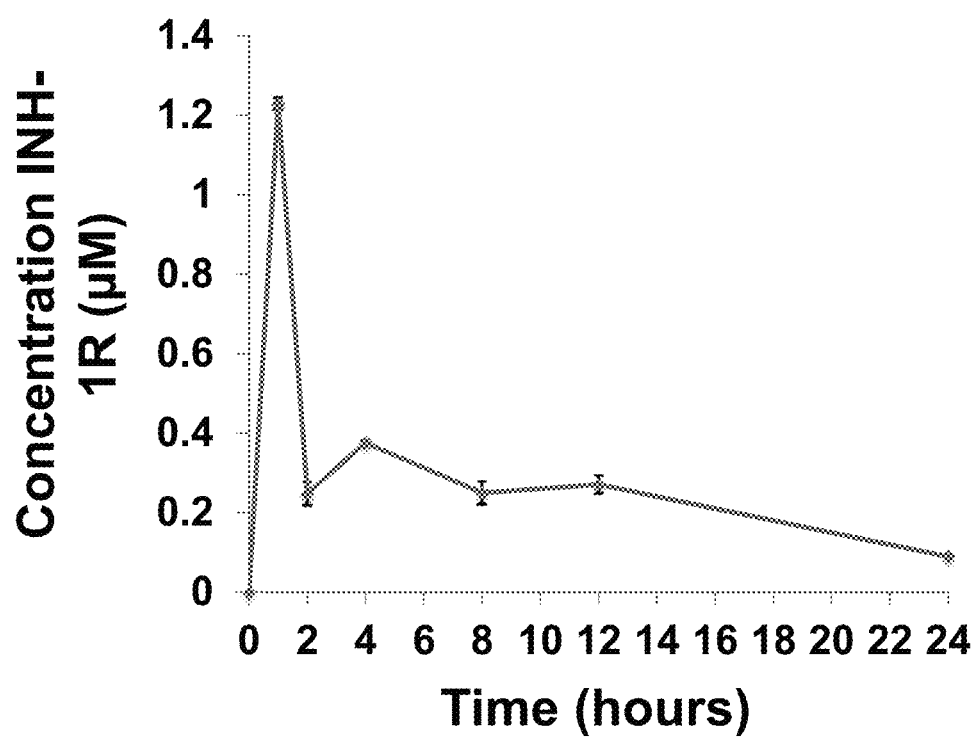

FIG. 13 shows serum concentration of INH-1R CPP as measured by MRM (Multiple Reaction Monitoring) mass spectrometry. Nude mice were injected in the flank with OVCAR-3 cells and the resulting xenografts were allowed to grow for two weeks. The mice were then treated for three days via IP with 15 mg/kg of INH-1R CPP peptide or scrambled control peptide. They were divided in groups of two and sacrificed at 1, 2, 4, 8, 12 and 24 hours post final peptide injection. Two naïve mice were sacrificed before treatment to obtain a reference value. Peak serum concentration of INH-1R CPP (as well as control peptide) was detected at 1 hour post injection. Average of two mice are shown.

DESCRIPTION

This application relates, e.g., to the design, synthesis and functional characterization of peptides which bind specifically (preferentially) to p53 protein molecules having an aberrant (e.g. pathological) conformation and which restore the conformation of the p53 molecules having the aberrant conformation. The aberrant conformation can be, for example, misfolding of the molecule resulting from a mutation in the molecule or other factors, or the formation of amyloid aggregates of wild type or mutant p53 molecules. As a result of the restoration of the conformation, biological or biochemical activities which were lost or inhibited as a result of the aberrant conformation are reactivated or restored. For example, the inhibitory peptides can inhibit (block) further aggregation of p53 amyloid aggregates and/or restore p53 functions such as, e.g., induction or initiation of apoptosis, inhibition of cell proliferation, and/or inducing shrinkage of a tumor. In some embodiments, the peptides are fused to cell penetrating peptides (CPP) which enhance their delivery into cells.

The present inventors recently showed that it is possible to efficiently arrest the aggregation of the Alzheimer's Disease related protein Tau and the semen-derived enhancer of HIV virus infection (SEVI) utilizing short amino-acid inhibitors designed to specifically "cap" the growing aggregates (Sievers et al., 2011). Accordingly, there is a new therapeutic window which targets a completely unexplored aspect of p53 biology that seems to have profound effects on cancer progression, i.e. p53 misfolding resulting in aggregation. The inventors hypothesized that mutations, overexpression or other cellular factors can destabilize the native p53 structure, exposing an adhesive, "steric-zipper" segment, proposed as the basic building block of amyloid aggregates (Nelson et al., Nature, 2005, Sawaya et al., Nature, 2007). As reported herein, the inventors therefore obtained high atomic resolution views of the amyloid spine of p53 aggregates, and used them as a template to develop structure based peptide inhibitors that can cap the aggregates, inhibit further p53 aggregation and therefore generate a pool of active p53 that can sensitize the cancer cells to treatment and induce or initiate apoptosis. These rational structure-based inhibitors of p53 aggregation provide a new chemotherapy efficient toward those tumors that have proven to be the most aggressive and resilient to standard treatment, due to p53 aggregation status (Xu et al., 2011; Levy et al. 2011).

This application relates, e.g., to such inhibitory peptides; molecules in which an inhibitory peptide of the invention is fused to a cell penetrating peptide (CPP), which fusion molecules are sometimes referred to herein as "CPP inhibitors"; pharmaceutical compositions comprising an inhibitory peptide or a CPP inhibitor of the invention and a pharmaceutically acceptable carrier; methods of using the inhibitory peptides or the CPP inhibitors to restore the structure and function of p53 molecules having an aberrant conformation, e.g. (a) to block or inhibit p53 aggregation (e.g., to delay the onset of aggregation and/or to lower the amount of aggregates, in solution, in a cell, or in a subject having a cancer or tumor that comprises p53 aggregates)

and/or (b) to restore the folding of a misfolded p53, thereby re-activating a biological or biochemical activity of p53 due to the aberrant conformation; methods for treating a subject having a tumor which comprises aggregated p53 (e.g., either wild type or mutant aggregated p53), comprising administering to the subject or contacting the tumor with an effective amount of a CPP inhibitor of the invention; and computer-related embodiments, such as a method for designing and obtaining inhibitory peptides or small molecules based on the structural representation of the crystal structures described herein.

Advantages of the inhibitory peptides and CPP inhibitors of the invention include: (1) They are selectively active only on those cancer cells containing mutant or wild type aggregated p53 or misfolded p53; (2) They show no effect on folded and active p53 (no hyper-activation or increase of p53 concentration in normal cells); (3) They are conformation specific, rather than sequence (e.g. mutation) specific. A single inhibitor will work for different aggregating mutants as well as for wild type p53; (4) They can block co-aggregation of wild-type p53 as well as aggregation of p53 with homologues and other proteins including, for example, p63 and p'73, the other members of the p53 family of proteins (Xu et al, 2011); (5) Cell penetration and protein stability are not challenging obstacles, thanks to their composition and small size; (6) They are unexpectedly stable: they are not proteolyzed and exhibit a sufficiently long half-life to function in vivo (e.g. in a body).

One aspect of the invention is an inhibitory peptide (e.g., an isolated peptide) represented by the consensus sequence [L,Y,E,W] T [R,K], I T [L,Y] E (SEQ ID NO: 1), or an active variant thereof. In one embodiment, the inhibitory peptide is represented by the consensus sequence [L,Y,E,W] T R I T [L,Y] E (SEQ ID NO: 3), or an active variant thereof. The inhibitory peptide may consist of the consensus sequence [L,Y,E,W] T [R,K], I T [L,Y] E (SEQ ID NO: 1), or it may consist of the consensus sequence [L,Y,E,W] T R I T [L,Y] E (SEQ ID NO: 3). In embodiments of the invention, the inhibitory peptide may consist of, or comprise, any of the inhibitory peptide sequences listed in Table 1. That is, the peptide may be LTRITLE (SEQ ID NO: 4), YTRITLE (SEQ ID NO: 5), ETRITLE (SEQ ID NO: 6), LTRIYLE (SEQ ID NO: 7), YTRIYLE (SEQ ID NO: 8), WTRITLE (SEQ ID NO: 9), WTRIYLE (SEQ ID NO: 10), ETRIYLE (SEQ ID NO: 11), LTKITLE (SEQ ID NO: 12), YTKITLE (SEQ ID NO: 13), WTKITLE (SEQ ID NO: 14), ETKITLE (SEQ ID NO: 15), LTKIYLE (SEQ ID NO: 16), YTKIYLE (SEQ ID NO: 17), WTRIYLE (SEQ ID NO: 10), ETKIYLE (SEQ ID NO: 18). Inhibitory peptides having the preceding sequences, including the active variants, are sometimes referred to herein as "inhibitory peptides of the invention."

Another aspect of the invention is a CPP inhibitor which comprises an inhibitory peptide of the invention (including active variants) which is fused (linked, associated with, coupled), optionally via a linker sequence, to a cell penetrating peptide (CPP). The peptide can be fused the CPP in any of a variety of ways (e.g. chemically coupled, or fused via a peptide bond or other conventional means of chemical coupling).

In one embodiment, the CPP is represented by the consensus sequence $(R_{1-16})$ P I [L,Y,E,W] T [R,K], I T [L,Y] E (SEQ ID NO: 19), or an active variant thereof. CPP inhibitors which comprise sequences encompassed by this consensus sequence or active variants thereof are sometimes referred to herein as "CPP inhibitors of the invention."

Another aspect of the invention is a pharmaceutical composition comprising an inhibitory peptide or CPP of the invention and a pharmaceutically acceptable carrier. Such pharmaceutical compositions are sometimes referred to herein as "pharmaceutical compositions of the invention."

As used herein, the singular forms "a," "an," and "the" include plural referents unless the context clearly dictates otherwise. For example, in the preceding case, the pharmaceutical composition may comprise one or more inhibitory peptide molecules or CPPs of the invention, which can be the same or different.

Another aspect of the invention is a complex comprising a p53 protein molecule and an inhibitory peptide or CPP of the invention. They may be bound to, conjugated with, or otherwise associated with each other. The p53 and the inhibitory peptide or CPP may be covalently or non-covalently linked.

Another aspect of the invention is a method for restoring the conformation of a p53 protein molecule having an aberrant conformation (e.g. wherein the aberrant conformation is responsible, at least in part, for a loss of a function of the protein), comprising
  contacting the p53 molecule having the aberrant conformation with an effective amount of an inhibitory peptide or a CPP inhibitor of the invention,
  the contacted p53 having a restored conformation,
  wherein the p53 molecule having the restored conformation exhibits an activity (e.g. a restored activity) selected from the induction of apoptosis, inhibition of cell proliferation and/or induction of shrinkage of a tumor.

In one embodiment of this method, the p53 protein molecule which is contacted is in a subject having cancer, and the p53 molecule having the restored conformation inhibits proliferation of cancer cells in the subject and/or induces shrinkage of a tumor in the subject.

Another aspect of the invention is a method for preventing and/or inhibiting cell proliferation (e.g. proliferation of cancer cells) resulting from (e.g. caused by) p53 with an aberrant conformation, comprising contacting the cell with an effective amount of an inhibitory peptide or a CPP inhibitor of the invention or with a pharmaceutical composition comprising an inhibitory peptide or a CPP inhibitor of the invention.

Another aspect of the invention is a method for treating a subject having a cancer associated with (e.g. mediated by) p53 having an aberrant conformation, comprising administering to the subject an effective amount of a pharmaceutical composition of the invention, thereby inhibiting proliferation of cancer cells in the subject and/or shrinking a tumor in the subject.

Another aspect of the invention is a method for treating a subject that has a mutant gene encoding p53 and therefore a susceptibility to develop cancers (e.g., Li-Fraumeni syndrome), comprising administering to the subject a dose (e.g. a plurality of doses, such as by a plurality of injections) comprising in total an effective amount of a pharmaceutical composition of the invention, thereby reducing or preventing the development of tumors in the subject.

Another aspect of the invention is a computer-implemented method for identifying an inhibitory peptide that inhibits aggregation of p53, comprising the steps of:
  identifying a template peptide sequence comprising a zipper-forming sequence of the p53 segments TIITLE (SEQ ID NO: 20) or LTIITLE (SEQ ID NO: 21) or a mirror of the zipper forming sequence from the target polypeptide, wherein the zipper-forming sequence aggregates into a steric zipper;
  designing on a computer at least one complementary peptide sequence that forms favorable steric and energetic intermolecular interactions with the template peptide sequence, wherein the interactions occur at one or both of the upper or lower ends of the steric zipper; and identifying a candidate inhibitory peptidic compound selected from the group consisting of the complementary sequence, a mirror of the complementary sequence, a peptide mimetic of the complementary sequence and a peptide mimetic of the mirror of the complementary sequence.

Another aspect of the invention is a kit comprising an inhibitory peptide or CPP inhibitor of the invention, optionally packaged in a container.

Another aspect of the invention is a method for making an inhibitory peptide of the invention, comprising synthesizing it chemically or producing it recombinantly.

As described in the Examples herein, based on the determination of the atomic structure of a fiber forming segment of p53, the inventors have designed a series of peptide inhibitors which diminish p53 aggregation. The inventors designed peptidic inhibitors to specifically "cap" the growing aggregates of p53.

Figure 1:
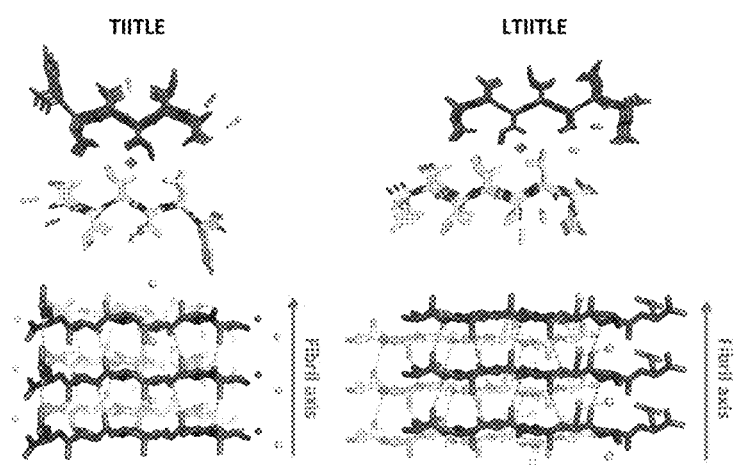
FIG. 1 shows the X-ray high-resolution structures of two polymorphs of the amyloid aggregation prone segment of p53, namely p53 residues 253-258 (sequence: TIITLE (SEQ ID NO: 20)) and p53 residues 252-258 (sequence: LTIITLE (SEQ ID NO: 21)). In both cases, the protofilaments consist of two interdigitated beta sheets, with a tight, dry interface. Three layers of the sheets are shown; water molecules are shown as yellow spheres. The top view is down the fiber axis (indicated as a red diamond) while the bottom view is perpendicular to the axis (red arrow)

Using the ZipperDB algorithm (Goldschmidt et al. 2010), the inventors identified crystallizable amyloid-forming segments. The inventors chemically synthesized the p53$_{252-258}$ and p53$_{253-258}$ segments, crystallized them and determined their three-dimensional structures by micro-crystallography (FIG. 1). The structures displayed a typical steric zipper architecture, with parallel in-register β-strands and β-sheets interdigitating via hydrophobic side chains in a "face-to-back" (for p53$_{252-258}$) and "face-to-face" (for p53$_{253-258}$) orientation (Sawaya et al, Nature, 2007).

The inventors applied their Rosetta-based method (Sievers et al, Nature, 2011) to design inhibitors that disrupt p53 aggregation, using the p53$_{252-258}$ structure as a template. In other embodiments of the invention, the p53$_{253-258}$ structure is used as a template to design inhibitors.

Table 1 shows a list of 16 representative inhibitor sequences obtained by this method.

TABLE 1

List of designed inhibitors of amyloidogenic p53 aggregation including peptide sequences.

| Name | Inhibitor sequence | CPP inhibitor |
|---|---|---|
| INH-1R | LTRITLE | RRRRRRRRRRPILTRITLE |
| INH-2R | YTRITLE | RRRRRRRRRRPIYTRITLE |
| INH-3R | ETRITLE | RRRRRRRRRRPIETRITLE |
| INH-4R | LTRIYLE | RRRRRRRRRRPILTRIYLE |
| INH-5R | YTRIYLE | RRRRRRRRRRPIYTRIYLE |
| INH-6R | WTRITLE | RRRRRRRRRRPIWTRITLE |
| INH-7R | WTRIYLE | RRRRRRRRRRPIWTRIYLE |
| INH-8R | ETRIYLE | RRRRRRRRRRPIETRIYLE |
| INH-1K | LTKITLE | RRRRRRRRRRPILTKITLE |
| INH-2K | YTKITLE | RRRRRRRRRRPIYTKITLE |
| INH-3K | WTKITLE | RRRRRRRRRRPIWTKITLE |
| INH-4K | ETKITLE | RRRRRRRRRRPIETKITLE |
| INH-5K | LTKIYLE | RRRRRRRRRRPILTKIYLE |
| INH-6K | YTKIYLE | RRRRRRRRRRPIYTKIYLE |

TABLE 1-continued

List of designed inhibitors of amyloidogenic p53 aggregation including peptide sequences.

| Name | Inhibitor sequence | CPP inhibitor |
|---|---|---|
| INH-7R | WTRIYLE | RRRRRRRRRRPIWTRIYLE |
| INH-8K | ETKIYLE | RRRRRRRRRRPIETKIYLE |

INH-1R is the first sequence designed. INH-1R and all the other variants were synthesized fused to a poly-Arginine tag as cell penetrating peptide (CPP) and a short linker (sequence: RPI) derived from the endogenous p53 protein sequence. The inhibiting designed sequences are indicated with bold type, while the poly-Arginine tag and linker are in normal type.

The inhibitor sequences in Table 1 are, reading from top to bottom of the second column of the table, SEQ ID NO: 4 to SEQ ID NO: 17, 10 and 18. The CPP inhibitor sequences are, reading from top to bottom of the third column of the table, SEQ ID NO: 22 to SEQ ID NO: 35, 28 and 36.

Peptide inhibitors of the invention bind specifically (selectively, preferentially) to p53 having an aberrant conformation (e.g. aggregated as amyloid fibrils or fibers, or partially or completely unfolded or misfolded), in comparison to binding to other protein targets (unintended targets), such as non-aggregated or folded p53 molecules which exhibit one or more of the p53-mediated functions described herein. In fact, no binding can be detected between the peptide inhibitors of the invention and non-aggregated or folded p53 molecules.

Other suitable peptide variants include, e.g., Leu-His-Arg-Ile-Tyr-Leu-Glu (SEQ ID NO: 37) and Leu-Tyr-Ile-Arg-Ile-Leu-Arg (SEQ ID NO: 38).

On the basis of this structural analysis, one consensus sequence, taking into account the 16 sequences shown in Table 1, is [L,Y,E,W] T [R,K], I T [L,Y] E (SEQ ID NO: 1). In another embodiment, the consensus sequence is [L,Y,E,W] T R I T [L,Y] E (SEQ ID NO: 3). Residues #1, 6 and, to a lesser extent, #3 have the least contact with the template structure and are thus the most variable of the 7 residues.

Active variants of the sequences described above are also included. These are variants which retain the properties of the inhibitory peptides described herein (e.g., the ability to bind specifically to aggregated p53 in a conformation-dependent, sequence-independent manner; to inhibit fibrillation of p53 to p53 or other proteins; to inhibit proliferation of cells, including cancer cells, e.g. in solution or in cells in culture or in a subject; the ability to induce or initiate apoptosis; or the ability to shrink a tumor). Fibrillation, as used herein, refers to the formation of fiber or fibrils, such as amyloid fibrils.

Suitable active variants include peptidomimetic compounds (any compound containing non-peptidic structural elements that is capable of mimicking the biochemical and/or biological action(s) of a natural mimicked peptide, including, for example, those designed to mimic the structure and/or binding activity (such as, for example, hydrogen bonds and hydrophobic packing interactions) of the peptides according to the methods disclosed herein). Inhibitory peptides or CPP inhibitors of the invention, including active variants thereof, are sometimes referred to herein as "peptidic compounds" or "compounds."

In one embodiment, active variants of the inhibitory peptides are shortened by 1-3 (e.g., 1, 2 or 3) amino acids at either the N-terminus, the C-terminus, or both of the starting inhibitory peptide. In another embodiment, the active variants are lengthened (extended) by 1, 2, 3 or 4 amino acids at the C-terminal end of the starting inhibitory peptide.

A variety of other types of active variants are encompassed. In some embodiments, amino acids other than the ones noted above in the consensus sequence are substituted. These amino acids can help protect the peptide inhibitors against proteolysis or otherwise stabilize the peptides, and/or contribute to desirable pharmacodynamic properties in other ways. In some embodiments, the non-natural amino acids allow an inhibitor to bind more tightly to the target because the side chains optimize hydrogen bonding and/or apolar interactions with it. In addition, non-natural amino acids offer the opportunity of introducing detectable markers, such as strongly fluorescent markers which can be used, e.g., to measure values such as inhibition constants. Also included are peptide mimetics, such as, e.g., peptoids, beta amino acids, N-ethylated amino acids, and small molecule mimetics.

In one embodiment, non-natural amino acids are substituted for amino acids in the sequence. More than 100 non-natural amino acids are commercially available. These include, for example, Non-Natural Amino Acids which can Substitute for LEU:

| | |
|---|---|
| Fmoc-L-cyclohexylglycine | 161321-36-4 |
| Fmoc-L-phenylglycine | 102410-65-1 |
| Fmoc-4-hydroxy-D-phenylglycine | 178119-93-2 |
| Fmoc-L-α-t-butylglycine | 132684-60-7 |
| Fmoc-cyclopentyl-Gly-OH | 220497-61-0 |
| Fmoc-L-2-indanylglycine | 205526-39-2 |

Non-Natural Amino Acids which can Substitute for THR:

| | |
|---|---|
| Fmoc-Thr(tBu)-OH | 71989-35-0 |
| Fmoc-(RS)-2-amino-3-hydroxy-3-methylbutanoic acid | 105504-72-1 |

Non-Natural Amino Acids which can Substitute for ILE:

| | |
|---|---|
| Fmoc-allo-Ile-OH | 251316-98-0 |
| Boc-N-Me-allo-Ile-OH | 136092-80-3 |
| Fmoc-Homoleu-OH | 180414-94-2 |

Non-Natural Amino Acids which can Substitute for GLU:

| | |
|---|---|
| Fmoc-γ-carboxy-L-glutamic acid | 111662-64-7 |
| Fmoc-L-α-aminosuberic acid | 218457-76-2 |

Non-Natural Amino Acids which can Substitute for ARG:

| | |
|---|---|
| Fmoc-Nω-nitro-L-arginine | 58111-94-7 |
| Fmoc-L-citrulline | 133174-15-9 |

Non-Natural Amino Acids which can Substitute for TYR:

| | |
|---|---|
| Fmoc-3-amino-L-tyrosine | 726181-70-0 |
| Fmoc-3-nitro-L-tyrosine | 136590-09-5 |
| Fmoc-3-methoxy-L-tyrosine | |
| Fmoc-3-iodo-L-tyrosine | 134486-00-3 |
| Fmoc-3-chloro-L-tyrosine | 478183-58-3 |
| Fmoc-3,5-dibrimo-L-tyrosine | 201484-26-6 |

Non-Natural Amino Acids which can Substitute for LYS:

| | |
|---|---|
| Fmoc-Lys(retro-Abz-Boc)-OH | 159322-59-5 |
| Fmoc-Lys(Mca)-OH | 386213-32-7 |
| Fmoc-(Nδ-4-methyltrityl)-L-ornithine | 343770-23-0 |
| N-α-Fmoc-N-ε-(d-Biotin)-L-lysine | 146987-10-2 |

In another embodiment, one or more (e.g. 1, 2, 3, 4, 5, 6, or 7) of the L-amino acids are substituted with a D amino acid.

In another embodiment, one or more (e.g. 1, 2, 3, 4, 5, 6, or 7) N-methylated residues are included in the peptide. Some representative such peptides include, e.g.,

```
                                   (SEQ ID NO: 39)
   Leu-Thr-(Nme)Arg-Ile-Tyr-Leu-Glu (SEQ ID NO: 40)
   Leu-Thr-Arg-Ile-(Nme)Tyr-Leu-Glu (SEQ ID NO: 41)
   Leu-Thr-Arg-Ile-Tyr-(Nme)Leu-Glu (SEQ ID NO: 42)
   Leu-Thr-Arg-(Nme)Ile-Tyr-Leu-Glu
```

An inhibitory peptide of the invention can comprise, e.g., L-amino acids, D-amino acids, non-natural amino acids, or combinations thereof.

In one embodiment, the inhibitor is a small molecule which has been designed by the methods described by Jiang et al. eLife 2013 (which is incorporated herein by reference, particularly with regard to this method), using the atomic structure of one of the fiber forming segments of p53 described herein as the basis for designing the inhibitor. Suitable small molecules that can be identified by this method of Jiang et al. will be evident to a skilled worker.

In one embodiment of the invention, a peptide of the invention is modified so that 1, 2 or 3 of its amino acids are substituted with an amino acid having a non-naturally occurring side chain, such as the non-natural amino acids discussed above, or with an amino acid having a side chain modified by cross-linking (e.g., through the epsilon amino group of a Lys residue) of a small molecule which has been designed by Jiang et al. eLife 2013. Some representative fiber-binding molecules are shown below. These active variants not only cap growing aggregates of p53 but also, via the modified side chains, bind to (clamp against) the sides of the steric zipper, thereby enhancing the inhibitory activity of the peptide.

Fiber-binding compounds designed by Jiang et al. eLife 2013 include:

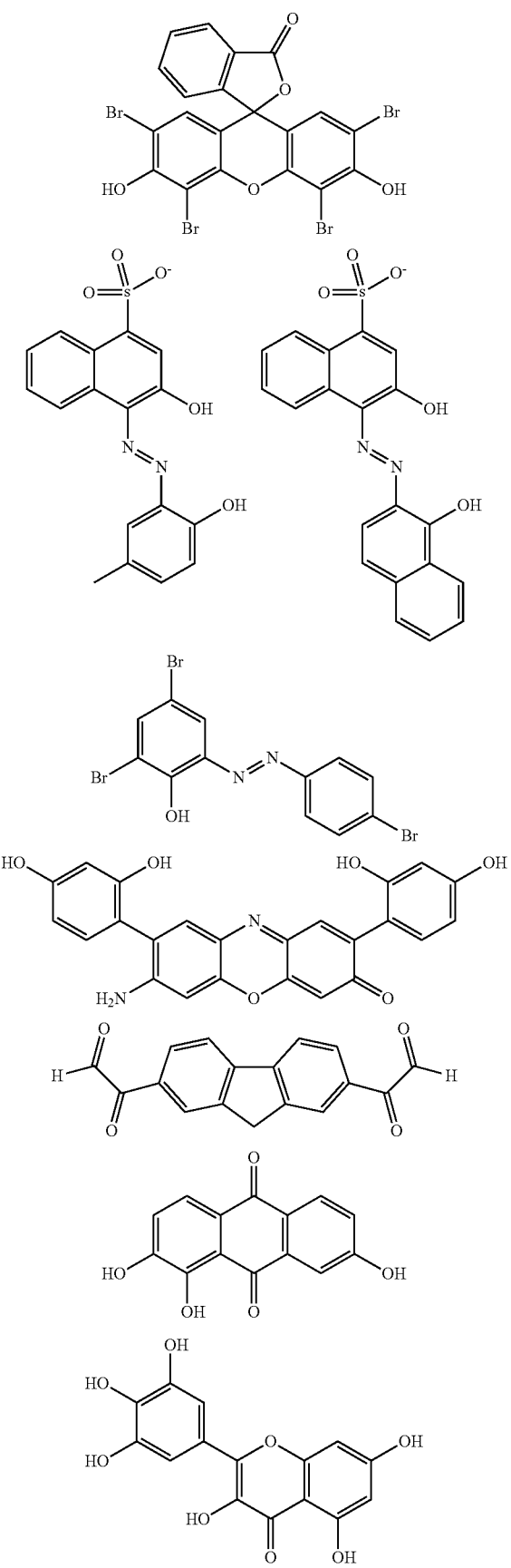
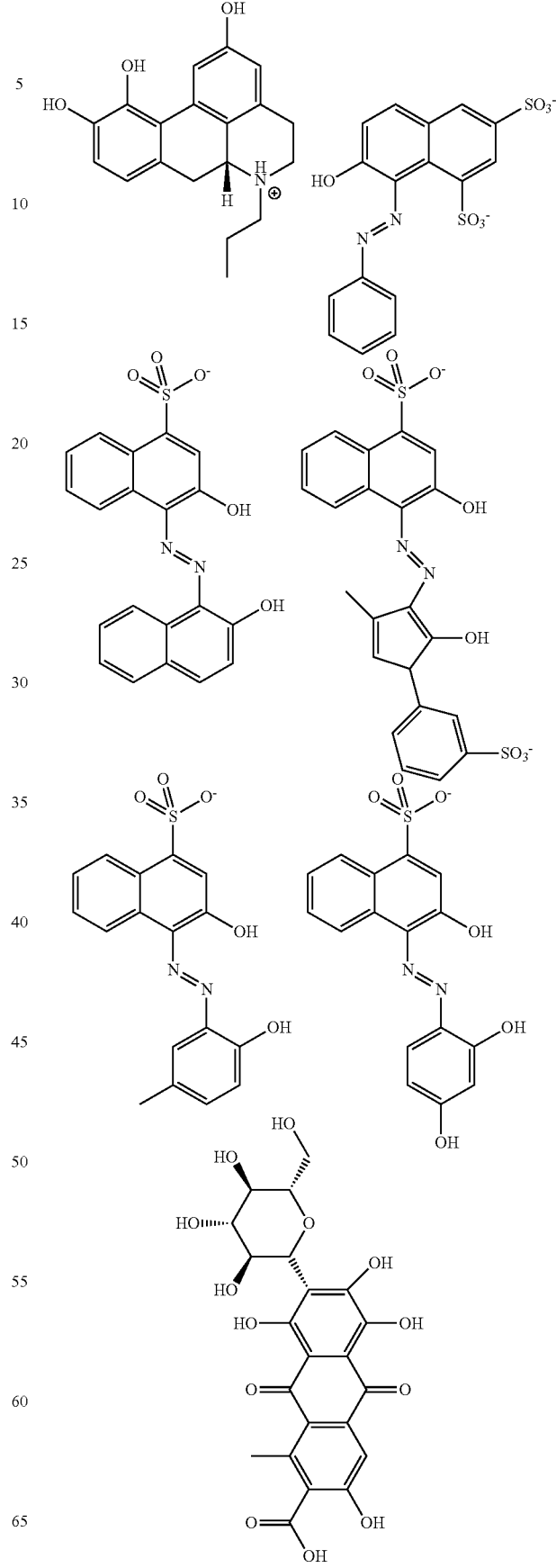

To enhance the cell permeability of inhibitory peptides of the invention, they can be fused to any of a variety of cell penetrating peptides (CPP's). CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPP's are the hydrophobic peptides, containing only apolar residues, with low net charge or have hydrophobic amino acid groups that are crucial for cellular uptake. Some typical CPP's that can be fused to an inhibitory peptide of the invention are provided in Table 2.

TABLE 2

| Name | Sequence |
|---|---|
| Reference - original or review | |
| polyARG | nR where 4 < n < 17 (e.g., n = 5, 6,7, 8, 9, 10, 11, 12, 13, 14, 15 or 16) (SEQ ID NO: 43) |

Wender, P. A., Mitchell, D. J., Pattabiraman, K., Pelkey, E. T., Steinman, L., and Rothbard, J. B. (2000). The design, synthesis, and evaluation of molecules that enable or enhance cellular uptake: peptoid molecular transporters. Proc. Natl. Acad. Sci. U.S.A. 97, 13003-8.

| Name | Sequence |
|---|---|
| polyLYS | nK where 4 < K < 17 (e.g., K = 5, 6, 7, 8, 9, 10, 11, 12, 13, 14, 15 or 16) (SEQ ID NO: 44) |
| D-polyARG | nR where 4 < n < 17 (e.g., n = 5, 6, 7, 8, 9, 10, 11, 12, 13, 14, 15 or 16) |
| D-polyLYS | nK where 4 < K < 17 (e.g., K = 5, 6, 7, 8, 9, 10, 11, 12, 13, 14, 15 or 16) |
| SynB1 | RGGRLSYSRRRFSTSTGR (SEQ ID NO: 45) |
| SynB3 | RRLSYSRRRF (SEQ ID NO: 46) |
| Penetratin | RQIKIWFQNRRMKWKK (SEQ ID NO: 47) |

Derossi, D., Joliot, A. H., Chassaing, G., and Prochiantz, A. (1994). The third helix of the Antennapedia homeodomain translocates through biological mem-branes. J. Biol. Chem. 269, 10444-50.

| Name | Sequence |
|---|---|
| PenArg | RQIRIWFQNRRMRWRR (SEQ ID NO: 48) |
| PenLys | KQIKIWFQNKKMKWKK (SEQ ID NO: 49) |
| TatP59W | GRKKRRQRRRPWQ (SEQ ID NO: 50) |
| Tat (48-60) | GRKKRRQRRRPPQ (SEQ ID NO: 51) |

Vives, E., Brodin, P., and Lebleu, B. (1997). A truncated HIV-1 Tat protein basic domain rapidly translocates through the plasma membrane and accumulates in the cell nucleus. J. Biol. Chem. 272, 16010-7.

| Name | Sequence |
|---|---|
| R9-Tat | GRRRRRRRRRPPQ (SEQ ID NO: 52) |

Futaki, S. (2002) Arginine-rich peptides: potential for intracellular delivery of macromolecules and the mystery of the translocation mechanisms. Int. J. Pharm. 245, 1-7.

| Name | Sequence |
|---|---|
| Tat | YGRKKRRQRRR (SEQ ID NO: 53) |

Vives, E., Brodin, P., and Lebleu, B. (1997). A truncated HIV-1 Tat protein basic domain rapidly translocates through the plasma membrane and accumulates in the cell nucleus. J. Biol. Chem. 272, 16010-7.

| Name | Sequence |
|---|---|
| D-Tat | GRKKRRQRRRPPQ (SEQ ID NO: 51) |

Futaki, S. (2002) Arginine-rich peptides: potential for intracellular delivery of macromolecules and the mystery of the translocation mechanisms. Int. J. Pharm. 245, 1-7.

| Name | Sequence |
|---|---|
| BMVGag(7-25) | KMTRAQRRAAARRNRWTAR (SEQ ID NO: 54) |

Futaki, S. (2002) Arginine-rich peptides: potential for intracellular delivery of macromolecules and the mystery of the translocation mechanisms. Int. J. Pharm. 245, 1-7.

| Name | Sequence |
|---|---|
| FHVCoat(35-49) | RRRRNRTRRNRRRVR (SEQ ID NO: 55) |

Futaki, S. (2002) Arginine-rich peptides: potential for intracellular delivery of macromolecules and the mystery of the translocation mechanisms. Int. J. Pharm. 245, 1-7.

| Name | Sequence |
|---|---|
| HTLV-II Rex(4-16) | TRRQRTRRARRNR (SEQ ID NO: 56) |

Futaki, S. (2002) Arginine-rich peptides: potential for intracellular delivery of macromolecules and the mystery of the translocation mechanisms. Int. J. Pharm. 245, 1-7.

| Name | Sequence |
|---|---|
| P22 N-(14-30) | NAKTRRHERRRKLAIER (SEQ ID NO: 57) |
| pVEC | LLIILRRRIRKQAHAHSK (SEQ ID NO: 58) |

Elmquist, A., Lindgren, M., Bartfai, T., and Langel, U. (2001). VE-cadherin-derived cell-penetrating peptide, pVEC, with carrier functions. Exp. Cell Res. 269, 237-44.

| Name | Sequence |
|---|---|
| Transportan | GWTLNSAGYLLGKINLKALAALAKKIL (SEQ ID NO: 59) |

TABLE 2-continued

| Name | Sequence |
|---|---|

Pooga, M., Hallbrink, M., Zorko, M., and Langel, Ü. (1998). Cell penetration by transportan. FASEB J. 12, 67-77.

| TP10 | AGYLLGKINLKALAALAKKIL (SEQ ID NO: 60) |
|---|---|

Soomets, U., Lindgren, M., Gallet, X., Hallbrink, M., Elmquist, A., Balaspiri, L., Zorko, M., Pooga, M., Brasseur, R., and Langel, Ü. (2000). Dele-tion analogues of transportan. Biochim. Biophys. Acta 1467, 165-76.

| PTD-4 | PIRRRKKLRRLK (SEQ ID NO: 61) |
|---|---|
| PTD-5 | RRQRRTSKLMKR (SEQ ID NO: 62) |
| Pep-1 | ac-KETWWETWWTEWSQPKKKRKV-cya (SEQ ID NO: 63) |
| Pep-2 | ac-KETWFETWFTEWSQPKKKRKV-cya (SEQ ID NO: 64) |

Morris, MC, Chaloin, L, Choob, M, Archdeacon, J, Heitz, F and Divita, G (2004). Combination of a new generation of PNAs with a peptide-based carrier enables efficient targeting of cell cycle progression. Gene Ther 11: 757-764.

| Pep-3 | ac-KWFETWFTEWPKKRK-cya (SEQ ID NO: 65) |
|---|---|

Morris, MC, Gros, E, Aldrian-Herrada, G, Choob, M, Archdeacon, J, Heitz, F et al. (2007). A non-covalent peptide-based carrier for in vivo delivery of DNA mimics. Nucleic Acids Res 35: e49.

| E N(1-22) | MDAQTRRRERRAEKQAQWKAAN (SEQ ID NO: 66) |
|---|---|
| B 21 N-(12-29) | TAKTRYKARRAELIAERR (SEQ ID NO: 67) |
| U2AF(142-153) | SQMTRQARRLYV (SEQ ID NO: 68) |
| PRP6(129-144) | TRRNKRNRIQEQLNRK (SEQ ID NO: 69) |
| MAP | KLALKLALKLALALKLA (SEQ ID NO: 70) |
| SBP | MGLGLHLLVLAAALQGAWSQPKKKRKV (SEQ ID NO: 71) |
| FBP | GALFLGWLGAAGSTMGAWSQPKKKRKV (SEQ ID NO: 72) |
| MPG | ac-GALFLGFLGAAGSTMGAWSQPKKKRKV-cya (SEQ ID NO: 73) |

Morris, MC, Vidal, P, Chaloin, L, Heitz, F and Divita, G (1997). A new peptide vector for efficient delivery of oligonucleotides into mammalian cells. Nucleic Acids Res 25: 2730-2736.

| MPG(ΔNLS) | ac- GALFLGFLGAAGSTMGAWSQPKSKRKV-cya (SEQ ID NO: 74) |
|---|---|
| REV(34-50) | TRQARRNRRRWRERQR (SEQ ID NO: 75) |

Futaki, S. (2002) Arginine-rich peptides: potential for intracellular delivery of macromolecules and the mystery of the translocation mechanisms. Int. J. Pharm. 245,1-7.
ACPPs from Jiang et al., PNAS 2004 - lower case indicates D-aa. The symbol "__" in some of these sequences indicates a position at which any of a variety of art-recognized protease cleavage sites can be inserted:

EEEEEDDDDK_AXRRRRRRRRRXC (SEQ ID NO: 76)

EEEEEDDDDK_ARRRRRRRRRXC (SEQ ID NO: 77)

EDDDDK_AXRRRRRRRRRXC (SEQ ID NO: 78)

EEDDDDK_ARXRRXRRXRRXRXC (SEQ ID NO: 79)

DDDDDDK_ARRRRRRRRRXC (SEQ ID NO: 80)

EEDDDDK_AXrrrrrrrrrXC:

eeeeeeXPLG_LAGrrrrn-rrrXc eeeeeeXPLG_LAGrrn-rrrrrXc

UeeeeeeeeXPLG_LAGrrrrrrrrrXk eeeeeeXPLG_LAGrrn-rrrrrXc

UeeeeeeXPLG_LAGrrrrrrrrrXc

UeeeeeeeeXPLG_LAGrrrrrrrrrXk

[11-kDa PEG]XeeeeeeeeeXPLG_LAGrrrrrrrrrXk

[11-kDa PEG]XeeeeeeeeeXLALGPGrrrrrrrrrXk

TABLE 2-continued

| Name | Sequence |
|---|---|
| F1-XrrrrrrrrrrXPLG_LAGeeeeeee | |
| F1-XrrrrrrrrrrXSGRS_Aeeeeeeee | |
| eeeeeeXSGRS_AXrrrrrrrrrrXc | |
| F1-rrrrrrrrrc-_-ceeeeee | |

In another embodiment, the CPP is polyD$_{(1-16)}$.

In general, it is advisable that the length of the CPP is rather short, e.g. less than about 30 amino acids, in order to improve stability and pharmacodynamic properties once the molecule enters a cell.

In some embodiments, the CPP is directly attached (fused) to a peptide of the invention. In other embodiments, it is desirable to separate the highly charged CPP from the inhibitor peptide with a linker, to allow the inhibitor to retain its activity. Any of a variety of linkers can be used. The size of the linker can range, e.g., from 1-7 or even more amino acids (e.g., 1, 2, 3, 4, 5, 6 or 7 amino acids). In some embodiments, the linker has sequences from the endogenous p53 sequence. For example, the linker can be GGMNRRPI (SEQ ID NO: 81), or a truncated version thereof having 1, 2, 3, 4 or 5 of the contiguous amino acids N-terminal to RPI fused to the inhibitory peptide. The RPI linker used in the experiments described herein is one such linker.

In some embodiments of the invention, the CPP inhibitor is further modified in order to target specific cancer types specifically. For example, (1) One embodiment is a modification of the approach described by Roger Tsien and coworkers (Olson et al, PNAS 2010) using ACPPs, activatable CPPs that can only enter a cell after a proteolytic cleavage by a cancer specific protease. In this embodiment, an inhibitor is targeted to a specific cancer type by utilizing a sequence that is specific for those proteases primarily expressed by the cancer of interest.

(2) Another embodiment is a modification of the strategy proposed by Hatakeyama and colleagues (Hatakeyama et al, PNAS 2011). These authors obtained targeted cancer cell delivery using the carbohydrate mimetic peptide IF7 (sequence IFLLWQR (SEQ ID NO: 82)), which binds annexin 1, a cancer vasculature marker. In this embodiment, a suitable tumor vasculature marker binding peptide is fused it to a CPP inhibitor of the invention.

(3) In another embodiment, an inhibitor is conjugated to nanoparticle. Any of a variety of suitable nanoparticles will be evident to a skilled worker. These include, e.g., empty vault shells, liposomes, polymeric nanoparticles, dendrimers or the like.

In one embodiment of the invention, an inhibitory peptide or CPP inhibitor of the invention is isolated or purified, using conventional techniques such as the methods described herein. By "isolated" is meant separated from components with which it is normally associated, e.g., components present after the peptide is synthesized. An isolated peptide can be a cleavage product of a protein which contains the peptide sequence. A "purified" inhibitory peptide can be, e.g., greater than 90%, 95%, 98% or 99% pure.

In embodiments of the invention, the inhibitory peptide or CPP inhibitor is detectably labeled. Labeled peptides can be used, e.g., to better understand the mechanism of action and/or the cellular location of the inhibitory peptide. Suitable labels which enable detection (e.g., provide a detectable signal, or can be detected) are conventional and well-known to those of skill in the art. Suitable detectable labels include, e.g., radioactive active agents, fluorescent labels, and the like. Methods for attaching such labels to a protein, or assays for detecting their presence and/or amount, are conventional and well-known.

An inhibitory peptide or CPP inhibitor of the invention can be synthesized (e.g., chemically or by recombinant expression in a suitable host cell) by any of a variety of art-recognized methods. In order to generate sufficient quantities of an inhibitory peptide for use in a method of the invention, a practitioner can, for example, using conventional techniques, generate nucleic acid (e.g., DNA) encoding the peptide and insert it into an expression vector, in which the sequence is under the control of an expression control sequence such as a promoter or an enhancer, which can then direct the synthesis of the peptide. For example, one can (a) synthesize the DNA de novo, with suitable linkers at the ends to clone it into the vector; (b) clone the entire DNA sequence into the vector; or (c) starting with overlapping oligonucleotides, join them by conventional PCR-based gene synthesis methods and insert the resulting DNA into the vector. Suitable expression vectors (e.g., plasmid vectors, viral, including phage, vectors, artificial vectors, yeast vectors, eukaryiotic vectors, etc.) will be evident to skilled workers, as will methods for making the vectors, inserting sequences of interest, expressing the proteins encoded by the nucleic acid, and isolating or purifying the expressed proteins.

Another aspect of the invention is a pharmaceutical composition comprising one or more of the inhibitory peptides or CPP inhibitors and a pharmaceutically acceptable carrier. The components of the pharmaceutical composition may be detectably labeled, e.g. with a radioactive or fluorescent label, or with a label that is suitable for detection by positron emission spectroscopy (PET). In some embodiments, the inhibitory peptide or CPP inhibitor is present in an effective amount for the desired purpose.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use. For example, "pharmaceutically acceptable salts" of a compound means salts that are pharmaceutically acceptable, as defined herein, and that possess the desired pharmacological activity of the parent compound.

Other aspects of the invention include: a polynucleotide encoding an inhibitory peptide of the invention, optionally linked to a CPP sequence, which is optionally separated from the inhibitory peptide by a suitable linker. In embodiments of the invention, the polynucleotide is operably linked to a regulatory control sequence (e.g., a promoter or an enhancer) to facilitate production of the encoded protein following introduction (e.g. by transfection) into a suitable cell; a cell comprising the expression vector; and a method of making an inhibitory peptide of the invention comprising cultivating the cell and harvesting the polypeptide thus generated.

As used throughout this application, "about" means plus or minus 5% of a value.

Another aspect of the invention is a kit for carrying out any of the methods described herein. The kit may comprise a suitable amount of an inhibitory peptide or CPP inhibitor of the invention; reagents for generating the peptide or CPP inhibitor; reagents for assays to measure their functions or activities; or the like. Kits of the invention may comprise instructions for performing a method. Other optional elements of a kit of the invention include suitable buffers, media components, or the like; a computer or computer-readable medium providing the structural representation of one of the crystal structures described herein; containers; or packaging materials. Reagents for performing suitable controls may also be included. The reagents of the kit may be in containers in which the reagents are stable, e.g., in lyophilized form or stabilized liquids. The reagents may also be in single use form, e.g., in single reaction form for administering to a subject.

One aspect of the invention is a computer-implemented method for designing an inhibitory peptide which inhibits aggregation of p53, using a method as described herein. For example, the method can comprise identifying (e.g. with a computer) a template peptide sequence comprising a zipper-forming sequence of the p53 segments TIITLE (SEQ ID NO: 20) or LTIITLE (SEQ ID NO: 21) or a mirror of the zipper-forming sequence (wherein the zipper-forming sequence aggregates into a steric zipper); designing on a computer at least one complementary peptide sequence that forms favorable steric and energetic intermolecular interactions with the template peptide sequence, wherein the interactions occur at one or both of the upper or lower ends of the steric zipper; and identifying (e.g. with a computer) a candidate inhibitory peptidic compound selected form the group consisting of the complementary sequence, a mirror of the complementary sequence, a peptide mimetic of the complementary sequence and a peptide mimetic of the mirror of the complementary sequence. Details of this type of method are described in the patent which issued from U.S. Ser. No. 12/702,175, which is incorporated by reference herein in its entirety, particularly with regard to the method for designing an inhibitory peptidic compound which inhibits aggregation of an amyloid-forming target polypeptide of interest.

In embodiments of the invention, an inhibitory compound (e.g. a peptidic compound) designed by this method is synthesized and screened for the ability to bind to and/or to inhibit aggregation of p53, e.g., using one of the methods described herein.

Characterization of candidate inhibitory peptides or CPP inhibitors of the invention can be carried out by any of a variety of conventional methods. For example, the peptides or CPP inhibitors can be assayed for the ability to reduce or inhibit p53 aggregation or to re-activate p53. Functional p53 can then, for example, lead to apoptosis in cells. The assays can be carried out in vitro or in vivo.

Figure 3:
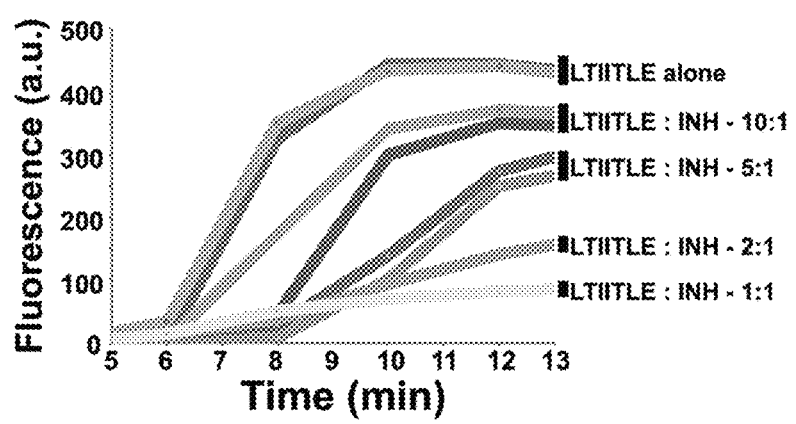
FIG. 3 shows the in vitro inhibition of p53 aggregation (segment $p53_{252-258}$) by INH-1R. The aggregation of p53 is monitored via Thioflavin T assay: an increase in Thioflavin T fluorescence is detected over time due to the formation of increasing amounts of amyloid to which the dye can specifically bind. INH-1R is added in solution at different concentrations and is able to delay the aggregation onset and lower the total amount of aggregates present, in a concentration dependent fashion. The sequence of this segment, LTIITLE, is SEQ ID NO: 21.

One representative in vitro assay is the thioflavin T assay shown in FIG. 3 (Naiki, H., Higuchi, K., Hosokawa, M., and Takeda, T. (1989) Fluorometric determination of amyloid fibrils in vitro using the fluorescent dye, thioflavine T. Anal. Biochem., 177, 244-249). The assay can be performed using a target sequence peptide, such as LTIITLE (SEQ ID NO: 21), or it can be performed using full-length p53 (such as recombinant p53). In both cases, the peptide (e.g. LTIITLE) (SEQ ID NO: 21) or the p53 is placed in solution with thioflavin T and increasing concentrations of inhibitor. The assay is performed in a multiwall plate (e.g. a 384 well plate). This dye is amyloid specific and is only fluorescent when bound to amyloid aggregates. The fluorescence is measured over time, e.g. with a plate reader. Inhibition is detected as a delay in the onset of aggregation and/or less total amount of aggregates formed.

The following assays are among the conventional functional assays which can be performed in cells:

1. Reduction in p53 Aggregation p53 aggregation is measured in cancer cells, as a measure of p53 inactivation (Xu et al, 2011; Lasagna-Reeves et al, 2013). Screens are performed for changes in the total amount of aggregates present with or without inhibitors using, e.g., one of the following conventional methods:

Immunostain of the cells using amyloid conformation specific antibodies commercially available, e.g., A11 and OC Stain of cells with amyloid specific dyes, such as Thioflavin T and Congo Red Dot blot on cell lysates using OC or A11 antibodies Native page gels coupled to western blots on cell lysates using p53 specific antibodies to check for the presence/absence of high-molecular weight p53 aggregates Immunostain of the cells using different commercially available p53 antibodies that can discriminate between abnormally or normally folded p53

2. Re-Activation of p53 Function

As mentioned, p53 function is typically inhibited by aggregation (Xu et al, 2011; Lasagna-Reeves et al, 2013). p53 inactivation and re-activation are tested in the presence of different concentrations of inhibitors with the following conventional approaches:

Restoration of p53 transcriptional activity measured by quantitating the transcripts of several p53 targets by RT-PCR or RNAseq Restoration of p53 transcriptional activity measured by detecting via Western blot several p53 targets at the protein level Ability of the inhibitor to arrest cell proliferation screening via soft agarose culture colony forming assay Ability of the inhibitor to arrest cell proliferation screening via BrdU incorporation or reduction in Ki67 stain Ability of the inhibitor to induce cell death measured via MTT or MTS assay Ability of the inhibitor to induce apoptosis measured via caspase apoptosis kit or Annexin V stain coupled to FACS Cells are treated with the inhibitors alone or in combination with traditional chemotherapy as well as other chemotherapeutic molecules such as other targeted agents against kinases or other molecules. Any of the preceding methods can further comprise testing candidate inhibitory peptides for, e.g., their ability to bind to p53, to inhibit p53 fibrillation, or to sensitize cancer cells to chemotherapy, in vitro or in vivo.

One aspect of the invention is a method for reducing or inhibiting p53 aggregation, comprising contacting p53 amyloid protofilaments with an effective amount of one or more of the inhibitory peptides of CPP inhibitors of the invention. Such a method can be carried out in vitro (in solution) or in vivo (e.g. cells in culture or in a subject).

Another aspect of the invention is a method for restoring the conformation of a p53 protein molecule having an aberrant conformation. An "aberrant conformation," as used herein, refers to a conformation which is different from the wild type conformation, and which results in a loss of function of the molecule. For example, p53 with an aberrant conformation can lose the ability to inhibit cell proliferation (e.g. of cancer cells), to induce or initiate apoptosis, or to shrink a tumor. Such aberrant conformation is sometimes referred to herein as pathological conformation. The aberrant conformation can take the form of amyloid aggregates or fibers (fibrils) of p53 molecules with other p53 molecules or with other proteins. Alternatively, the aberrant conformation can take the form of misfolding (e.g., partial or complete unfolding) of the p53 protein due to mutations or other factors. Without wishing to be bound by any particular mechanism, it is suggested that the misfolding-promoting mutations destabilize the native p53 structure causing the hydrophobic adhesive segment $p53_{252-258}$ to get solvent exposure. The segments rapidly interact with other p53 molecules resulting in protein aggregation and inactivation. It is suggested that by generating an aggregation inhibitor which blocks these segments from interacting with each other, the aggregation process is halted and/or the inhibitor also chaperones the misfolded p53 into an active conformation, thereby potentially restoring a pool of functional and soluble p53, capable of driving a cell death response.

In this method for restoring the conformation of a p53 protein having an aberrant conformation, the p53 molecule having the aberrant conformation is contacted with an effective amount of an inhibitory peptide or a CPP inhibitor of the invention. The contacted p53 molecule has a restored conformation, and exhibits a restored or reactivated biological or biochemical activity selected from, e.g., induction or initiation of apoptosis, inhibition of cell proliferation and/or shrinkage of a tumor.

Another aspect of the invention is a method for reactivating or restoring a biological or biochemical activity (function) of a p53 protein which results from aberrant conformation of the p53 protein. The method comprises contacting the p53 protein molecule having an aberrant conformation with an effective amount of an inhibitor peptide or CPP inhibitor of the invention, wherein the biological or biochemical activity of the p53 molecule is induction or initiation of apoptosis and/or is inhibition of cell proliferation and/or is inducing shrinkage of a tumor. As a result of contacting the p53 protein having the aberrant conformation, the lost biological or biochemical activity of the p53 molecule is reactivated or restored.

Another aspect of the invention is a method for inhibiting or preventing a loss of a biological or biochemical activity (function), of a p53 protein which results from aberrant conformation of the p53 protein. The method comprises contacting the p53 protein molecule having an aberrant conformation with an effective amount of an inhibitor peptide or CPP inhibitor of the invention, wherein the biological or biochemical activity of the p53 molecule is induction or initiation of apoptosis and/or is inhibition of cell proliferation and/or is inducing shrinkage of a tumor. As a result of contacting the p53 protein having the aberrant conformation, the loss of activity of the p53 molecule is inhibited or prevented.

Another aspect of the invention is a method for treating a subject having a disease or condition which is mediated by loss of function of p53, such as a cancer or a tumor in which p53 has an abnormal conformation (e.g. is aggregated or misfolded). That is, the cancer is associated with p53 having an aberrant conformation. The method comprises administering to the subject an effective amount of one or more CPPs of the invention. In some embodiments, a cocktail of one of more of the CPP inhibitors is used. In some embodiments, the CPP inhibitor is used in conjunction with a conventional chemotherapeutic drug or regimen, in order to enhance the response of the subject the chemotherapeutic drug or regimen. Typical such chemotherapeutic drugs or regimens include, e.g., paclitaxel, taxol, gemcitabine, cisplatin, carboplatin, rapamycin, doxorubicin, 5-fluorouracil, trastuzumab, imatinib, sorafenib, vemurafenib, dasatinib, crizotinib, gefitinib, erlotinib, carfilzomib, PRIMA1-MET, MI-773, nutlin, and 17AAG.

An "effective amount" of a compound or pharmaceutical composition of the invention is an amount that can elicit a measurable amount of a desired outcome, e.g. inhibition of p53 aggregation; for a diagnostic assay, an amount that can detect a target of interest, such as a p53 aggregate; or in a method of treatment, an amount that can reduce or ameliorate, by a measurable amount, a symptom of the disease or condition that is being treated.

A "subject" can be any subject (patient) having p53 with an aberrant conformation (e.g., the p53 is aggregated or misfolded), in which the condition or disease can be treated by a method of the present invention. In one embodiment of the invention, the subject has a cancer, such as one of the cancers described in Soussi et al., 2006 that are associated with mutant p53. Typical subjects include vertebrates, such as mammals, including laboratory animals, dogs, cats, non-human primates and humans.

The inhibitors of the invention can be formulated as pharmaceutical compositions in a variety of forms adapted to the chosen route of administration, for example, orally, nasally, intraperitoneally, or parenterally, by intravenous, intramuscular, topical or subcutaneous routes, or by injection into tissue.

Suitable oral forms for administering the compounds include lozenges, troches, tablets, capsules, effervescent tablets, orally disintegrating tablets, floating tablets designed to increase gastric retention times, buccal patches, and sublingual tablets.

The compounds of the invention may be systemically administered, e.g., orally, in combination with a pharmaceutically acceptable vehicle such as an inert diluent or an assimilable edible carrier, or by inhalation or insufflation. They may be enclosed in coated or uncoated hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. For compositions suitable for administration to humans, the term "excipient" is meant to include, but is not limited to, those ingredients described in Remington: The Science and Practice of Pharmacy, Lippincott Williams & Wilkins, 21st ed. (2006) (hereinafter Remington's).

The compounds may be combined with a fine inert powdered carrier and inhaled by the subject or insufflated. Such compositions and preparations should contain at least 0.1% compounds. The percentage of the compositions and preparations may, of course, be varied and may conveniently be between about 2% to about 60% of the weight of a given unit dosage form.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. A syrup or elixir may contain the active compound, sucrose or fructose as a sweetening agent, methyl and propylparabens as preservatives, a dye and flavoring such as cherry or orange flavor.

Various other materials may be present as coatings or to otherwise modify the physical form of the solid unit dosage form. For instance, tablets, pills, or capsules may be coated with gelatin, wax, shellac or sugar and the like. Of course, any material used in preparing any unit dosage form should be pharmaceutically acceptable and substantially non-toxic in the amounts employed.

In addition, the compounds may be incorporated into sustained-release preparations and devices. For example, the compounds may be incorporated into time release capsules, time release tablets, and time release pills. In some embodiments, the composition is administered using a dosage form selected from the group consisting of effervescent tablets, orally disintegrating tablets, floating tablets designed to increase gastric retention times, buccal patches, and sublingual tablets.

The compounds may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include conventional nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the compounds of formula 1 can be determined by comparing their in vitro activity, and in vivo activity in animal models. Methods for the extrapolation of effective dosages in mice, and other animals, to humans are known to the art.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g, The Pharmacological Basis of Therapeutics, Goodman and Gilman, eds., Macmillan Publishing Co., New York. For example, an, effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds are conveniently administered in unit dosage form; for example, containing 0.05 to 10000 mg, 0.5 to 10000 mg, 5 to 1000 mg, or about 100 mg of active ingredient per unit dosage form. In some embodiments, the dosage unit contains about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 750 mg, or about 1000 mg of active ingredient.

The invention also includes computer-related embodiments, such as a computer-readable medium, providing the structural representation of one of the crystal structures described herein, or for storing and/or evaluating the assay results described herein.

The storage medium (computer readable medium) in which the p53 structural representation is provided may be, e.g., random-access memory (RAM), read-only memory (ROM e.g. CDROM), a diskette, magnetic storage media, hybrids of these categories, etc. The storage medium may be local to the computer, or may be remote (e.g. a networked storage medium, including the internet). The present invention also provides methods of producing computer readable databases containing coordinates of 3-D structures of the invention; computer readable media embedded with or containing information regarding the 3-D structure of the invention; a computer programmed to carry out a method of the invention (e.g. for characterizing the structure of a p53 segment or for designing and/or selecting peptidic inhibitors), and data carriers having a program saved thereon for carrying out a method as described herein.

Any suitable computer can be used in the present invention.

An exemplary architecture for implementing a computing device in accordance with one or more embodiments, which may be used to implement any of the computing devices discussed herein, or any other computer system or computing device component thereof is described below. It will be appreciated that other devices that can be used with this computing device, such as a client or a server, may be similarly configured. The computing device may include a bus, a processor, a memory, a read only memory (ROM), a storage device, an input device, an output device, and a communication interface.

The bus may include one or more interconnects that permit communication among the components of the computing device. The processor may include any type of processor, microprocessor, or processing logic that may interpret and execute instructions (e.g., a field programmable gate array (FPGA)). The processor may include a single device (e.g., a single core) and/or a group of devices (e.g., multi-core). The memory may include a random access memory (RAM) or another type of dynamic storage device that may store information and instructions for execution by the processor. The memory may also be used to store temporary variables or other intermediate information during execution of instructions by the processor.

The ROM may include a ROM device and/or another type of static storage device that may store static information and instructions for the processor. The storage device may include a magnetic disk and/or optical disk and its corresponding drive for storing information and/or instructions. The storage device may include a single storage device or multiple storage devices, such as multiple storage devices operating in parallel. Moreover, the storage device may reside locally on the computing device and/or may be remote with respect to a server and connected thereto via network and/or another type of connection, such as a dedicated link or channel.

The input device may include any mechanism or combination of mechanisms that permit an operator to input information to the computing device, such as a keyboard, a mouse, a touch sensitive display device, a microphone, a pen-based pointing device, and/or a biometric input device, such as a voice recognition device and/or a finger print scanning device. The output device may include any mechanism or combination of mechanisms that outputs information to the operator, including a display, a printer, a speaker, etc.

The communication interface may include any transceiver-like mechanism that enables the computing device to communicate with other devices and/or systems, such as a client, a server, a license manager, a vendor, etc. For example, the communication interface may include one or more interfaces, such as a first interface coupled to a network and/or a second interface coupled to a license manager. Alternatively, the communication interface may include other mechanisms (e.g., a wireless interface) for communicating via a network, such as a wireless network. In one implementation, the communication interface may include logic to send code to a destination device, such as a target device that can include general purpose hardware (e.g., a personal computer form factor), dedicated hardware (e.g., a digital signal processing (DSP) device adapted to execute a compiled version of a model or a part of a model), etc.

The computing device may perform certain functions in response to the processor executing software instructions contained in a computer-readable medium, such as memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device.

EXAMPLES

Example I

Design and Characterization of Inhibitory Peptides and CPP Inhibitors

Based on the determination of the atomic structure of a fiber forming segment of p53, the inventors rationally designed a series of inhibitors that diminish aggregation in vitro. The inventors designed peptidic inhibitors to "cap" the growing aggregates of p53. Using the ZipperDB algorithm (Goldschmidt et al. 2010), the inventors identified the crystallizable amyloid-forming segments in the region that was also reported to be important for mutant p53 aggregation by Xu et al., 2011, who identified the sequence ILTIITL (SEQ ID NO: 2). The present inventors chemically synthesized the $p53_{252-258}$ and $p53_{253-258}$ segments, crystallized them and determined their three-dimensional structures by microcrystallography (FIG. 1). The structures displayed a typical steric zipper architecture, with parallel in-register β-strands and β-sheets interdigitating via hydrophobic side chains in a "face-to-back" (for $p53_{252-258}$) and "face-to-face" (for $p53_{253-258}$) orientation (Sawaya et al, Nature, 2007).

The atomic coordinates of the $p53_{253-258}$ (TITTLE) (SEQ ID NO: 20) and $p53_{252-258}$ (LTIITLE) (SEQ ID NO: 21) structures are shown in Tables 3 and 4, respectively.

TABLE 3

| | |
|---|---|
| REMARK | Date 2012-02-17 Time 19:46:52 PST −0800 (1329536812.65 s) |
| REMARK | PHENIX refinement |
| REMARK | |
| REMARK | ****************** INPUT FILES AND LABELS ******************* |
| REMARK | Reflections: |
| REMARK | file name: t6e_all.mtz |
| REMARK | labels: ['IMEAN, SIGIMEAN'] |
| REMARK | R-free flags: |
| REMARK | file name: t6e_all.mtz |
| REMARK | label: FreeR_flag |
| REMARK | test_flag_value: 0 |
| REMARK | Model file name(s): |
| REMARK | /home/absoriaga/APS/T6E/1.59A/build006_001-coot-0.pdb |
| REMARK | |
| REMARK | ****************** REFINEMENT SUMMARY: QUICK FACTS ********* |
| REMARK | Start: r_work = 0.1678 r_free = 0.1910 bonds = 0.009 angles = 1.861 |
| REMARK | Final: r_work = 0.1637 r_free = 0.1925 bonds = 0.009 angles = 1.861 |
| REMARK | |
| REMARK | *************************************************************** |
| REMARK | |
| REMARK | Rigid body refinement target: auto |
| REMARK | Information about total rigid body shift of selected groups: |
| REMARK | rotation (deg) translation (A) |
| REMARK | xyz total xyz total |
| REMARK | group 1: −0.342 −0.301 0.287 0.54 −0.02 0.03 0.02 0.04 |
| REMARK | group 2: −0.000 0.000 0.000 0.00 0.01 −0.02 0.01 0.02 |
| REMARK | group 3: −0.029 −0.173 −0.204 0.27 0.01 −0.01 0.05 0.05 |
| REMARK | ***************** REFINEMENT STATISTICS STEP BY STEP ******* |
| REMARK | leading digit, like 1_, means number of macro-cycle |
| REMARK | 0 : statistics at the very beginning when nothing is done yet |
| REMARK | 1_bss: bulk solvent correction and/or (anisotropic) scaling |
| REMARK | 1_rbr: rigid body refinement |
| REMARK | ------------------------------------------------------------ |
| REMARK | R-factors, x-ray target values and norm of gradient of x-ray target |
| REMARK | stage r-work r-free xray_target_w xray_target_t |
| REMARK | 0 : 0.1702 0.1913 1.200965e+00 1.236068e+00 |
| REMARK | 1_bss: 0.1678 0.1910 1.166180e+00 1.232305e+00 |
| REMARK | 1_ohs: 0.1678 0.1910 1.166180e+00 1.232305e+00 |
| REMARK | 1_rbr: 0.1678 0.1904 1.169224e+00 1.233750e+00 |
| REMARK | 1_adp: 0.1659 0.1935 1.164208e+00 1.257252e+00 |
| REMARK | 2_bss: 0.1657 0.1933 1.164333e+00 1.256966e+00 |
| REMARK | 2_ohs: 0.1657 0.1933 1.164333e+00 1.256966e+00 |
| REMARK | 2_adp: 0.1634 0.1913 1.153688e+00 1.227758e+00 |
| REMARK | 3_bss: 0.1634 0.1911 1.153695e+00 1.227577e+00 |
| REMARK | 3_ohs: 0.1634 0.1911 1.153695e+00 1.227577e+00 |
| REMARK | 3_adp: 0.1637 0.1925 1.158500e+00 1.245755e+00 |
| REMARK | 3_ohs: 0.1637 0.1925 1.158500e+00 1.245755e+00 |
| REMARK | ------------------------------------------------------------ |
| REMARK | stage k_sol b_sol b11 b22 b33 b12 b13 b23 |
| REMARK | 0 : 0.400 80.000 −2.385 0.077 2.308 −0.000 −0.841 0.000 |
| REMARK | 1_bss: 0.444 141.213 −2.385 0.077 2.308 −0.000 −0.841 −0.000 |
| REMARK | 1_ohs: 0.444 141.213 −2.385 0.077 2.308 −0.000 −0.841 −0.000 |
| REMARK | 1_rbr: 0.400 80.000 −2.385 0.077 2.308 −0.000 −0.841 −0.000 |
| REMARK | 1_adp: 0.400 80.000 −2.385 0.077 2.308 −0.000 −0.841 −0.000 |
| REMARK | 2_bss: 0.400 80.000 −2.399 0.015 2.229 −0.000 −0.834 0.000 |
| REMARK | 2_ohs: 0.400 80.000 −2.399 0.015 2.229 −0.000 −0.834 0.000 |
| REMARK | 2_adp: 0.400 80.000 −2.399 0.015 2.229 −0.000 −0.834 0.000 |
| REMARK | 3_bss: 0.400 80.000 −2.407 −0.032 2.194 −0.000 −0.819 0.000 |
| REMARK | 3_ohs: 0.400 80.000 −2.407 −0.032 2.194 −0.000 −0.819 0.000 |
| REMARK | 3_adp: 0.400 80.000 −2.407 −0.032 2.194 −0.000 −0.819 0.000 |
| REMARK | 3_ohs: 0.400 80.000 −2.407 −0.032 2.194 −0.000 −0.819 0.000 |
| REMARK | ------------------------------------------------------------ |
| REMARK | stage <pher> fom alpha beta |
| REMARK | 0 : 15.419 0.8841 0.0567 1.306 |
| REMARK | 1_bss: 15.363 0.8845 0.0567 1.295 |
| REMARK | 1_ohs: 15.363 0.8845 0.0567 1.295 |
| REMARK | 1_rbr: 15.338 0.8848 0.0568 1.298 |
| REMARK | 1_adp: 15.919 0.8793 0.0578 1.377 |
| REMARK | 2_bss: 15.892 0.8796 0.0577 1.375 |
| REMARK | 2_ohs: 15.892 0.8796 0.0577 1.375 |
| REMARK | 2_adp: 15.280 0.8856 0.0576 1.290 |
| REMARK | 3_bss: 15.263 0.8858 0.0575 1.289 |
| REMARK | 3_ohs: 15.263 0.8858 0.0575 1.289 |
| REMARK | 3_adp: 15.698 0.8817 0.0577 1.347 |
| REMARK | 3_ohs: 15.698 0.8817 0.0577 1.347 |
| REMARK | ------------------------------------------------------------ |
| REMARK | stage angl bond chir dihe plan repu geom_target |

TABLE 3-continued

```
REMARK   0 :    1.861 0.009 0.072 10.557 0.007 4.221 3.0983e-01
REMARK   1_bss:  1.861 0.009 0.072 10.557 0.007 4.221 3.0983e-01
REMARK   1_ohs:  1.861 0.009 0.072 10.557 0.007 4.221 3.0983e-01
REMARK   1_rbr:  1.861 0.009 0.072 10.557 0.007 4.221 3.0983e-01
REMARK   1_adp:  1.861 0.009 0.072 10.557 0.007 4.221 3.0983e-01
REMARK   2_bss:  1.861 0.009 0.072 10.557 0.007 4.221 3.0983e-01
REMARK   2_ohs:  1.861 0.009 0.072 10.557 0.007 4.221 3.0983e-01
REMARK   2_adp:  1.861 0.009 0.072 10.557 0.007 4.221 3.0983e-01
REMARK   3_bss:  1.861 0.009 0.072 10.557 0.007 4.221 3.0983e-01
REMARK   3_ohs:  1.861 0.009 0.072 10.557 0.007 4.221 3.0983e-01
REMARK   3_adp:  1.861 0.009 0.072 10.557 0.007 4.221 3.0983e-01
REMARK   3_ohs:  1.861 0.009 0.072 10.557 0.007 4.221 3.0983e-01
REMARK   ----------------------------------------------------------
REMARK   Maximal deviations:
REMARK   stage angl bond chir dihe plan repu |grad|
REMARK   0 :    9.207 0.052 0.183 22.762 0.017 1.935 7.3928e-01
REMARK   1_bss:  9.207 0.052 0.183 22.762 0.017 1.935 7.3928e-01
REMARK   1_ohs:  9.207 0.052 0.183 22.762 0.017 1.935 7.3928e-01
REMARK   1_rbr:  9.207 0.052 0.183 22.762 0.017 1.935 7.3928e-01
REMARK   1_adp:  9.207 0.052 0.183 22.762 0.017 1.935 7.3928e-01
REMARK   2_bss:  9.207 0.052 0.183 22.762 0.017 1.935 7.3928e-01
REMARK   2_ohs:  9.207 0.052 0.183 22.762 0.017 1.935 7.3928e-01
REMARK   2_adp:  9.207 0.052 0.183 22.762 0.017 1.935 7.3928e-01
REMARK   3_bss:  9.207 0.052 0.183 22.762 0.017 1.935 7.3928e-01
REMARK   3_ohs:  9.207 0.052 0.183 22.762 0.017 1.935 7.3928e-01
REMARK   3_adp:  9.207 0.052 0.183 22.762 0.017 1.935 7.3928e-01
REMARK   3_ohs:  9.207 0.052 0.183 22.762 0.017 1.935 7.3928e-01
REMARK   ----------------------------------------------------------
------
REMARK   |-----overall-----|---macromolecule----|------solvent-------|
REMARK   stage b_max b_min b_ave b_max b_min b_ave b_max b_min b_ave
REMARK   0 :    18.10 2.58 6.49 15.36 2.58 6.16 18.10 11.08 14.59
REMARK   1_bss:  18.10 2.58 6.49 15.36 2.58 6.16 18.10 11.08 14.59
REMARK   1_ohs:  18.10 2.58 6.49 15.36 2.58 6.16 18.10 11.08 14.59
REMARK   1_rbr:  18.10 2.58 6.49 15.36 2.58 6.16 18.10 11.08 14.59
REMARK   1_adp:  19.05 2.88 7.12 16.06 2.88 6.80 19.05 10.85 14.95
REMARK   2_bss:  19.05 2.88 7.12 16.06 2.88 6.80 19.05 10.85 14.95
REMARK   2_ohs:  19.05 2.88 7.12 16.06 2.88 6.80 19.05 10.85 14.95
REMARK   2_adp:  25.77 2.48 7.00 15.92 2.48 6.46 25.77 14.73 20.25
REMARK   3_bss:  25.77 2.48 7.00 15.92 2.48 6.46 25.77 14.73 20.25
REMARK   3_ohs:  25.77 2.48 7.00 15.92 2.48 6.46 25.77 14.73 20.25
REMARK   3_adp:  26.28 2.54 7.43 16.68 2.54 6.90 26.28 14.91 20.59
REMARK   3_ohs:  26.28 2.54 7.43 16.68 2.54 6.90 26.28 14.91 20.59
REMARK   ----------------------------------------------------------
------
REMARK   stage Deviation of refined
REMARK   model from start model
REMARK   max min mean
REMARK   0 :    0.000 0.000 0.000
REMARK   1_bss:  0.000 0.000 0.000
REMARK   1_ohs:  0.000 0.000 0.000
REMARK   1_rbr:  0.000 0.000 0.000
REMARK   1_adp:  0.000 0.000 0.000
REMARK   2_bss:  0.000 0.000 0.000
REMARK   2_ohs:  0.000 0.000 0.000
REMARK   2_adp:  0.000 0.000 0.000
REMARK   3_bss:  0.000 0.000 0.000
REMARK   3_ohs:  0.000 0.000 0.000
REMARK   3_adp:  0.000 0.000 0.000
REMARK   3_ohs:  0.000 0.000 0.000
REMARK   ----------------------------------------------------------
------
REMARK   MODEL CONTENT.
REMARK   ELEMENT ATOM RECORD COUNT OCCUPANCY SUM
REMARK   C 31 31.00
REMARK   Zn 1 1.00
REMARK   O 13 13.00
REMARK   N 6 6.00
REMARK   TOTAL 51 51.00
REMARK   ----------------------------------------------------------
-----
REMARK   r_free_flags.md5.hexdigest 250b0898748f0b3eeb957968c7c1d593
REMARK
REMARK   IF THIS FILE IS FOR PDB DEPOSITION: REMOVE ALL FROM THIS LINE UP.
REMARK 3
REMARK 3    REFINEMENT.
REMARK 3    PROGRAM: PHENIX (phenix.refine: 1.7.3_928)
REMARK 3    AUTHORS: Adams, Afonine, Chen, Davis, Echols, Gildea, Gopal,
REMARK 3    : Grosse-Kunstleve, Headd, Hung, Immormino, Ioerger, McCoy,
REMARK 3    : McKee, Moriarty, Pai, Read, Richardson, Richardson, Romo,
```

TABLE 3-continued

| REMARK 3 | : Sacchettini, Sauter, Smith, Storoni, Terwilliger, Zwart |
|---|---|
| REMARK 3 | |
| REMARK 3 | REFINEMENT TARGET: ML |
| REMARK 3 | |
| REMARK 3 | DATA USED IN REFINEMENT. |
| REMARK 3 | RESOLUTION RANGE HIGH (ANGSTROMS): 1.576 |
| REMARK 3 | RESOLUTION RANGE LOW (ANGSTROMS): 21.494 |
| REMARK 3 | MIN(FOBS/SIGMA_FOBS): 1.43 |
| REMARK 3 | COMPLETENESS FOR RANGE (%): 93.38 |
| REMARK 3 | NUMBER OF REFLECTIONS: 635 |
| REMARK 3 | NUMBER OF REFLECTIONS (NON-ANOMALOUS): 635 |
| REMARK 3 | |
| REMARK 3 | FIT TO DATA USED IN REFINEMENT. |
| REMARK 3 | R VALUE (WORKING + TEST SET): 0.1666 |
| REMARK 3 | R VALUE (WORKING SET): 0.1637 |
| REMARK 3 | FREE R VALUE: 0.1925 |
| REMARK 3 | FREE R VALUE TEST SET SIZE (%): 10.24 |
| REMARK 3 | FREE R VALUE TEST SET COUNT: 65 |
| REMARK 3 | |
| REMARK 3 | FIT TO DATA USED IN REFINEMENT (IN BINS). |
| REMARK 3 | BIN RESOLUTION RANGE COMPL. NWORK NFREE RWORK RFREE |
| REMARK 3 | 1 21.4963-1.5756 0.93 570 65 0.1637 0.1925 |
| REMARK 3 | |
| REMARK 3 | BULK SOLVENT MODELLING. |
| REMARK 3 | METHOD USED: FLAT BULK SOLVENT MODEL |
| REMARK 3 | SOLVENT RADIUS: 1.00 |
| REMARK 3 | SHRINKAGE RADIUS: 0.73 |
| REMARK 3 | GRID STEP FACTOR: 4.00 |
| REMARK 3 | K_SOL: 0.400 |
| REMARK 3 | B_SOL: 80.000 |
| REMARK 3 | |
| REMARK 3 | ERROR ESTIMATES. |
| REMARK 3 | COORDINATE ERROR (MAXIMUM-LIKELIHOOD BASED): 0.10 |
| REMARK 3 | PHASE ERROR (DEGREES, MAXIMUM-LIKELIHOOD BASED): 15.70 |
| REMARK 3 | |
| REMARK 3 | OVERALL SCALE FACTORS. |
| REMARK 3 | SCALE = SUM(\|F_OBS\|*\|F_MODEL\|)/SUM(\|F_MODEL\|**2): 0.0589 |
| REMARK 3 | ANISOTROPIC SCALE MATRIX ELEMENTS (IN CARTESIAN BASIS). |
| REMARK 3 | B11: −2.4068 |
| REMARK 3 | B22: −0.0323 |
| REMARK 3 | B33: 2.1936 |
| REMARK 3 | B12: −0.0000 |
| REMARK 3 | B13: −0.8190 |
| REMARK 3 | B23: 0.0000 |
| REMARK 3 | |
| REMARK 3 | R FACTOR FORMULA. |
| REMARK 3 | R = SUM(\|\|F_OBS\|−SCALE*\|F_MODEL\|\|)/SUM(\|F_OBS\|) |
| REMARK 3 | |
| REMARK 3 | TOTAL MODEL STRUCTURE FACTOR (F_MODEL). |
| REMARK 3 | F_MODEL = FB_CART * (F_CALC_ATOMS + F_BULK) |
| REMARK 3 | F_BULK = K_SOL * EXP(−B_SOL * S**2/4) * F_MASK |
| REMARK 3 | F_CALC_ATOMS = ATOMIC MODEL STRUCTURE FACTORS |
| REMARK 3 | FB_CART = EXP(−H(t) * A(−1) * B * A(−1t) * H) |
| REMARK 3 | A = orthogonalization matrix, H = MILLER INDEX |
| REMARK 3 | (t) = TRANSPOSE, (−1) = INVERSE |
| REMARK 3 | |
| REMARK 3 | STRUCTURE FACTORS CALCULATION ALGORITHM: FFT |
| REMARK 3 | |
| REMARK 3 | DEVIATIONS FROM IDEAL VALUES. |
| REMARK 3 | RMSD MAX COUNT |
| REMARK 3 | BOND: 0.009 0.052 47 |
| REMARK 3 | ANGLE: 1.861 9.207 64 |
| REMARK 3 | CHIRALITY: 0.072 0.183 11 |
| REMARK 3 | PLANARITY: 0.007 0.017 7 |
| REMARK 3 | DIHEDRAL: 10.557 22.762 17 |
| REMARK 3 | MIN NONBONDED DISTANCE: 1.935 |
| REMARK 3 | |
| REMARK 3 | MOLPROBITY STATISTICS. |
| REMARK 3 | ALL-ATOM CLASHSCORE: 9.62 |
| REMARK 3 | RAMACHANDRAN PLOT: |
| REMARK 3 | OUTLIERS: 0.00% |
| REMARK 3 | ALLOWED: 0.00% |
| REMARK 3 | FAVORED: 100.00% |
| REMARK 3 | ROTAMER OUTLIERS: 0.00% |
| REMARK 3 | CBETA DEVIATIONS: 0 |
| REMARK 3 | |
| REMARK 3 | ATOMIC DISPLACEMENT PARAMETERS. |
| REMARK 3 | WILSON B: 3.10 |
| REMARK 3 | RMS(B_ISO_OR_EQUIVALENT_BONDED): 2.15 |
| REMARK 3 | ATOMS NUMBER OF ATOMS |

TABLE 3-continued

```
REMARK   3    ISO.    ANISO.
REMARK   3    ALL: 51 51
REMARK   3    ALL (NO H): 51 51
REMARK   3    SOLVENT: 2 2
REMARK   3    NON-SOLVENT: 49 49
REMARK   3    HYDROGENS: 0 0
REMARK   3
REMARK   3    TLS DETAILS.
REMARK   3    NUMBER OF TLS GROUPS: 1
REMARK   3    ORIGIN: CENTER OF MASS
REMARK   3    TLS GROUP: 1
REMARK   3    SELECTION: all
REMARK   3    ORIGIN FOR THE GROUP (A): 10.5250 -0.1582 3.9867
REMARK   3    T TENSOR
REMARK   3    T11: 0.0284 T22: 0.0494
REMARK   3    T33: 0.0290 T12: 0.0055
REMARK   3    T13: 0.0058 T23: -0.0102
REMARK   3    L TENSOR
REMARK   3    L11: 0.0034 L22: 0.2021
REMARK   3    L33: 0.0378 L12: 0.0063
REMARK   3    L13: 0.0031 L23: -0.0919
REMARK   3    S TENSOR
REMARK   3    S11: 0.0075 S12: -0.0003 S13: -0.0248
REMARK   3    S21: -0.0899 S22: 0.0437 S23: -0.0012
REMARK   3    S31: -0.0422 S32: 0.1216 S33: 0.0477
REMARK   3
CRYST1   43.018 4.849 19.774 90.00 92.12 90.00 C 1 2 1
SCALE1   0.023246 0.000000 0.000861 0.00000
SCALE2   0.000000 0.206228 0.000000 0.00000
SCALE3   0.000000 0.000000 0.050606 0.00000
ATOM       1    N     THR  Z    1       1.586   -0.480    4.758  1.00   5.90           N
ANISOU     1    N     THR  Z    1       761      678      805    101    -37     58     N
ATOM       2    CA    THR  Z    1       2.773    0.083    5.366  1.00   4.89           C
ANISOU     2    CA    THR  Z    1       618      556      685    109    -42     48     C
ATOM       3    C     THR  Z    1       4.028   -0.525    4.751  1.00   4.69           C
ANISOU     3    C     THR  Z    1       583      552      645    117    -45     21     C
ATOM       4    O     THR  Z    1       4.118   -1.734    4.602  1.00   4.25           O
ANISOU     4    O     THR  Z    1       514      503      596    129    -53     20     O
ATOM       5    CB    THR  Z    1       2.767   -0.177    6.879  1.00  10.67           C
ANISOU     5    CB    THR  Z    1      1337     1315     1404    117    -36     39     C
ATOM       6    OG1   THR  Z    1       1.507    0.235    7.426  1.00  12.86           O
ANISOU     6    OG1   THR  Z    1      1629     1577     1680    104    -37     45     O
ATOM       7    CG2   THR  Z    1       3.887    0.582    7.558  1.00   6.79           C
ANISOU     7    CG2   THR  Z    1       813      838      927    116    -24     34     C
ATOM       8    N     ILE  Z    2       4.974    0.322    4.359  1.00   3.60           N
ANISOU     8    N     ILE  Z    2       454      437      477     89    -22      0     N
ATOM       9    CA    ILE  Z    2       6.260   -0.149    3.852  1.00   4.86           C
ANISOU     9    CA    ILE  Z    2       602      629      613     86     -9    -27     C
ATOM      10    C     ILE  Z    2       7.394    0.432    4.683  1.00   5.86           C
ANISOU    10    C     ILE  Z    2       706      797      724     71     17    -44     C
ATOM      11    O     ILE  Z    2       7.493    1.644    4.841  1.00   4.81           O
ANISOU    11    O     ILE  Z    2       584      666      578     46     32    -46     O
ATOM      12    CB    ILE  Z    2       6.489    0.275    2.388  1.00   4.24           C
ANISOU    12    CB    ILE  Z    2       558      541      511     64     -4    -37     C
ATOM      13    CG1   ILE  Z    2       5.349   -0.210    1.492  1.00   5.28           C
ANISOU    13    CG1   ILE  Z    2       719      631      658     75    -31    -19     C
ATOM      14    CG2   ILE  Z    2       7.836   -0.232    1.890  1.00   6.18           C
ANISOU    14    CG2   ILE  Z    2       792      822      734     62     12    -64     C
ATOM      15    CD1   ILE  Z    2       5.480    0.241    0.054  1.00   6.81           C
ANISOU    15    CD1   ILE  Z    2       950      811      828     54    -28    -28     C
ATOM      16    N     ILE  Z    3       8.248   -0.436    5.205  1.00   3.28           N
ANISOU    16    N     ILE  Z    3       346      502      398     86     21    -58     N
ATOM      17    CA    ILE  Z    3       9.450    0.006    5.891  1.00   2.54           C
ANISOU    17    CA    ILE  Z    3       229      449      289     72     44    -76     C
ATOM      18    C     ILE  Z    3      10.639   -0.630    5.179  1.00   3.98           C
ANISOU    18    C     ILE  Z    3       400      659      453     72     55    -99     C
ATOM      19    O     ILE  Z    3      10.711   -1.845    5.063  1.00   2.86           O
ANISOU    19    O     ILE  Z    3       243      520      322     97     43   -100     O
ATOM      20    CB    ILE  Z    3       9.414   -0.400    7.376  1.00   4.84           C
ANISOU    20    CB    ILE  Z    3       487      754      599     91     40    -69     C
ATOM      21    CG1   ILE  Z    3       8.220    0.261    8.067  1.00   4.33           C
ANISOU    21    CG1   ILE  Z    3       436      660      551     92     31    -45     C
ATOM      22    CG2   ILE  Z    3      10.697    0.002    8.080  1.00   2.84           C
ANISOU    22    CG2   ILE  Z    3       221      529      331     70     56    -80     C
ATOM      23    CD1   ILE  Z    3       7.800   -0.407    9.356  1.00   8.14           C
ANISOU    23    CD1   ILE  Z    3       909     1126     1058    102     19    -27     C
ATOM      24    N     THR  Z    4      11.553    0.199    4.686  1.00   3.85           N
ANISOU    24    N     THR  Z    4       391      661      411     44     77   -116     N
ATOM      25    CA    THR  Z    4      12.701   -0.291    3.932  1.00   4.67           C
ANISOU    25    CA    THR  Z    4       487      790      498     42     91   -137     C
```

TABLE 3-continued

| | | | | | | | | | | | | |
|---|---|---|---|---|---|---|---|---|---|---|---|---|
| ATOM | 26 | C | THR | Z | 4 | 14.018 | 0.243 | 4.471 | 1.00 | 6.53 | | C |
| ANISOU | 26 | C | THR | Z | 4 | 710 | 1042 | 729 | 20 | 101 | −138 | C |
| ATOM | 27 | O | THR | Z | 4 | 14.193 | 1.447 | 4.579 | 1.00 | 6.74 | | O |
| ANISOU | 27 | O | THR | Z | 4 | 748 | 1068 | 746 | −4 | 111 | −138 | O |
| ATOM | 28 | CB | THR | Z | 4 | 12.604 | 0.142 | 2.459 | 1.00 | 6.65 | | C |
| ANISOU | 28 | CB | THR | Z | 4 | 776 | 1022 | 729 | 25 | 96 | −142 | C |
| ATOM | 29 | CG1 | THR | Z | 4 | 11.403 | −0.379 | 1.887 | 1.00 | 7.91 | | O |
| ANISOU | 29 | CG1 | THR | Z | 4 | 961 | 1142 | 903 | 41 | 71 | −125 | O |
| ATOM | 30 | CG2 | THR | Z | 4 | 13.797 | −0.363 | 1.668 | 1.00 | 9.32 | | C |
| ANISOU | 30 | CG2 | THR | Z | 4 | 1109 | 1379 | 1053 | 22 | 109 | −159 | C |
| ATOM | 31 | N | LEU | Z | 5 | 14.953 | −0.649 | 4.775 | 1.00 | 4.74 | | N |
| ANISOU | 31 | N | LEU | Z | 5 | 463 | 829 | 511 | 29 | 96 | −140 | N |
| ATOM | 32 | CA | LEU | Z | 5 | 16.306 | −0.228 | 5.093 | 1.00 | 7.05 | | C |
| ANISOU | 32 | CA | LEU | Z | 5 | 745 | 1136 | 796 | 12 | 105 | −146 | C |
| ATOM | 33 | C | LEU | Z | 5 | 17.251 | −0.915 | 4.121 | 1.00 | 8.18 | | C |
| ANISOU | 33 | C | LEU | Z | 5 | 887 | 1289 | 933 | 14 | 113 | −156 | C |
| ATOM | 34 | O | LEU | Z | 5 | 17.302 | −2.135 | 4.056 | 1.00 | 9.26 | | O |
| ANISOU | 34 | O | LEU | Z | 5 | 1013 | 1426 | 1079 | 34 | 104 | −156 | O |
| ATOM | 35 | CB | LEU | Z | 5 | 16.654 | −0.594 | 6.532 | 1.00 | 5.48 | | C |
| ANISOU | 35 | CB | LEU | Z | 5 | 527 | 942 | 611 | 19 | 93 | −137 | C |
| ATOM | 36 | CG | LEU | Z | 5 | 15.814 | 0.143 | 7.577 | 1.00 | 10.92 | | C |
| ANISOU | 36 | CG | LEU | Z | 5 | 1220 | 1622 | 1307 | 16 | 87 | −126 | C |
| ATOM | 37 | CD1 | LEU | Z | 5 | 14.477 | −0.548 | 7.783 | 1.00 | 11.06 | | C |
| ANISOU | 37 | CD1 | LEU | Z | 5 | 1240 | 1621 | 1340 | 39 | 74 | −114 | C |
| ATOM | 38 | CD2 | LEU | Z | 5 | 16.578 | 0.252 | 8.883 | 1.00 | 16.68 | | C |
| ANISOU | 38 | CD2 | LEU | Z | 5 | 1938 | 2359 | 2040 | 12 | 83 | −123 | C |
| ATOM | 39 | N | GLU | Z | 6 | 18.017 | −0.137 | 3.371 | 1.00 | 6.37 | | N |
| ANISOU | 39 | N | GLU | Z | 6 | 668 | 1065 | 689 | −6 | 128 | −164 | N |
| ATOM | 40 | CA | GLU | Z | 6 | 18.866 | −0.744 | 2.353 | 1.00 | 7.06 | | C |
| ANISOU | 40 | CA | GLU | Z | 6 | 755 | 1157 | 769 | −3 | 139 | −173 | C |
| ATOM | 41 | C | GLU | Z | 6 | 20.226 | −1.181 | 2.865 | 1.00 | 10.47 | | C |
| ANISOU | 41 | C | GLU | Z | 6 | 1163 | 1608 | 1206 | −3 | 141 | −176 | C |
| ATOM | 42 | O | GLU | Z | 6 | 20.778 | −2.133 | 2.338 | 1.00 | 10.97 | | O |
| ANISOU | 42 | O | GLU | Z | 6 | 1221 | 1676 | 1270 | 9 | 144 | −181 | O |
| ATOM | 43 | CB | GLU | Z | 6 | 19.030 | 0.157 | 1.128 | 1.00 | 6.61 | | C |
| ANISOU | 43 | CB | GLU | Z | 6 | 725 | 1094 | 693 | −22 | 154 | −180 | C |
| ATOM | 44 | CG | GLU | Z | 6 | 19.460 | −0.607 | −0.118 | 1.00 | 8.76 | | C |
| ANISOU | 44 | CG | GLU | Z | 6 | 1009 | 1365 | 957 | −14 | 164 | −188 | C |
| ATOM | 45 | CD | GLU | Z | 6 | 19.538 | 0.284 | −1.341 | 1.00 | 9.29 | | C |
| ANISOU | 45 | CD | GLU | Z | 6 | 1106 | 1420 | 1005 | −32 | 177 | −192 | C |
| ATOM | 46 | OE1 | GLU | Z | 6 | 19.525 | 1.503 | −1.155 | 1.00 | 9.75 | | O |
| ANISOU | 46 | OE1 | GLU | Z | 6 | 1171 | 1476 | 1059 | −53 | 180 | −189 | O |
| ATOM | 47 | OE2 | GLU | Z | 6 | 19.597 | −0.234 | −2.473 | 1.00 | 8.35 | | O |
| ANISOU | 47 | OE2 | GLU | Z | 6 | 1006 | 1293 | 875 | −25 | 184 | −197 | O |
| ATOM | 48 | OXT | GLU | Z | 6 | 20.577 | −0.596 | 3.827 | 1.00 | 10.37 | | O |
| ANISOU | 48 | OXT | GLU | Z | 6 | 1140 | 1602 | 1196 | −13 | 137 | −173 | O |
| TER | | | | | | | | | | | | |
| HETATM | 49 | ZN | ZN | B | 1 | 1.135 | 0.108 | 2.815 | 1.00 | 6.38 | | ZN |
| ANISOU | 49 | ZN | ZN | B | 1 | 854 | 704 | 866 | 82 | −52 | 60 | ZN |
| TER | | | | | | | | | | | | |
| HETATM | 50 | O | HOH | A | 1 | −1.382 | −1.029 | 5.472 | 1.00 | 14.91 | | O |
| ANISOU | 50 | O | HOH | A | 1 | 1900 | 1800 | 1964 | 82 | −56 | 65 | O |
| HETATM | 51 | O | HOH | A | 2 | 10.560 | 2.460 | 0.798 | 1.00 | 26.28 | | O |
| ANISOU | 51 | O | HOH | A | 2 | 3357 | 3428 | 3199 | −21 | 86 | −116 | O |
| TER | | | | | | | | | | | | |
| END | | | | | | | | | | | | |

TABLE 4

REMARK Date 2012-02-15 Time 20:23:19 PST −0800 (1329366199.79 s)
REMARK PHENIX refinement
REMARK
REMARK **************** INPUT FILES AND LABELS ************
REMARK Reflections:
REMARK file name: 17e.mtz
REMARK labels: ['IMEAN, SIGIMEAN']
REMARK R-free flags:
REMARK file name: 17e.mtz
REMARK label: FreeR_flag
REMARK test_flag_value: 0
REMARK Model file name(s):
REMARK /home/absoriaga/APS/L7E/1.72A/build009_001-coot-1.pdb
REMARK
REMARK **************** REFINEMENT SUMMARY: QUICK FACTS ********
REMARK Start:  r_work = 0.1662 r_free = 0.1917 bonds = 0.007 angles = 1.078
REMARK Final:  r_work = 0.1626 r_free = 0.1919 bonds = 0.007 angles =

TABLE 4-continued

```
1.080
REMARK
REMARK ********************************************************************
REMARK
REMARK ***************** REFINEMENT STATISTICS STEP BY STEP *******
REMARK   leading digit, like 1__, means number of macro-cycle
REMARK   0 : statistics at the very beginning when nothing is done yet
REMARK   1 s: bulk solvent correction and/or (anisotropic) scaling
REMARK   1 z: refinement of coordinates
REMARK   ----------------------------------------------------------------
REMARK   R-factors, x-ray target values and norm of gradient of x-ray
target
REMARK   stage r-work r-free xray_target_w xray_target_t
REMARK   0 : 0.1771 0.1905 3.652480e-01 4.073357e-01
REMARK   1_bss:   0.1662 0.1917 2.117160e-01 3.975473e-01
REMARK   1_ohs:   0.1662 0.1917 2.117160e-01 3.975473e-01
REMARK   1_xyz:   0.1619 0.1890 1.754450e-01 3.580521e-01
REMARK   1_adp:   0.1674 0.1960 1.964973e-01 3.683984e-01
REMARK   2_bss:   0.1690 0.2055 2.335866e-01 4.382616e-01
REMARK   2_ohs:   0.1690 0.2055 2.335866e-01 4.382616e-01
REMARK   2_xyz:   0.1667 0.2061 2.401298e-01 4.654830e-01
REMARK   2_adp:   0.1654 0.2035 2.351643e-01 4.720430e-01
REMARK   3_bss:   0.1651 0.1920 2.011024e-01 3.900795e-01
REMARK   3_ohs:   0.1651 0.1920 2.011024e-01 3.900795e-01
REMARK   3_xyz:   0.1648 0.1901 1.963632e-01 3.805261e-01
REMARK   3_adp:   0.1648 0.1907 1.960629e-01 3.791067e-01
REMARK   3_bss:   0.1626 0.1919 1.911754e-01 3.915615e-01
REMARK   3_ohs:   0.1626 0.1919 1.911754e-01 3.915615e-01
REMARK   ----------------------------------------------------------------
REMARK   stage k_sol b_sol b11 b22 b33 b12 b13 b23
REMARK   0 : 0.600 80.084 1.142 0.456 -1.597 -0.206 0.548 -3.160
REMARK   1_bss:   0.600 39.857 1.373 0.376 -1.749 -0.196 0.551 -3.115
REMARK   1_ohs:   0.600 39.857 1.373 0.376 -1.749 -0.196 0.551 -3.115
REMARK   1_xyz:   0.600 39.857 1.373 0.376 -1.749 -0.196 0.551 -3.115
REMARK   1_adp:   0.600 39.857 1.373 0.376 -1.749 -0.196 0.551 -3.115
REMARK   2_bss:   0.600 37.717 1.451 0.387 -1.837 -0.208 0.596 -3.087
REMARK   2_ohs:   0.600 37.717 1.451 0.387 -1.837 -0.208 0.596 -3.087
REMARK   2_xyz:   0.600 37.717 1.451 0.387 -1.837 -0.208 0.596 -3.087
REMARK   2_adp:   0.600 37.717 1.451 0.387 -1.837 -0.208 0.596 -3.087
REMARK   3_bss:   0.600 35.678 1.451 0.387 -1.837 -0.208 0.596 -3.087
REMARK   3_ohs:   0.600 35.678 1.451 0.387 -1.837 -0.208 0.596 -3.087
REMARK   3_xyz:   0.600 35.678 1.451 0.387 -1.837 -0.208 0.596 -3.087
REMARK   3_adp:   0.600 35.678 1.451 0.387 -1.837 -0.208 0.596 -3.087
REMARK   3_bss:   0.600 30.131 1.451 0.387 -1.837 -0.208 0.596 -3.087
REMARK   3_ohs:   0.600 30.131 1.451 0.387 -1.837 -0.208 0.596 -3.087
REMARK   ----------------------------------------------------------------
REMARK   stage <pher>fom alpha beta
REMARK   0 : 26.144 0.8035 0.0979 0.313
REMARK   1_bss:   26.758 0.7974 0.0981 0.315
REMARK   1_ohs:   26.758 0.7974 0.0981 0.315
REMARK   1_xyz:   25.873 0.8067 0.0970 0.291
REMARK   1_adp:   25.849 0.8071 0.0970 0.294
REMARK   2_bss:   27.844 0.7856 0.0966 0.340
REMARK   2_ohs:   27.844 0.7856 0.0966 0.340
REMARK   2_xyz:   28.600 0.7770 0.0967 0.358
REMARK   2_adp:   28.733 0.7755 0.0978 0.362
REMARK   3_bss:   26.407 0.8007 0.0989 0.305
REMARK   3_ohs:   26.407 0.8007 0.0989 0.305
REMARK   3_xyz:   26.098 0.8041 0.0989 0.299
REMARK   3_adp:   25.979 0.8054 0.0988 0.297
REMARK   3_bss:   26.185 0.8034 0.0990 0.304
REMARK   3_ohs:   26.185 0.8034 0.0990 0.304
REMARK   ----------------------------------------------------------------
REMARK   stage angl bond chir dihe plan repu geom_target
REMARK   0 : 1.078 0.007 0.059 18.680 0.003 4.264 6.7991e-02
REMARK   1_bss:   1.078 0.007 0.059 18.680 0.003 4.264 6.7991e-02
REMARK   1_ohs:   1.078 0.007 0.059 18.680 0.003 4.264 6.7991e-02
REMARK   1_xyz:   1.169 0.007 0.070 17.979 0.004 4.264 7.1164e-02
REMARK   1_adp:   1.169 0.007 0.070 17.979 0.004 4.264 7.1164e-02
REMARK   2_bss:   1.169 0.007 0.070 17.979 0.004 4.264 7.1164e-02
REMARK   2_ohs:   1.169 0.007 0.070 17.979 0.004 4.264 7.1164e-02
REMARK   2_xyz:   1.090 0.007 0.064 18.389 0.003 4.263 6.8180e-02
REMARK   2_adp:   1.090 0.007 0.064 18.389 0.003 4.263 6.8180e-02
REMARK   3_bss:   1.090 0.007 0.064 18.389 0.003 4.263 6.8180e-02
REMARK   3_ohs:   1.090 0.007 0.064 18.389 0.003 4.263 6.8180e-02
REMARK   3_xyz:   1.080 0.007 0.061 18.346 0.003 4.263 6.7329e-02
REMARK   3_adp:   1.080 0.007 0.061 18.346 0.003 4.263 6.7329e-02
REMARK   3_bss:   1.080 0.007 0.061 18.346 0.003 4.263 6.7329e-02
REMARK   3_ohs:   1.080 0.007 0.061 18.346 0.003 4.263 6.7329e-02
REMARK   ----------------------------------------------------------------
```

TABLE 4-continued

```
REMARK  Maximal deviations:
REMARK  stage angl bond chi r dihe plan repu |grad|
REMARK  0 :   4.404 0.026 0.099 64.798 0.006 2.545 2.5455e−01
REMARK  1_bss:  4.404 0.026 0.099 64.798 0.006 2.545 2.5455e−01
REMARK  1_ohs:  4.404 0.026 0.099 64.798 0.006 2.545 2.5455e−01
REMARK  1_xyz:  3.519 0.024 0.127 61.369 0.007 2.579 2.8547e−01
REMARK  1_adp:  3.519 0.024 0.127 61.369 0.007 2.579 2.8547e−01
REMARK  2_bss:  3.519 0.024 0.127 61.369 0.007 2.579 2.8547e−01
REMARK  2_ohs:  3.519 0.024 0.127 61.369 0.007 2.579 2.8547e−01
REMARK  2_xyz:  2.977 0.027 0.123 64.073 0.006 2.591 2.4811e−01
REMARK  2_adp:  2.977 0.027 0.123 64.073 0.006 2.591 2.4811e−01
REMARK  3_bss:  2.977 0.027 0.123 64.073 0.006 2.591 2.4811e−01
REMARK  3_ohs:  2.977 0.027 0.123 64.073 0.006 2.591 2.4811e−01
REMARK  3_xyz:  3.213 0.022 0.113 63.776 0.005 2.591 2.4147e−01
REMARK  3_adp:  3.213 0.022 0.113 63.776 0.005 2.591 2.4147e−01
REMARK  3_bss:  3.213 0.022 0.113 63.776 0.005 2.591 2.4147e−01
REMARK  3_ohs:  3.213 0.022 0.113 63.776 0.005 2.591 2.4147e−01
REMARK  -----------------------------------------------------------
REMARK  |-----overall-----|---macromolecule----|------solvent------|
REMARK  stage b_max b_min b_ave b_max b_min b_ave b_max b_min b_ave
REMARK  0 :  43.34 4.47 13.98 43.34 4.47 13.89 27.13 10.20 15.93
REMARK  1_bss:  43.73 4.86 14.37 43.73 4.86 14.27 27.52 10.59 16.31
REMARK  1_ohs:  43.73 4.86 14.37 43.73 4.86 14.27 27.52 10.59 16.31
REMARK  1_xyz:  43.73 4.86 14.37 43.73 4.86 14.27 27.52 10.59 16.31
REMARK  1_adp:  34.22 6.51 13.79 34.22 6.51 13.65 23.32 12.30 16.48
REMARK  2_bss:  34.28 6.57 13.85 34.28 6.57 13.71 23.39 12.36 16.54
REMARK  2_ohs:  34.28 6.57 13.85 34.28 6.57 13.71 23.39 12.36 16.54
REMARK  2_xyz:  34.28 6.57 13.85 34.28 6.57 13.71 23.39 12.36 16.54
REMARK  2_adp:  35.29 6.18 14.27 35.29 6.18 14.08 31.25 10.44 17.92
REMARK  3_bss:  35.29 6.18 14.27 35.29 6.18 14.08 31.25 10.44 17.92
REMARK  3_ohs:  35.29 6.18 14.27 35.29 6.18 14.08 31.25 10.44 17.92
REMARK  3_xyz:  35.29 6.18 14.27 35.29 6.18 14.08 31.25 10.44 17.92
REMARK  3_adp:  35.70 5.88 14.25 35.70 5.88 14.08 31.83 9.77 17.66
REMARK  3_bss:  35.70 5.88 14.25 35.70 5.88 14.08 31.83 9.77 17.66
REMARK  3_ohs:  35.70 5.88 14.25 35.70 5.88 14.08 31.83 9.77 17.66
REMARK  -----------------------------------------------------------
REMARK  stage Deviation of refined
REMARK  model from start model
REMARK  max min mean
REMARK  0 :  0.000 0.000 0.000
REMARK  1_bss:   0.000 0.000 0.000
REMARK  1_ohs:   0.000 0.000 0.000
REMARK  1_xyz:   0.204 0.016 0.055
REMARK  1_adp:   0.204 0.016 0.055
REMARK  2_bss:   0.204 0.016 0.055
REMARK  2_ohs:   0.204 0.016 0.055
REMARK  2_xyz:   0.351 0.010 0.060
REMARK  2_adp:   0.351 0.010 0.060
REMARK  3_bss:   0.351 0.010 0.060
REMARK  3_ohs:   0.351 0.010 0.060
REMARK  3_xyz:   0.336 0.009 0.059
REMARK  3_adp:   0.336 0.009 0.059
REMARK  3_bss:   0.336 0.009 0.059
REMARK  3_ohs:   0.336 0.009 0.059
REMARK  -----------------------------------------------------------
REMARK  MODEL CONTENT.
REMARK  ELEMENT ATOM RECORD COUNT OCCUPANCY SUM
REMARK  C 40 37.00
REMARK  O 15 14.00
REMARK  N 7 7.00
REMARK  TOTAL 62 58.00
REMARK  -----------------------------------------------------------
REMARK  r_free_flags.md5.hexdigest 3bd517a07859c6c80cf6f8225f5dfe4a
REMARK
REMARK  IF THIS FILE IS FOR PDB DEPOSITION: REMOVE ALL FROM THIS LINE UP.
REMARK 3
REMARK 3    REFINEMENT.
REMARK 3    PROGRAM: PHENIX (phenix.refine: 1.7.3_928)
REMARK 3    AUTHORS: Adams, Afonine, Chen, Davis, Echols, Gildea, Gopal,
REMARK 3    : Grosse-Kunstleve, Headd, Hung, Immormino, Ioerger, McCoy,
REMARK 3    : McKee, Moriarty, Pai, Read, Richardson, Richardson, Romo,
REMARK 3    : Sacchettini, Sauter, Smith, Storoni, Terwilliger, Zwart
REMARK 3
REMARK 3    REFINEMENT TARGET: ML
REMARK 3
REMARK 3    DATA USED IN REFINEMENT.
REMARK 3    RESOLUTION RANGE HIGH (ANGSTROMS): 1.703
REMARK 3    RESOLUTION RANGE LOW (ANGSTROMS): 21.302
REMARK 3    MIN(FOBS/SIGMA_FOBS): 2.14
REMARK 3    COMPLETENESS FOR RANGE (%): 93.72
```

TABLE 4-continued

```
REMARK 3   NUMBER OF REFLECTIONS: 507
REMARK 3   NUMBER OF REFLECTIONS (NON-ANOMALOUS): 507
REMARK 3
REMARK 3   FIT TO DATA USED IN REFINEMENT.
REMARK 3   R VALUE (WORKING + TEST SET): 0.1655
REMARK 3   R VALUE (WORKING SET): 0.1626
REMARK 3   FREE R VALUE: 0.1919
REMARK 3   FREE R VALUE TEST SET SIZE (%): 9.86
REMARK 3   FREE R VALUE TEST SET COUNT: 50
REMARK 3
REMARK 3   FIT TO DATA USED IN REFINEMENT (IN BINS).
REMARK 3   BIN RESOLUTION RANGE COMPL. NWORK NFREE RWORK RFREE
REMARK 3   1 21.3038-1.7025 0.94 457 50 0.1626 0.1919
REMARK 3
REMARK 3   BULK SOLVENT MODELLING.
REMARK 3   METHOD USED: FLAT BULK SOLVENT MODEL
REMARK 3   SOLVENT RADIUS: 1.30
REMARK 3   SHRINKAGE RADIUS: 1.11
REMARK 3   GRID STEP FACTOR: 4.00
REMARK 3   K_SOL: 0.600
REMARK 3   B_SOL: 30.131
REMARK 3
REMARK 3   ERROR ESTIMATES.
REMARK 3   COORDINATE ERROR (MAXIMUM-LIKELIHOOD BASED): 0.06
REMARK 3   PHASE ERROR (DEGREES, MAXIMUM-LIKELIHOOD BASED): 26.18
REMARK 3
REMARK 3   OVERALL SCALE FACTORS.
REMARK 3   SCALE = SUM(|F_OBS|*|F_MODEL|)/SUM(|F_MODEL|**2): 0.0995
REMARK 3   ANISOTROPIC SCALE MATRIX ELEMENTS (IN CARTESIAN BASIS).
REMARK 3   B11: 1.4505
REMARK 3   B22: 0.3869
REMARK 3   B33: -1.8374
REMARK 3   B12: -0.2078
REMARK 3   B13: 0.5956
REMARK 3   B23: -3.0866
REMARK 3
REMARK 3   R FACTOR FORMULA.
REMARK 3   R = SUM(||F_OBS|-SCALE*|F_MODEL||)/SUM(|F_OBS|)
REMARK 3
REMARK 3   TOTAL MODEL STRUCTURE FACTOR (F_MODEL).
REMARK 3   F_MODEL = FB_CART * (F_CALC_ATOMS + F_BULK)
REMARK 3   F_BULK = K_SOL * EXP(-B_SOL * S**2/4) * F_MASK
REMARK 3   F_CALC_ATOMS = ATOMIC MODEL STRUCTURE FACTORS
REMARK 3   FB_CART = EXP(-H(t) * A(-1) * B * A(-1t) * H)
REMARK 3   A = orthogonalization matrix, H = MILLER INDEX
REMARK 3   (t) = TRANSPOSE, (-1) = INVERSE
REMARK 3
REMARK 3   STRUCTURE FACTORS CALCULATION ALGORITHM: FFT
REMARK 3
REMARK 3   DEVIATIONS FROM IDEAL VALUES.
REMARK 3   RMSD MAX COUNT
REMARK 3   BOND: 0.007 0.022 61
REMARK 3   ANGLE: 1.080 3.213 85
REMARK 3   CHIRALITY: 0.061 0.113 15
REMARK 3   PLANARITY: 0.003 0.005 9
REMARK 3   DIHEDRAL: 18.346 63.776 24
REMARK 3   MIN NONBONDED DISTANCE: 2.591
REMARK 3
REMARK 3   MOLPROBITY STATISTICS.
REMARK 3   ALL-ATOM CLASHSCORE: 0.00
REMARK 3   RAMACHANDRAN PLOT:
REMARK 3   OUTLIERS: 0.00%
REMARK 3   ALLOWED: 0.00%
REMARK 3   FAVORED: 100.00%
REMARK 3   ROTAMER OUTLIERS: 0.00%
REMARK 3   CBETA DEVIATIONS: 0
REMARK 3
REMARK 3   ATOMIC DISPLACEMENT PARAMETERS.
REMARK 3   WILSON B: 12.73
REMARK 3   RMS(B_ISO_OR_EQUIVALENT_BONDED): 2.28
REMARK 3   ATOMS NUMBER OF ATOMS
REMARK 3   ISO. ANISO.
REMARK 3   ALL: 62 62
REMARK 3   ALL (NO H): 62 62
REMARK 3   SOLVENT: 3 3
REMARK 3   NON-SOLVENT: 59 59
REMARK 3   HYDROGENS: 0 0
REMARK 3
REMARK 3   TLS DETAILS.
REMARK 3   NUMBER OF TLS GROUPS: 1
```

TABLE 4-continued

| | | | | | | | | | | | | |
|---|---|---|---|---|---|---|---|---|---|---|---|---|
| REMARK | 3 | ORIGIN: CENTER OF MASS | | | | | | | | | | |
| REMARK | 3 | TLS GROUP: 1 | | | | | | | | | | |
| REMARK | 3 | SELECTION: all | | | | | | | | | | |
| REMARK | 3 | ORIGIN FOR THE GROUP (A): 0.1185 6.8484 9.0224 | | | | | | | | | | |
| REMARK | 3 | T TENSOR | | | | | | | | | | |
| REMARK | 3 | T11: 0.0582 T22: 0.0750 | | | | | | | | | | |
| REMARK | 3 | T33: 0.0849 T12: 0.0099 | | | | | | | | | | |
| REMARK | 3 | T13: 0.0029 T23: 0.0090 | | | | | | | | | | |
| REMARK | 3 | L TENSOR | | | | | | | | | | |
| REMARK | 3 | L11: 2.3157 L22: 4.0221 | | | | | | | | | | |
| REMARK | 3 | L33: 4.8813 L12: −0.4063 | | | | | | | | | | |
| REMARK | 3 | L13: −1.1355 L23: 1.8148 | | | | | | | | | | |
| REMARK | 3 | S TENSOR | | | | | | | | | | |
| REMARK | 3 | S11: 0.0087 S12: −0.0689 S13: −0.0102 | | | | | | | | | | |
| REMARK | 3 | S21: 0.1493 S22: 0.2397 S23: −0.0164 | | | | | | | | | | |
| REMARK | 3 | S31: −0.1178 S32: 0.0395 S33: −0.1915 | | | | | | | | | | |
| REMARK | 3 | | | | | | | | | | | |
| CRYST1 | 4.811 12.599 21.340 86.59 89.29 79.15 P 1 | | | | | | | | | | | |
| SCALE1 | 0.207857 −0.039846 −0.000241 0.00000 | | | | | | | | | | | |
| SCALE2 | 0.000000 0.080817 −0.004715 0.00000 | | | | | | | | | | | |
| SCALE3 | 0.000000 0.000000 0.046944 0.00000 | | | | | | | | | | | |
| ATOM | 1 | N | LEU | Z | 1 | 0.068 | 1.128 | −2.181 | 1.00 | 15.58 | | N |
| ANISOU | 1 | N | LEU | Z | 1 | 1869 | 2159 | 1891 | −379 | −166 | −311 | N |
| ATOM | 2 | CA | LEU | Z | 1 | −0.127 | 0.804 | −0.768 | 1.00 | 13.08 | | C |
| ANISOU | 2 | CA | LEU | Z | 1 | 1469 | 1787 | 1714 | −344 | −176 | −260 | C |
| ATOM | 3 | C | LEU | Z | 1 | 0.557 | 1.846 | 0.111 | 1.00 | 12.34 | | C |
| ANISOU | 3 | C | LEU | Z | 1 | 1366 | 1679 | 1644 | −279 | −114 | −206 | C |
| ATOM | 4 | O | LEU | Z | 1 | 1.781 | 1.952 | 0.130 | 1.00 | 13.64 | | O |
| ANISOU | 4 | O | LEU | Z | 1 | 1530 | 1824 | 1827 | −273 | −43 | −284 | O |
| ATOM | 5 | CB | LEU | Z | 1 | 0.402 | −0.599 | −0.458 | 1.00 | 12.49 | | C |
| ANISOU | 5 | CB | LEU | Z | 1 | 1398 | 1613 | 1735 | −354 | −160 | −349 | C |
| ATOM | 6 | CG | LEU | Z | 1 | −0.073 | −1.318 | 0.805 | 1.00 | 16.04 | | C |
| ANISOU | 6 | CG | LEU | Z | 1 | 1832 | 1974 | 2288 | −335 | −172 | −291 | C |
| ATOM | 7 | CD1 | LEU | Z | 1 | 0.293 | −2.794 | 0.696 | 1.00 | 16.64 | | C |
| ANISOU | 7 | CD1 | LEU | Z | 1 | 1983 | 1918 | 2423 | −348 | −154 | −382 | C |
| ATOM | 8 | CD2 | LEU | Z | 1 | 0.530 | −0.711 | 2.067 | 1.00 | 13.96 | | C |
| ANISOU | 8 | CD2 | LEU | Z | 1 | 1552 | 1694 | 2057 | −229 | −151 | −224 | C |
| ATOM | 9 | N | THR | Z | 2 | −0.245 | 2.601 | 0.848 | 1.00 | 9.66 | | N |
| ANISOU | 9 | N | THR | Z | 2 | 1001 | 1359 | 1311 | −237 | −137 | −97 | N |
| ATOM | 10 | CA | THR | Z | 2 | 0.258 | 3.731 | 1.615 | 1.00 | 9.85 | | C |
| ANISOU | 10 | CA | THR | Z | 2 | 1039 | 1364 | 1338 | −192 | −78 | −58 | C |
| ATOM | 11 | C | THR | Z | 2 | −0.369 | 3.689 | 2.996 | 1.00 | 9.29 | | C |
| ANISOU | 11 | C | THR | Z | 2 | 920 | 1277 | 1333 | −139 | −99 | 14 | C |
| ATOM | 12 | O | THR | Z | 2 | −1.588 | 3.575 | 3.128 | 1.00 | 10.23 | | O |
| ANISOU | 12 | O | THR | Z | 2 | 997 | 1428 | 1461 | −132 | −136 | 80 | O |
| ATOM | 13 | CB | THR | Z | 2 | −0.098 | 5.087 | 0.930 | 1.00 | 12.90 | | C |
| ANISOU | 13 | CB | THR | Z | 2 | 1518 | 1766 | 1616 | −175 | −48 | 11 | C |
| ATOM | 14 | OG1 | THR | Z | 2 | 0.500 | 5.144 | −0.374 | 1.00 | 13.73 | | O |
| ANISOU | 14 | OG1 | THR | Z | 2 | 1716 | 1876 | 1624 | −232 | 0 | −46 | O |
| ATOM | 15 | CG2 | THR | Z | 2 | 0.400 | 6.264 | 1.758 | 1.00 | 11.80 | | C |
| ANISOU | 15 | CG2 | THR | Z | 2 | 1419 | 1573 | 1490 | −154 | 36 | 33 | C |
| ATOM | 16 | N | ILE | Z | 3 | 0.474 | 3.750 | 4.022 | 1.00 | 6.76 | | N |
| ANISOU | 16 | N | ILE | Z | 3 | 595 | 923 | 1051 | −104 | −75 | −16 | N |
| ATOM | 17 | C | ILE | Z | 3 | 0.661 | 5.006 | 6.102 | 1.00 | 6.68 | | C |
| ANISOU | 17 | C | ILE | Z | 3 | 605 | 896 | 1039 | −19 | −41 | 27 | C |
| ATOM | 18 | O | ILE | Z | 3 | 1.887 | 5.178 | 6.075 | 1.00 | 7.92 | | O |
| ANISOU | 18 | O | ILE | Z | 3 | 742 | 1064 | 1205 | −36 | −33 | −81 | O |
| ATOM | 19 | CA | ILE | Z | 3 | 0.020 | 3.798 | 5.405 | 1.00 | 7.02 | | C |
| ANISOU | 19 | CA | ILE | Z | 3 | 625 | 937 | 1106 | −48 | −79 | 49 | C |
| ATOM | 20 | CB | ILE | Z | 3 | 0.398 | 2.499 | 6.141 | 1.00 | 5.88 | | C |
| ANISOU | 20 | CB | ILE | Z | 3 | 498 | 739 | 998 | −12 | −112 | 30 | C |
| ATOM | 21 | CG1 | ILE | Z | 3 | −0.197 | 1.292 | 5.414 | 1.00 | 7.70 | | C |
| ANISOU | 21 | CG1 | ILE | Z | 3 | 733 | 931 | 1261 | −74 | −124 | 28 | C |
| ATOM | 22 | CG2 | ILE | Z | 3 | −0.022 | 2.568 | 7.617 | 1.00 | 8.38 | | C |
| ANISOU | 22 | CG2 | ILE | Z | 3 | 862 | 1029 | 1293 | 49 | −99 | 106 | C |
| ATOM | 23 | CD1 | ILE | Z | 3 | 0.383 | −0.041 | 5.862 | 1.00 | 10.12 | | C |
| ANISOU | 23 | CD1 | ILE | Z | 3 | 1113 | 1135 | 1598 | −27 | −141 | −2 | C |
| ATOM | 24 | N | ILE | Z | 4 | −0.170 | 5.849 | 6.712 | 1.00 | 8.44 | | N |
| ANISOU | 24 | N | ILE | Z | 4 | 855 | 1114 | 1239 | 17 | −8 | 104 | N |
| ATOM | 25 | CA | ILE | Z | 4 | 0.310 | 7.046 | 7.404 | 1.00 | 7.11 | | C |
| ANISOU | 25 | CA | ILE | Z | 4 | 735 | 924 | 1043 | 31 | 42 | 71 | C |
| ATOM | 26 | C | ILE | Z | 4 | −0.366 | 7.145 | 8.763 | 1.00 | 9.16 | | C |
| ANISOU | 26 | C | ILE | Z | 4 | 1019 | 1178 | 1284 | 100 | 54 | 127 | C |
| ATOM | 27 | O | ILE | Z | 4 | −1.596 | 7.044 | 8.848 | 1.00 | 8.49 | | O |
| ANISOU | 27 | O | ILE | Z | 4 | 916 | 1102 | 1207 | 133 | 78 | 218 | O |
| ATOM | 28 | CB | ILE | Z | 4 | −0.014 | 8.320 | 6.591 | 1.00 | 8.14 | | C |
| ANISOU | 28 | CB | ILE | Z | 4 | 940 | 1014 | 1138 | 18 | 112 | 105 | C |
| ATOM | 29 | CG1 | ILE | Z | 4 | 0.721 | 8.307 | 5.245 | 1.00 | 11.61 | | C |
| ANISOU | 29 | CG1 | ILE | Z | 4 | 1404 | 1449 | 1560 | −64 | 136 | 51 | C |
| ATOM | 30 | CG2 | ILE | Z | 4 | 0.332 | 9.585 | 7.377 | 1.00 | 8.29 | | C |

TABLE 4-continued

| | | | | | | | | | | | |
|---|---|---|---|---|---|---|---|---|---|---|---|
| ANISOU | 30 | CG2 | ILE | Z | 4 | 1043 | 971 | 1135 | 18 | 190 | 66 | C |
| ATOM | 31 | CD1 | ILE | Z | 4 | 0.132 | 9.280 | 4.232 | 1.00 | 13.32 | | C |
| ANISOU | 31 | CD1 | ILE | Z | 4 | 1748 | 1614 | 1700 | −43 | 187 | 133 | C |
| ATOM | 32 | N | THR | Z | 5 | 0.410 | 7.339 | 9.826 | 1.00 | 6.75 | | N |
| ANISOU | 32 | N | THR | Z | 5 | 745 | 875 | 946 | 121 | 39 | 57 | N |
| ATOM | 33 | CA | THR | Z | 5 | −0.180 | 7.546 | 11.152 | 1.00 | 8.77 | | C |
| ANISOU | 33 | CA | THR | Z | 5 | 1064 | 1122 | 1145 | 187 | 68 | 102 | C |
| ATOM | 34 | C | THR | Z | 5 | 0.418 | 8.797 | 11.800 | 1.00 | 10.69 | | C |
| ANISOU | 34 | C | THR | Z | 5 | 1368 | 1352 | 1343 | 179 | 100 | 5 | C |
| ATOM | 35 | O | THR | Z | 5 | 1.642 | 8.947 | 11.834 | 1.00 | 11.07 | | O |
| ANISOU | 35 | O | THR | Z | 5 | 1384 | 1431 | 1390 | 132 | 48 | −131 | O |
| ATOM | 36 | CB | THR | Z | 5 | 0.030 | 6.323 | 12.090 | 1.00 | 10.48 | | C |
| ANISOU | 36 | CB | THR | Z | 5 | 1320 | 1349 | 1315 | 244 | 5 | 121 | C |
| ATOM | 37 | OG1 | THR | Z | 5 | 1.406 | 6.224 | 12.461 | 1.00 | 13.87 | | O |
| ANISOU | 37 | OG1 | THR | Z | 5 | 1741 | 1820 | 1710 | 274 | −97 | −3 | O |
| ATOM | 38 | CG2 | THR | Z | 5 | −0.409 | 5.021 | 11.436 | 1.00 | 10.34 | | C |
| ANISOU | 38 | CG2 | THR | Z | 5 | 1271 | 1306 | 1351 | 221 | −8 | 189 | C |
| ATOM | 39 | N | LEU | Z | 6 | −0.446 | 9.696 | 12.278 | 1.00 | 12.10 | | N |
| ANISOU | 39 | N | LEU | Z | 6 | 1617 | 1488 | 1493 | 217 | 192 | 50 | N |
| ATOM | 40 | C | LEU | Z | 6 | −0.524 | 10.931 | 14.393 | 1.00 | 14.83 | | C |
| ANISOU | 40 | C | LEU | Z | 6 | 2136 | 1804 | 1694 | 281 | 272 | −38 | C |
| ATOM | 41 | O | LEU | Z | 6 | −1.656 | 10.521 | 14.660 | 1.00 | 14.90 | | O |
| ANISOU | 41 | O | LEU | Z | 6 | 2144 | 1819 | 1699 | 347 | 331 | 79 | O |
| ATOM | 42 | CD1 | LEU | Z | 6 | 0.469 | 11.983 | 9.998 | 1.00 | 16.40 | | C |
| ANISOU | 42 | CD1 | LEU | Z | 6 | 2268 | 1865 | 2100 | 55 | 338 | −42 | C |
| ATOM | 43 | CD2 | LEU | Z | 6 | −0.326 | 14.207 | 10.832 | 1.00 | 17.47 | | C |
| ANISOU | 43 | CD2 | LEU | Z | 6 | 2662 | 1793 | 2182 | 133 | 528 | −40 | C |
| ATOM | 44 | CA | ALEU | Z | 6 | −0.015 | 10.912 | 12.963 | 0.50 | 14.01 | | C |
| ANISOU | 44 | CA | ALEU | Z | 6 | 1950 | 1686 | 1686 | 202 | 244 | −51 | C |
| ATOM | 45 | CB | ALEU | Z | 6 | −0.561 | 12.158 | 12.261 | 0.50 | 14.80 | | C |
| ANISOU | 45 | CB | ALEU | Z | 6 | 2124 | 1682 | 1819 | 202 | 359 | −19 | C |
| ATOM | 46 | CG | ALEU | Z | 6 | 0.295 | 12.867 | 11.213 | 0.50 | 18.60 | | C |
| ANISOU | 46 | CG | ALEU | Z | 6 | 2642 | 2089 | 2334 | 89 | 398 | −91 | C |
| ATOM | 47 | CA | BLEU | Z | 6 | −0.015 | 10.912 | 12.963 | 0.50 | 14.11 | | C |
| ANISOU | 47 | CA | BLEU | Z | 6 | 1963 | 1699 | 1699 | 202 | 244 | −51 | C |
| ATOM | 48 | CB | BLEU | Z | 6 | −0.561 | 12.158 | 12.261 | 0.50 | 14.85 | | C |
| ANISOU | 48 | CB | BLEU | Z | 6 | 2130 | 1688 | 1825 | 202 | 359 | −19 | C |
| ATOM | 49 | CG | BLEU | Z | 6 | 0.295 | 12.867 | 11.213 | 0.50 | 18.60 | | C |
| ANISOU | 49 | CG | BLEU | Z | 6 | 2642 | 2089 | 2334 | 89 | 398 | −91 | C |
| ATOM | 50 | N | GLU | Z | 7 | 0.304 | 11.423 | 15.303 | 1.00 | 16.19 | | N |
| ANISOU | 50 | N | GLU | Z | 7 | 2376 | 1992 | 1785 | 261 | 239 | −177 | N |
| ATOM | 51 | CA | GLU | Z | 7 | −0.131 | 11.710 | 16.667 | 1.00 | 21.28 | | C |
| ANISOU | 51 | CA | GLU | Z | 7 | 3145 | 2639 | 2303 | 331 | 284 | −189 | C |
| ATOM | 52 | C | GLU | Z | 7 | 0.706 | 12.866 | 17.251 | 1.00 | 26.95 | | C |
| ANISOU | 52 | C | GLU | Z | 7 | 3942 | 3336 | 2963 | 264 | 284 | −387 | C |
| ATOM | 53 | O | GLU | Z | 7 | 1.715 | 13.280 | 16.656 | 1.00 | 23.82 | | O |
| ANISOU | 53 | O | GLU | Z | 7 | 3479 | 2938 | 2632 | 147 | 244 | −521 | O |
| ATOM | 54 | CB | GLU | Z | 7 | −0.080 | 10.461 | 17.558 | 1.00 | 21.58 | | C |
| ANISOU | 54 | CB | GLU | Z | 7 | 3220 | 2754 | 2224 | 408 | 196 | −134 | C |
| ATOM | 55 | CG | GLU | Z | 7 | 1.286 | 9.867 | 17.714 | 1.00 | 25.98 | | C |
| ANISOU | 55 | CG | GLU | Z | 7 | 3733 | 3401 | 2738 | 411 | 3 | −247 | C |
| ATOM | 56 | CD | GLU | Z | 7 | 1.279 | 8.604 | 18.550 | 1.00 | 30.97 | | C |
| ANISOU | 56 | CD | GLU | Z | 7 | 4464 | 4072 | 3233 | 533 | −84 | −159 | C |
| ATOM | 57 | OE1 | GLU | Z | 7 | 0.937 | 8.687 | 19.747 | 1.00 | 30.45 | | O |
| ANISOU | 57 | OE1 | GLU | Z | 7 | 4567 | 4010 | 2992 | 603 | −53 | −141 | O |
| ATOM | 58 | OE2 | GLU | Z | 7 | 1.617 | 7.528 | 18.011 | 1.00 | 35.70 | | O |
| ANISOU | 58 | OE2 | GLU | Z | 7 | 5002 | 4678 | 3883 | 565 | −171 | −105 | O |
| ATOM | 59 | OXT | GLU | Z | 7 | 0.405 | 13.433 | 18.308 | 1.00 | 28.69 | | O |
| ANISOU | 59 | OXT | GLU | Z | 7 | 4293 | 3537 | 3070 | 304 | 342 | −438 | O |
| TER | 60 | | GLU | Z | 7 | | | | | | | |
| HETATM | 60 | O | HOH | A | 1 | −2.703 | 7.785 | 14.692 | 1.00 | 9.77 | | O |
| ANISOU | 60 | O | HOH | A | 1 | 1411 | 1229 | 1073 | 352 | 306 | 277 | O |
| HETATM | 62 | O | HOH | A | 2 | 1.726 | 3.935 | 14.170 | 1.00 | 31.83 | | O |
| ANISOU | 62 | O | HOH | A | 2 | 4220 | 4052 | 3822 | 494 | −238 | 95 | O |
| TER | 63 | | HOH | A | 2 | | | | | | | |
| END | | | | | | | | | | | | |

Table 5 shows statistics of X-ray data collection and refinement for the crystal structures of the p53 segments. Table 5 discloses "LTIITLE" as SEQ ID NO: 21 and "TIITLE" as SEQ ID NO: 20.

TABLE 5

|  | 252-LTIITLE-258 | 253-TIITLE-258 |
|---|---|---|
| Crystal parameters | | |
| Space group | P1 | C2 |
| Cell dimensions | | |
| a, b, c (Å) | 4.81, 12.60, 21.34 | 43.02, 4.85, 19.77 |
| α, β, γ (°) | 86.59, 89.29, 79.15 | 90, 92.12, 90 |
| Molecules in Asymmetric Unit | 1 | 1 |
| Data collection | | |
| Synchrotron beamline | APS (24-ID-E) | APS (24-ID-E) |
| Wavelength (Å) | 0.9792 | 0.9792 |
| Resolution range (Å) | 1.70 | 1.58 |
| Unique Reflections | 507 | 635 |
| Overall Redundancy | 3.1 (2.6)$^a$ | 4.0 (3.0) |
| Completeness (%) | 97.0 (91.4) | 96.5 (87.7) |
| $R_{merge}$ (%)$^b$ | 9.6 (50.5) | 11.4 (32.9) |
| <I/σI> | 10.6 (2.9) | 8.9 (4.1) |
| Refinement | | |
| Resolution (Å) | 21.30-1.70 | 21.49-1.58 |
| $R_{work}$ (%)$^c$ | 16.2 | 16.4 |
| $R_{free}$ (%)$^d$ | 19.2 | 19.3 |
| No. atoms | | |
| Protein | 59 | 48 |
| Ligand/ion | 0 | 1 |
| Water | 2 | 2 |
| Overall B-factors | 12.7 | 3.1 |
| R.m.s. deviation | | |
| Bond length (Å) | 0.007 | 0.009 |
| Bond angle (°) | 1.080 | 1.861 |

$^a$Values in parentheses correspond to the highest resolution shell
$^b R_{merge} = \Sigma |I - <I>|/\Sigma I$
$^c R_{work} = \Sigma |F_o - F_c|/\Sigma F_o$
$^d R_{free} = \Sigma |F_o - F_c|/\Sigma F_o$, calculated using a random set containing reflections that were not included throughout structure refinement The inventors applied their Rosetta-based method (Sievers et al, Nature, 2011) to design inhibitors that disrupt p53 aggregation, using the p53$_{252-258}$ structure as a template. In other embodiments of the invention, the p53$_{253-258}$ structure is used as a template to design inhibitors.

Table 1, shown earlier in this application, shows a list of 16 representative sequences obtained by this method.

Table 6 shows the calculated properties of a selection of inhibitors.

TABLE 6

Aggregation propensities and capping energies of the designed inhibitors.

| | Zipper energy$^a$ (kcal/mol) | Capping energy$^b$ | | | |
|---|---|---|---|---|---|
| | | Single Sheet | | Triple Sheet | |
| | | absolute (kcal/mol) | relative to LTIITLE | absolute (kcal/mol) | relative to LTIITLE |
| LTIITLE(native) | −26.2 | −42.2 | 0.0 | −86.2 | 0.0 |
| LTRITLE | −18.2 | −40.5 | 1.7 | −84.6 | 1.6 |
| LTRIYLE | −19.5 | −41.0 | 1.1 | −85.2 | 1.0 |
| YTRITLE | −19.3 | −40.3 | 1.9 | −83.5 | 2.6 |
| YTRIYLE | −19.8 | −41.3 | 0.8 | −85.3 | 0.9 |
| ETRITLE | −19.0 | −39.8 | 2.4 | −83.0 | 3.1 |

TABLE 6-continued

Aggregation propensities and capping energies of the designed inhibitors.

| | Zipper energy$^a$ (kcal/mol) | Capping energy$^b$ | | | |
|---|---|---|---|---|---|
| | | Single Sheet | | Triple Sheet | |
| | | absolute (kcal/mol) | relative to LTIITLE | absolute (kcal/mol) | relative to LTIITLE |
| LTKITLE | −25.5 | −41.2 | 0.9 | −84.0 | 2.2 |
| WTKITLE | −24.3$^c$ | −40.1 | 2.1 | −82.1 | 4.0 |
| YTKITLE | −24.1 | −40.8 | 1.3 | −82.5 | 3.6 |

The peptides in Table 6, reading from top to bottom, are represented by SEQ ID NOS 21, 4, 7, 5, 8, 6, 12, 14 and 13.

Figure 2:
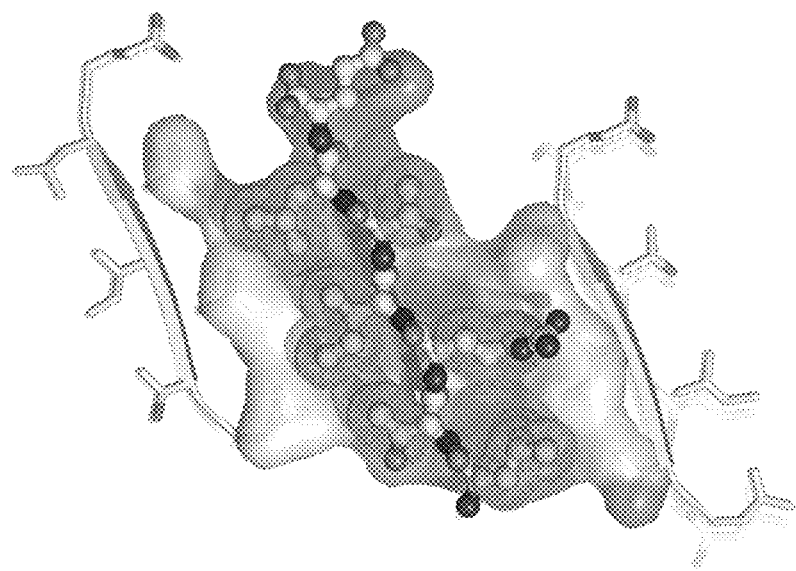
FIG. 2 shows INH-1R modeled on the $p53_{252-258}$ crystal structure. Three adjacent sheets are represented. The cyan ball-and-stick inhibitor has a high surface complementarity to the LTIITLE (SEQ ID NO: 21) structure. The arginine (in yellow) of INH-1R collides with the opposing β-sheet, inhibiting further filament growth. The inhibitor can bind to the top and/or to the bottom (along the fiber axis) of the steric zipper template. The view is down the fiber axis.

FIG. 2 shows the INH-1R inhibitor modeled on the p53$_{252-258}$ structure. As evident, the ARG substitution collides with the adjacent sheet efficiently inhibiting new monomers from attaching to the free fiber end and preventing further growth.

The designed inhibitors were synthesized and tested in an in vitro Thioflavin T aggregation assay (FIG. 3). The most effective design, INH-1R, delayed the onset of aggregation and lowered the amount of aggregates present at all concentrations tested, even at a molar ratio of 1 inhibitor to 10 p53 molecules (FIG. 3).

Figure 4:
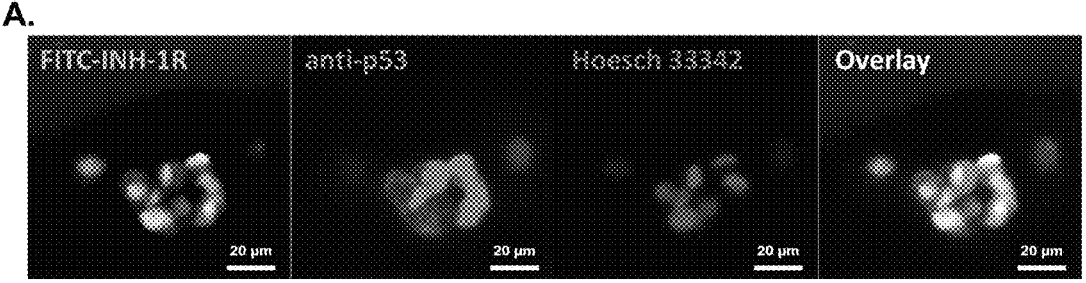
FIG. 4 shows that the cell-penetrating version of INH-1R (1NH-1R CPP) is able to enter human cancer cells. INH-1R CPP was covalently linked to a FITC fluorescent label and added to different cancer cell lines or primary cells directly obtained from ovarian cancer patients (as depicted here). A. The peptide successfully penetrated into the cytosol and nucleus of the cells (in green) and co-localized with p53. The cell nuclei are stained with Hoechst 33342 (blue), while p53 is recognized by an anti-p53 antibody and stained in red. B. The peptide co-localizes with protein aggregates in the same cells. Protein aggregates are stained with the commercially available OC antibody (in red). This indicates that INH-1R CPP binds to aggregated p53 in these ovarian cancer cells.
Figure 4:
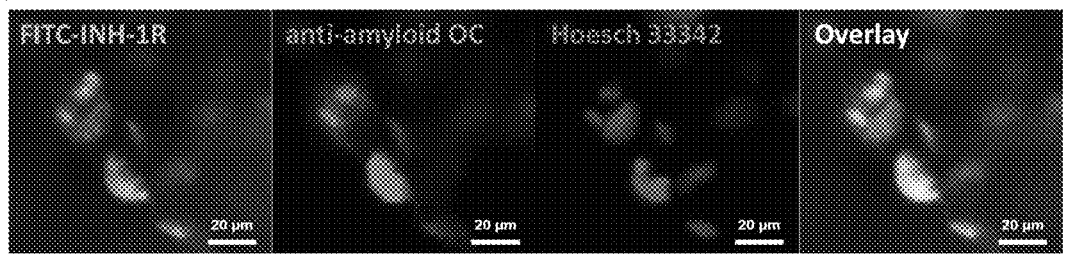

To render the inhibitors cell permeable, the inventors fused the peptide-inhibitor panel to a nine-residue poly arginine tag through a three-residue linker, of sequence RPI, derived from endogenous p53 sequence. To confirm their ability to enter cells, the cell penetrating INH-1R inhibitor was linked to a FITC moiety in order to detect the intracellular localization of the probe by fluorescence microscopy (FIG. 4). We treated different cancer cell lines, including but not limited to OVCAR-3, CAOV-3, WiDr, Detroit 562 as well as primary cells derived from cancer patients with the FITC labeled inhibitor for 24 hours. After extensive washes to remove unbound inhibitors, the cells were fixed in formaldehyde and p53 was stained using a commercially available p53 antibody. As visible in FIG. 4A, the inhibitor was not only able to penetrate the cell membrane, but also to actually enter the nucleus and co-localize with its target, p53. Additionally, the inhibitor was found co-localized with protein aggregates as stained by the conformation specific antibody OC (Kayed et al, 2007, FIG. 4B).

Figure 5:
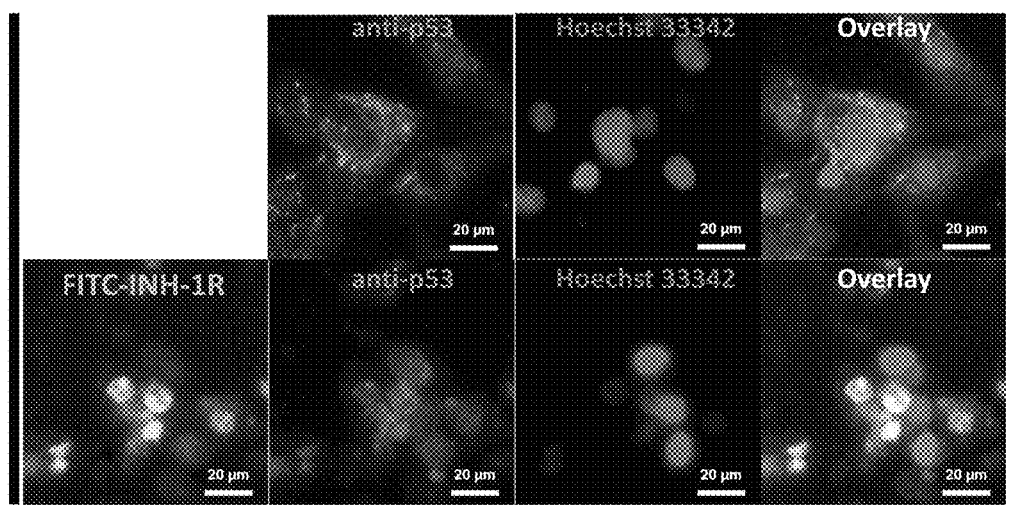
FIG. 5 shows that INH-1R CPP causes re-localization of p53 and breaks up aggregation. In the top panels, p53 stain of primary cells from a serous ovarian carcinoma patient show punctate p53 cytosolic staining. Upon 24 hours of treatment with 10 μM of INH-1R CPP, all the puncta disappeared and p53 is now diffused and localized to the nucleus where it can exert its function of transcription factor and oncosuppressor as visible in the bottom panel. Again, INH-1R CPP co-localizes with p53 (INH-1R CPP in green, p53 in red, nuclei in blue).

The structure-guided, rationally designed p53 amyloid inhibitors of the invention specifically target those cancer cells bearing p53 molecules having an aberrant conformation (e.g. aggregated or misfolded p53). We demonstrated the capability of the inhibitors to halt aggregation progression in vitro (FIG. 3). We then tested the inhibitor on established cancer cell lines as well as on primary cells derived from serous ovarian cancer patients in order to confirm the clinical relevance of our findings. Our inhibitor is designed to specifically target those tumor cells expressing an altered misfolded form of p53 and should have no effect on cells bearing functional, properly folded p53 or aggregation-incompetent p53 mutants. To confirm this, we included several controls. Three established cell lines, one bearing WT p53 (MCF-7) and two which were previously characterized for their p53 aggregation status, one with a non-aggregating mutation (WiDr) and one with a p53 aggregation prone mutation (Detroit 562), were used as negative and positive controls. One of the effects of the inhibitor was to cause re-localization of p53 from the cytosolic compartment to the nucleus (FIG. 5). This effect was not observed in case of the WT p53 bearing cells MCF 7 (FIG. 2a), suggesting that INH-1R is active only when p53 loses is structural integrity.

Another effect of the inhibitor was to cause re-folding of misfolded p53 into a WT-like, functional conformation. p53 treated with INH-1R in PA40 cells failed to be recognized by the antibody PAb240 which specifically targets partially unfolded, mutant p53 (FIG. 6), indicating that re-localization was accompanied by protein re-folding. As a consequence of p53 maintaining a physiological fold, the levels of p53 proteins in treated cells were decreasing in a dose dependent manner. Properly folded p53 is rapidly degraded in cells as a control mechanism. Misfolded/aggregated p53 cannot be efficiently targeted for degradation therefore protein levels are high in the absence of the inhibitor. This is additional evidence of the ability of the INH-1R to generate a population of folded p53. Without wishing to be bound by any particular mechanism, it is suggested that this is due to the inhibitor titrating out pre-existing p53 aggregates, by the inhibitor changing the equilibrium between aggregated/misfolded/folded p53, by the inhibitor chaperoning or masking the exposed aggregation prone segment.

INH-1R caused cell death in a dose dependent manner with less than 50% of cancer cells surviving after only 24 hours of treatment with a dose of 10 µM in a 2D culture system as detected by a standard MTS assay (FIG. 7A). The effect of INH-1R is specific since a poly-ARG alone or a scrambled inhibitor sequence did not elicit any effect. Similar results were obtained with both cancer cells or primary cells grown in a 3D culture system. In this case cells were plated in 1:1 mixture of PrEGM:matrigel. After cell layer solidified, cells were overlaid with warm PrEGM media containing either the inhibitor or a scrambled control peptide at concentration ranging from 0.1 to 10 µM for 5 to 7 days.

The inhibitor caused both an increase in apoptosis and a decrease in cell proliferation in a dose dependent manner (FIGS. 7B and 7C) as evidenced by an increase in AnnexinV stain and a decrease in Ki67 stain. Apoptosis as well as necrosis were induced specifically by treatment with INH-1R as opposed to a scrambled peptide sequence as evidence also by a combined Hoechst/PI/YO-PRO-1 stain (FIG. 8). Cell death can be monitored also by FACS methods as visible in FIG. 9, were OVCAR-3 cells treated for 24 hours with 10 µM of inhibitor showed a decrease in cell size and increase in granularity, typical manifestations of cell death.

Specificity and efficacy of INH-1R were confirmed by up-regulation of p53 target genes only in tumor cells bearing aggregation-prone mutations as tested by QPCR (FIG. 8) or RNAseq methods.

In our in vivo studies, we attempted to mimic a post-surgical debulking situation in which patients with minimal residual tumor mass are administered chemotherapy. NOD/SCID mice were injected subcutaneously with OVCAR-3 cells bearing the aggregation prone p53 R248Q mutation and treated intraperitoneally with 15 mg/kg of either INH-1R as a single therapeutic agent, a control scrambled peptide, or vehicle daily for 14 days (FIG. 9). Mice treated with INH-1R showed diminished tumor proliferation, with a xenograft mass reduced by 75% in weight (FIGS. 9B and 9C). The residual tumor tissue showed a pronounced p21 and MDM2 activation, indicative of p53 activation (FIG. 9D). The inhibitor was also tested in vivo on mice carrying pre-existing tumors with similar effect.

Pharmacokinetic profile of the intraperitoneally infused peptide showed a serum peak concentration of approx. 1.2 µM 1 hour after injection. The peptide concentration decreased to approximately 0.3 µM 2 hours post infusion, and remained stable for up to 12 hours (FIG. 10). Given the relative stability of the peptide in serum, IV administration is an acceptable alternative route of administration.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited herein, including U.S. provisional application Ser. No. 61/821,157, filed May 8, 2013 and in the figures are hereby incorporated in their entirety by reference, particularly with regard to the information for which they are cited.

REFERENCES

Naiki, H., Higuchi, K., Hosokawa, M., and Takeda, T. (1989). Fluorometric determination of amyloid fibrils in vitro using the fluorescent dye, thioflavine T. Anal. Biochem., 177, 244-249

Hatakeyama S, Sugihara K, Shibata T K, Nakayama J, Akama T O, Tamura N, Wong S M, Bobkov A A, Takano Y, Ohyama C, Fukuda M, Fukuda M N. (2011). Targeted drug delivery to tumor vasculature by a carbohydrate mimetic peptide. Proc Natl Acad Sci USA. 108(49): 19587-92.

Olson E S, Jiang T, Aguilera T A, Nguyen Q T, Ellies L G, Scadeng M, Tsien R Y. (2010). Activatable cell penetrating peptides linked to nanoparticles as dual probes for in vivo fluorescence and M R imaging of proteases. Proc Natl Acad Sci USA. 107(9):4311-6.

Jiang L, Liu C, Leibly D, Landau M, Zhao M, Hughes M P, Eisenberg D S. (2013). Structure-based discovery of fiber-binding compounds that reduce the cytotoxicity of amyloid beta. Elife 2:e00857.

Goldschmidt L, Teng P K, Riek R, Eisenberg D. (2010). Identifying the amylome, proteins capable of forming amyloid-like fibrils. Proc Natl Acad Sci USA 107(8): 3487-3492.

Sawaya M R, Sambashivan S, Nelson R, Ivanova M I, Sievers S A, Apostol M I, Thompson M J, Balbirnie M, Wiltzius J J, McFarlane H T, Madsen A Ø, Riekel C, Eisenberg D. (2007). Atomic structures of amyloid cross-beta spines reveal varied steric zippers. Nature 447(7143): 453-457.

Nelson R, Sawaya M R, Balbirnie M, Madsen A Ø, Riekel C, Grothe R, Eisenberg D. (2005). Structure of the cross-beta spine of amyloid-like fibrils. Nature 435(7043):773-778.

Sievers S A, Karanicolas J, Chang H W, Zhao A, Jiang L, Zirafi O, Stevens J T, Munch J, Baker D, Eisenberg D. (2011). Structure-based design of non-natural amino-acid inhibitors of amyloid fibril formation. Nature 475(7354): 96-100.

Ishimaru D1, Andrade L R, Teixeira L S, Quesado P A, Maiolino L M, Lopez P M, Cordeiro Y, Costa L T, Heckl W M, Weissmüller G, Foguel D, Silva J L (2003). Fibrillar aggregates of the tumor suppressor p53 core domain. Biochemistry 42(30):9022-7.

Lasagna-Reeves C A, Clos A L, Castillo-Carranza D, Sengupta U, Guerrero-Muñoz M, Kelly B, Wagner R, Kayed R. (2013). Dual role of p53 amyloid formation in cancer;

loss of function and gain of toxicity. Biochem Biophys Res Commun. 430(3):963-8.

Silva J L, Vieira T C, Gomes M P, Bom A P, Lima L M, Freitas M S, Ishimaru D, Cordeiro Y, Foguel D. (2010). Ligand binding and hydration in protein misfolding: insights from studies of prion and p53 tumor suppressor proteins. Acc Chem Res. 43(2):271-9.

Ishimaru D, Ano Bom A P, Lima L M, Quesado P A, Oyama M F, de Moura Gallo C V, Cordeiro Y, Silva J L. (2009). Cognate DNA stabilizes the tumor suppressor p53 and prevents misfolding and aggregation. Biochemistry 48(26):6126-35.

Galea C, Bowman P, Kriwacki R W. (2005). Disruption of an intermonomer salt bridge in the p53 tetramerization domain results in an increased propensity to form amyloid fibrils. Protein Sci. 14(12):2993-3003.

Rigacci S, Bucciantini M, Relini A, Pesce A, Gliozzi A, Berti A, Stefani M. (2008). The (1-63) region of the p53 transactivation domain aggregates in vitro into cytotoxic amyloid assemblies. Biophys J. 94(9):3635-46.

Levy C B, Stumbo A C, Ano Bom A P D, Portari E A, Carneiro Y, Silva J L, De Moura-Gallo C V (2011). Co-localization of mutant p53 and amyloid-like protein aggregates in breast tumors. The International Journal of Biochemistry & Cell Biology 43:60-64.

Eisenberg D and Jucker M (2012). The amyloid state of proteins in human diseases. Cell 148(6):1188-203.

Soussi, T., Ishioka, C., Claustres, M., and Beroud, C. (2006). Locus-specific mutation databases: Pitfalls and good practice based on the p53 experience. Nat. Rev. Cancer 6:83-90.

Wilcken R, Wang G, Boeckler F M, Fersht A R. (2012). Kinetic mechanism of p53 oncogenic mutant aggregation and its inhibition. Proc Natl Acad Sci USA. 109(34): 13584-9.

Bullock and Fersht. (2001). Rescuing the function of mutant p53. Nature Reviews Cancer 1, 68-76.

Kayed, R., Head, E., Sarsoza, F., Saing, T., Cotman, C. W., Necula, M., Margol, L., Wu, J., Breydo, L., Thompson, J. L., et al. (2007). Fibril specific, conformation dependent antibodies recognize a generic epitope common to amyloid fibrils and fibrillar oligomers that is absent in prefibrillar oligomers. Molecular Neurodegeneration 2:18

Gannon, J V, et al, 1990, Activating mutations in p53 produce a common conformational effect. A monoclonal antibody specific for the mutant form, EMBO J., 9: 1595-602

Xu J, Reumers J, Couceiro J R, De Smet F, Gallardo R, Rudyak S, Cornelis A, Rozenski J, Zwolinska A, Marine J C, Lambrechts D, Suh Y A, Rousseau F, Schymkowitz J. (2011). Gain of function of mutant p53 by coaggregation with multiple tumor suppressors. Nat Chem Biol 5:285-95.

---

We claim:

1. A method for treating a subject having a cancer associated with p53 having an aberrant conformation, comprising administering to the subject an effective amount of a pharmaceutical composition comprising a peptide represented by the sequence [L,Y,E,W] T [R,K], I T [L,Y] E (SEQ ID NO: 1).

2. The method of claim 1, wherein the peptide is represented by the sequence [L,Y,E,W] T [R,K], I T [L,Y] E (SEQ ID NO: 1).

3. The method of claim 1, wherein the peptide is represented by the sequence [L,Y,E,W] T R I T [L,Y] E (SEQ ID NO: 3).

4. The method of claim 1, wherein the peptide consists of the sequence [L,Y,E,W] T [R,K], I T [L,Y] E (SEQ ID NO: 1).

5. The method of claim 1, wherein the peptide consists of the sequence [L,Y,E,W] T R I T [L,Y] E (SEQ ID NO: 3).

6. The method of claim 1, wherein the peptide comprises one of the following sequences:

```
LTRITLE          (SEQ ID NO: 4)

YTRITLE          (SEQ ID NO: 5)

ETRITLE          (SEQ ID NO: 6)

LTRIYLE          (SEQ ID NO: 7)

YTRIYLE          (SEQ ID NO: 8)

WTRITLE          (SEQ ID NO: 9)

WTRIYLE          (SEQ ID NO: 10)

ETRIYLE          (SEQ ID NO: 11)

LTKITLE          (SEQ ID NO: 12)

YTKITLE          (SEQ ID NO: 13)

WTKITLE          (SEQ ID NO: 14)

ETKITLE          (SEQ ID NO: 15)

LTKIYLE          (SEQ ID NO: 16)

YTKIYLE,         (SEQ ID NO: 17)
or
ETKIYLE.         (SEQ ID NO: 18)
```

7. The method of claim 1, wherein the peptide is fused, optionally via a linker sequence, to a cell penetrating peptide (CPP).

8. The method of claim 1, wherein the peptide is represented by the consensus sequence $(R_{1-16})$P I [L,Y,E,W] T [R,K], I T [L,Y] E (SEQ ID NO: 19).

9. The method of claim 1, wherein the peptide is combined with a pharmaceutically acceptable carrier.

10. A method for treating a subject who has a mutant gene encoding p53 which imparts a susceptibility to develop cancers, comprising administering to the subject a plurality of doses comprising in total an effective amount of the pharmaceutical composition of a pharmaceutical composition comprising a peptide represented by the sequence [L,Y,E,W] T [R,K], I T [L,Y] E (SEQ ID NO: 1).

11. A method for treating a subject having a cancer associated with p53 having an aberrant conformation, comprising administering to the subject an effective amount of a pharmaceutical composition comprising a peptide represented by the sequence $(R_{2-16})$ P I (L/Y/E/W) T (R/K) I T L E (SEQ ID NO: 19), provided the sequence does not comprise YTRITLE (SEQ ID NO: 5).

12. The method of claim 11, wherein the pharmaceutical composition comprises a pharmaceutically acceptable carrier.

13. The method of claim 11, wherein the peptide comprises the amino acid sequence LTRITLE (SEQ ID NO: 4).

14. The method of claim 13, wherein the pharmaceutical composition comprises a pharmaceutically acceptable carrier.

15. The method of claim 11, wherein the peptide is coupled to 4 to 16 arginine residues.

16. The method of claim 15, wherein the peptide is coupled to the arginine residues by a peptide linker comprising 1-7 amino acids.

17. The method of claim 16, wherein the peptide forms a polycationic structure.

18. The method of claim 16, wherein the peptide forms an amphipathic structure.

19. The method of claim 16, wherein the peptide is less than 30 amino acids in length.

20. The method of claim 14, wherein the pharmaceutically acceptable carrier includes a peptide stabilizing excipient.

21. The method of claim 20, wherein the peptide stabilizing excipient is a preservative that inhibits the growth of microorganisms.

22. The method of claim 11, wherein the peptide comprises the sequence RRRRRRRRRRPILTRITLE (SEQ ID NO: 22).

23. The method of claim 11, wherein the peptide comprises the sequence $(R_{2-16})$ P I L T R I T L E (SEQ ID NO: 19).

24. The method of claim 1 further comprising inhibiting proliferation of cancer cells or shrinking a tumor in the subject.

25. The method of claim 1 wherein the cancer is selected from ovarian cancer, breast cancer, colon carcinomas and basal cell carcinomas.

26. The method of claim 10 further comprising preventing the development of tumors in the subject.

27. A method of treating a subject having a tumor with aberrant p53 conformation, the method comprising administering to the subject an effective amount of a pharmaceutical composition comprising a peptide represented by the sequence [L,Y,E,W] T [R,K], I T [L,Y] E (SEQ ID NO: 1).

28. The method of claim 27 wherein the aberrant p53 conformation is aggregated p53 or misfolded p53.

29. The method of claim 28 wherein the composition lowers the amount of p53 aggregates, or restores the folding of a misfolded p53.

30. The method of claim 27 wherein the composition re-activates a biological or biochemical activity of p53 disrupted by the aberrant p53 conformation.

* * * * *

SEQUENCE LISTING

```
<160> NUMBER OF SEQ ID NOS: 82

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Tyr, Glu or Trp
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (6)..(6)
<223> OTHER INFORMATION: Leu or Tyr

<400> SEQUENCE: 1

Xaa Thr Xaa Ile Thr Xaa Glu
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Leu Thr Ile Ile Thr Leu
1               5

<210> SEQ ID NO 3
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu, Tyr, Glu or Trp
<220> FEATURE:
<221> NAME/KEY: MOD_RES
<222> LOCATION: (6)..(6)
<223> OTHER INFORMATION: Leu or Tyr

<400> SEQUENCE: 3

Xaa Thr Arg Ile Thr Xaa Glu
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Thr Arg Ile Thr Leu Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Thr Arg Ile Thr Leu Glu
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Thr Arg Ile Thr Leu Glu
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Thr Arg Ile Tyr Leu Glu
1               5

<210> SEQ ID NO 8
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

Tyr Thr Arg Ile Tyr Leu Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Thr Arg Ile Thr Leu Glu
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Thr Arg Ile Tyr Leu Glu
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Thr Arg Ile Tyr Leu Glu
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Thr Lys Ile Thr Leu Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Thr Lys Ile Thr Leu Glu
1               5
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Thr Lys Ile Thr Leu Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Thr Lys Ile Thr Leu Glu
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Thr Lys Ile Tyr Leu Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Thr Lys Ile Tyr Leu Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Thr Lys Ile Tyr Leu Glu
1               5

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: misc_feature
<222> LOCATION: (1)..(16)
<223> OTHER INFORMATION: This region may encompass 1-16 'Arg' residues,
      wherein some positions may be absent
<220> FEATURE:
<221> NAME/KEY: MOD_RES
<222> LOCATION: (19)..(19)
<223> OTHER INFORMATION: Leu, Tyr, Glu or Trp
<220> FEATURE:
<221> NAME/KEY: MOD_RES
<222> LOCATION: (21)..(21)
<223> OTHER INFORMATION: Arg or Lys
<220> FEATURE:
<221> NAME/KEY: MOD_RES
<222> LOCATION: (24)..(24)
<223> OTHER INFORMATION: Leu or Tyr

<400> SEQUENCE: 19

Arg Arg Arg Arg Arg Arg Arg Arg Arg Arg Arg Arg Arg Arg Arg Arg
1               5                   10                  15

Pro Ile Xaa Thr Xaa Ile Thr Xaa Glu
            20                  25

<210> SEQ ID NO 20
<211> LENGTH: 6
<212> TYPE: PRT
<213> ORGANISM: Unknown
<220> FEATURE:
<223> OTHER INFORMATION: Description of Unknown: p53
      peptide segment

<400> SEQUENCE: 20

Thr Ile Ile Thr Leu Glu
1               5

<210> SEQ ID NO 21
<211> LENGTH: 7
<212> TYPE: PRT
<213> ORGANISM: Unknown
<220> FEATURE:
<223> OTHER INFORMATION: Description of Unknown: p53
      peptide segment

<400> SEQUENCE: 21

Leu Thr Ile Ile Thr Leu Glu
1               5

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Arg Arg Arg Arg Arg Arg Arg Arg Pro Ile Leu Thr Arg Ile
1               5                   10                  15

Thr Leu Glu

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 23

Arg Arg Arg Arg Arg Arg Arg Arg Arg Pro Ile Tyr Thr Arg Ile
1               5                   10                  15

Thr Leu Glu

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Arg Arg Arg Arg Arg Arg Arg Arg Pro Ile Glu Thr Arg Ile
1               5                   10                  15

Thr Leu Glu

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Arg Arg Arg Arg Arg Arg Arg Pro Ile Leu Thr Arg Ile
1               5                   10                  15

Tyr Leu Glu

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Arg Arg Arg Arg Arg Arg Arg Pro Ile Tyr Thr Arg Ile
1               5                   10                  15

Tyr Leu Glu

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Arg Arg Arg Arg Arg Arg Arg Pro Ile Trp Thr Arg Ile
1               5                   10                  15

Thr Leu Glu

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Arg Arg Arg Arg Arg Arg Arg Pro Ile Trp Thr Arg Ile
1               5                   10                  15

Tyr Leu Glu

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Arg Arg Arg Arg Arg Arg Arg Pro Ile Glu Thr Arg Ile
1               5                   10                  15

Tyr Leu Glu

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Arg Arg Arg Arg Arg Arg Arg Pro Ile Leu Thr Lys Ile
1               5                   10                  15

Thr Leu Glu

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Arg Arg Arg Arg Arg Arg Arg Pro Ile Tyr Thr Lys Ile
1               5                   10                  15

Thr Leu Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Arg Arg Arg Arg Arg Arg Arg Pro Ile Trp Thr Lys Ile
1               5                   10                  15

Thr Leu Glu

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Arg Arg Arg Arg Arg Arg Arg Arg Arg Arg Pro Ile Glu Thr Lys Ile
1               5                   10                  15

Thr Leu Glu

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Arg Arg Arg Arg Arg Arg Arg Arg Arg Pro Ile Leu Thr Lys Ile
1               5                   10                  15

Tyr Leu Glu

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Arg Arg Arg Arg Arg Arg Arg Arg Arg Pro Ile Tyr Thr Lys Ile
1               5                   10                  15

Tyr Leu Glu

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Arg Arg Arg Arg Arg Arg Arg Arg Pro Ile Glu Thr Lys Ile
1               5                   10                  15

Tyr Leu Glu

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu His Arg Ile Tyr Leu Glu
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 38

Leu Tyr Ile Arg Ile Leu Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: (Nme)Arg

<400> SEQUENCE: 39

Leu Thr Arg Ile Tyr Leu Glu
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (Nme)Tyr

<400> SEQUENCE: 40

Leu Thr Arg Ile Tyr Leu Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (Nme)Leu

<400> SEQUENCE: 41

Leu Thr Arg Ile Tyr Leu Glu
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: (Nme)Ile

<400> SEQUENCE: 42

Leu Thr Arg Ile Tyr Leu Glu
1               5
```

```
<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(16)
<223> OTHER INFORMATION: This sequence may encompass 5-16 'Arg'
      residues, wherein some positions may be absent

<400> SEQUENCE: 43

Arg Arg Arg Arg Arg Arg Arg Arg Arg Arg Arg Arg Arg Arg Arg Arg
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(16)
<223> OTHER INFORMATION: This sequence may encompass 5-16 'Lys'
      residues, wherein some positions may be absent

<400> SEQUENCE: 44

Lys Lys Lys Lys Lys Lys Lys Lys Lys Lys Lys Lys Lys Lys Lys Lys
1               5                   10                  15

<210> SEQ ID NO 45
<211> LENGTH: 18
<212> TYPE: PRT
<213> ORGANISM: Unknown
<220> FEATURE:
<223> OTHER INFORMATION: Description of Unknown: SynB1
      peptide

<400> SEQUENCE: 45

Arg Gly Gly Arg Leu Ser Tyr Ser Arg Arg Arg Phe Ser Thr Ser Thr
1               5                   10                  15

Gly Arg

<210> SEQ ID NO 46
<211> LENGTH: 10
<212> TYPE: PRT
<213> ORGANISM: Unknown
<220> FEATURE:
<223> OTHER INFORMATION: Description of Unknown: SynB3
      peptide

<400> SEQUENCE: 46

Arg Arg Leu Ser Tyr Ser Arg Arg Arg Phe
1               5                   10

<210> SEQ ID NO 47
<211> LENGTH: 16
<212> TYPE: PRT
<213> ORGANISM: Unknown
<220> FEATURE:
<223> OTHER INFORMATION: Description of Unknown: Penetratin
      peptide

<400> SEQUENCE: 47

Arg Gln Ile Lys Ile Trp Phe Gln Asn Arg Arg Met Lys Trp Lys Lys
```

```
<210> SEQ ID NO 48
<211> LENGTH: 16
<212> TYPE: PRT
<213> ORGANISM: Unknown
<220> FEATURE:
<223> OTHER INFORMATION: Description of Unknown: PenArg
      peptide

<400> SEQUENCE: 48

Arg Gln Ile Arg Ile Trp Phe Gln Asn Arg Arg Met Arg Trp Arg Arg
1               5                   10                  15

<210> SEQ ID NO 49
<211> LENGTH: 16
<212> TYPE: PRT
<213> ORGANISM: Unknown
<220> FEATURE:
<223> OTHER INFORMATION: Description of Unknown: PenLys
      peptide

<400> SEQUENCE: 49

Lys Gln Ile Lys Ile Trp Phe Gln Asn Lys Lys Met Lys Trp Lys Lys
1               5                   10                  15

<210> SEQ ID NO 50
<211> LENGTH: 13
<212> TYPE: PRT
<213> ORGANISM: Unknown
<220> FEATURE:
<223> OTHER INFORMATION: Description of Unknown: TatP59W
      peptide

<400> SEQUENCE: 50

Gly Arg Lys Lys Arg Arg Gln Arg Arg Pro Trp Gln
1               5                   10

<210> SEQ ID NO 51
<211> LENGTH: 13
<212> TYPE: PRT
<213> ORGANISM: Human immunodeficiency virus

<400> SEQUENCE: 51

Gly Arg Lys Lys Arg Arg Gln Arg Arg Pro Pro Gln
1               5                   10

<210> SEQ ID NO 52
<211> LENGTH: 13
<212> TYPE: PRT
<213> ORGANISM: Unknown
<220> FEATURE:
<223> OTHER INFORMATION: Description of Unknown: R9-Tat
      peptide

<400> SEQUENCE: 52

Gly Arg Arg Arg Arg Arg Arg Arg Arg Pro Pro Gln
1               5                   10

<210> SEQ ID NO 53
<211> LENGTH: 11
<212> TYPE: PRT
<213> ORGANISM: Human immunodeficiency virus

<400> SEQUENCE: 53

Tyr Gly Arg Lys Lys Arg Arg Gln Arg Arg Arg
1               5                   10
```

<210> SEQ ID NO 54
<211> LENGTH: 19
<212> TYPE: PRT
<213> ORGANISM: Brome mosaic virus

<400> SEQUENCE: 54

Lys Met Thr Arg Ala Gln Arg Arg Ala Ala Ala Arg Arg Asn Arg Trp
1               5                   10                  15

Thr Ala Arg

<210> SEQ ID NO 55
<211> LENGTH: 15
<212> TYPE: PRT
<213> ORGANISM: Feline herpes virus

<400> SEQUENCE: 55

Arg Arg Arg Arg Asn Arg Thr Arg Arg Asn Arg Arg Arg Val Arg
1               5                   10                  15

<210> SEQ ID NO 56
<211> LENGTH: 13
<212> TYPE: PRT
<213> ORGANISM: Human T-lymphotropic virus 2

<400> SEQUENCE: 56

Thr Arg Arg Gln Arg Thr Arg Arg Ala Arg Arg Asn Arg
1               5                   10

<210> SEQ ID NO 57
<211> LENGTH: 17
<212> TYPE: PRT
<213> ORGANISM: Unknown
<220> FEATURE:
<223> OTHER INFORMATION: Description of Unknown: P22 N-(14-30)
      peptide

<400> SEQUENCE: 57

Asn Ala Lys Thr Arg Arg His Glu Arg Arg Arg Lys Leu Ala Ile Glu
1               5                   10                  15

Arg

<210> SEQ ID NO 58
<211> LENGTH: 18
<212> TYPE: PRT
<213> ORGANISM: Unknown
<220> FEATURE:
<223> OTHER INFORMATION: Description of Unknown: pVEC
      peptide

<400> SEQUENCE: 58

Leu Leu Ile Ile Leu Arg Arg Arg Ile Arg Lys Gln Ala His Ala His
1               5                   10                  15

Ser Lys

<210> SEQ ID NO 59
<211> LENGTH: 27
<212> TYPE: PRT
<213> ORGANISM: Unknown
<220> FEATURE:
<223> OTHER INFORMATION: Description of Unknown: Transportan
      peptide

<400> SEQUENCE: 59

-continued

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 60
<211> LENGTH: 21
<212> TYPE: PRT
<213> ORGANISM: Unknown
<220> FEATURE:
<223> OTHER INFORMATION: Description of Unknown: TP10
      peptide

<400> SEQUENCE: 60

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 61
<211> LENGTH: 12
<212> TYPE: PRT
<213> ORGANISM: Unknown
<220> FEATURE:
<223> OTHER INFORMATION: Description of Unknown: PTD-4
      peptide

<400> SEQUENCE: 61

Pro Ile Arg Arg Arg Lys Lys Leu Arg Arg Leu Lys
1               5                   10

<210> SEQ ID NO 62
<211> LENGTH: 12
<212> TYPE: PRT
<213> ORGANISM: Unknown
<220> FEATURE:
<223> OTHER INFORMATION: Description of Unknown: PTD-5
      peptide

<400> SEQUENCE: 62

Arg Arg Gln Arg Arg Thr Ser Lys Leu Met Lys Arg
1               5                   10

<210> SEQ ID NO 63
<211> LENGTH: 21
<212> TYPE: PRT
<213> ORGANISM: Unknown
<220> FEATURE:
<223> OTHER INFORMATION: Description of Unknown: Pep-1
      peptide
<220> FEATURE:
<223> OTHER INFORMATION: N-term Ac
<220> FEATURE:
<223> OTHER INFORMATION: C-term cya

<400> SEQUENCE: 63

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 64
<211> LENGTH: 21
<212> TYPE: PRT
<213> ORGANISM: Unknown
<220> FEATURE:
<223> OTHER INFORMATION: Description of Unknown: Pep-2
```

```
                                peptide
<220> FEATURE:
<223> OTHER INFORMATION: N-term Ac
<220> FEATURE:
<223> OTHER INFORMATION: C-term cya

<400> SEQUENCE: 64

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 65
<211> LENGTH: 15
<212> TYPE: PRT
<213> ORGANISM: Unknown
<220> FEATURE:
<223> OTHER INFORMATION: Description of Unknown: Pep-3
                                peptide
<220> FEATURE:
<223> OTHER INFORMATION: N-term Ac
<220> FEATURE:
<223> OTHER INFORMATION: C-term cya

<400> SEQUENCE: 65

Lys Trp Phe Glu Thr Trp Phe Thr Glu Trp Pro Lys Lys Arg Lys
1               5                   10                  15

<210> SEQ ID NO 66
<211> LENGTH: 22
<212> TYPE: PRT
<213> ORGANISM: Unknown
<220> FEATURE:
<223> OTHER INFORMATION: Description of Unknown: E N(1-22)
                                peptide

<400> SEQUENCE: 66

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 67
<211> LENGTH: 18
<212> TYPE: PRT
<213> ORGANISM: Unknown
<220> FEATURE:
<223> OTHER INFORMATION: Description of Unknown: B 21 N-(12-29)
                                peptide

<400> SEQUENCE: 67

Thr Ala Lys Thr Arg Tyr Lys Ala Arg Arg Ala Glu Leu Ile Ala Glu
1               5                   10                  15

Arg Arg

<210> SEQ ID NO 68
<211> LENGTH: 12
<212> TYPE: PRT
<213> ORGANISM: Unknown
<220> FEATURE:
<223> OTHER INFORMATION: Description of Unknown: U2AF(142-153)
                                peptide

<400> SEQUENCE: 68

Ser Gln Met Thr Arg Gln Ala Arg Arg Leu Tyr Val
1               5                   10
```

<210> SEQ ID NO 69
<211> LENGTH: 16
<212> TYPE: PRT
<213> ORGANISM: Unknown
<220> FEATURE:
<223> OTHER INFORMATION: Description of Unknown: PRP6(129-144)
      peptide

<400> SEQUENCE: 69

Thr Arg Arg Asn Lys Arg Asn Arg Ile Gln Glu Gln Leu Asn Arg Lys
1               5                   10                  15

<210> SEQ ID NO 70
<211> LENGTH: 17
<212> TYPE: PRT
<213> ORGANISM: Unknown
<220> FEATURE:
<223> OTHER INFORMATION: Description of Unknown: MAP
      peptide

<400> SEQUENCE: 70

Lys Leu Ala Leu Lys Leu Ala Leu Lys Leu Ala Leu Ala Leu Lys Leu
1               5                   10                  15

Ala

<210> SEQ ID NO 71
<211> LENGTH: 27
<212> TYPE: PRT
<213> ORGANISM: Unknown
<220> FEATURE:
<223> OTHER INFORMATION: Description of Unknown: SBP
      peptide

<400> SEQUENCE: 71

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 72
<211> LENGTH: 27
<212> TYPE: PRT
<213> ORGANISM: Unknown
<220> FEATURE:
<223> OTHER INFORMATION: Description of Unknown: FBP
      peptide

<400> SEQUENCE: 72

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 73
<211> LENGTH: 27
<212> TYPE: PRT
<213> ORGANISM: Unknown
<220> FEATURE:
<223> OTHER INFORMATION: Description of Unknown: MPG
      peptide
<220> FEATURE:
<223> OTHER INFORMATION: N-term Ac
<220> FEATURE:
<223> OTHER INFORMATION: C-term cya

<400> SEQUENCE: 73

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 74
<211> LENGTH: 27
<212> TYPE: PRT
<213> ORGANISM: Unknown
<220> FEATURE:
<223> OTHER INFORMATION: Description of Unknown: MPG(delta-NLS)
      peptide
<220> FEATURE:
<223> OTHER INFORMATION: N-term Ac
<220> FEATURE:
<223> OTHER INFORMATION: C-term cya

<400> SEQUENCE: 74

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 75
<211> LENGTH: 17
<212> TYPE: PRT
<213> ORGANISM: Unknown
<220> FEATURE:
<223> OTHER INFORMATION: Description of Unknown: REV(34-50)
      peptide

<400> SEQUENCE: 75

Thr Arg Gln Ala Arg Arg Asn Arg Arg Arg Arg Trp Arg Glu Arg Gln
1               5                   10                  15

Arg

<210> SEQ ID NO 76
<211> LENGTH: 23
<212> TYPE: PRT
<213> ORGANISM: Unknown
<220> FEATURE:
<223> OTHER INFORMATION: Description of Unknown: ACPP
      peptide
<220> FEATURE:
<221> NAME/KEY: misc_feature
<222> LOCATION: (10)..(11)
<223> OTHER INFORMATION: Residues at these positions are non-
      consecutive and are separated by a non-disclosed protease
      cleavage site
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (22)..(22)
<223> OTHER INFORMATION: Any amino acid

<400> SEQUENCE: 76

Glu Glu Glu Glu Glu Asp Asp Asp Asp Lys Ala Xaa Arg Arg Arg Arg
1               5                   10                  15

Arg Arg Arg Arg Arg Xaa Cys
            20

<210> SEQ ID NO 77
<211> LENGTH: 22
<212> TYPE: PRT
<213> ORGANISM: Unknown
```

```
<220> FEATURE:
<223> OTHER INFORMATION: Description of Unknown: ACPP
      peptide
<220> FEATURE:
<221> NAME/KEY: misc_feature
<222> LOCATION: (10)..(11)
<223> OTHER INFORMATION: Residues at these positions are non-
      consecutive and are separated by a non-disclosed protease
      cleavage site
<220> FEATURE:
<221> NAME/KEY: MOD_RES
<222> LOCATION: (21)..(21)
<223> OTHER INFORMATION: Any amino acid

<400> SEQUENCE: 77

Glu Glu Glu Glu Glu Asp Asp Asp Asp Lys Ala Arg Arg Arg Arg
1               5                   10                  15

Arg Arg Arg Arg Xaa Cys
                20

<210> SEQ ID NO 78
<211> LENGTH: 19
<212> TYPE: PRT
<213> ORGANISM: Unknown
<220> FEATURE:
<223> OTHER INFORMATION: Description of Unknown: ACPP
      peptide
<220> FEATURE:
<221> NAME/KEY: misc_feature
<222> LOCATION: (6)..(7)
<223> OTHER INFORMATION: Residues at these positions are non-
      consecutive and are separated by a non-disclosed protease
      cleavage site
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 78

Glu Asp Asp Asp Asp Lys Ala Xaa Arg Arg Arg Arg Arg Arg Arg
1               5                   10                  15

Arg Xaa Cys

<210> SEQ ID NO 79
<211> LENGTH: 23
<212> TYPE: PRT
<213> ORGANISM: Unknown
<220> FEATURE:
<223> OTHER INFORMATION: Description of Unknown: ACPP
      peptide
<220> FEATURE:
<221> NAME/KEY: misc_feature
<222> LOCATION: (7)..(8)
<223> OTHER INFORMATION: Residues at these positions are non-
      consecutive and are separated by a non-disclosed protease
      cleavage site
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
```

```
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (22)..(22)
<223> OTHER INFORMATION: Any amino acid

<400> SEQUENCE: 79

Glu Glu Asp Asp Asp Asp Lys Ala Arg Xaa Arg Arg Xaa Arg Arg Xaa
1               5                   10                  15

Arg Arg Xaa Arg Arg Xaa Cys
            20

<210> SEQ ID NO 80
<211> LENGTH: 19
<212> TYPE: PRT
<213> ORGANISM: Unknown
<220> FEATURE:
<223> OTHER INFORMATION: Description of Unknown: ACPP
      peptide
<220> FEATURE:
<221> NAME/KEY: misc_feature
<222> LOCATION: (7)..(8)
<223> OTHER INFORMATION: Residues at these positions are non-
      consecutive and are separated by a non-disclosed protease
      cleavage site
<220> FEATURE:
<221> NAME/KEY: MOD_RES
<222> LOCATION: (18)..(18)
<223> OTHER INFORMATION: Any amino acid

<400> SEQUENCE: 80

Asp Asp Asp Asp Asp Asp Lys Ala Arg Arg Arg Arg Arg Arg Arg
1               5                   10                  15

Arg Xaa Cys

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Met Asn Arg Arg Pro Ile
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Phe Leu Leu Trp Gln Arg
1               5
```